United States Patent
Cam et al.

(10) Patent No.: US 11,123,156 B2
(45) Date of Patent: Sep. 21, 2021

(54) DENTAL APPLIANCE COMPLIANCE MONITORING

(71) Applicant: Align Technology, Inc., San Jose, CA (US)

(72) Inventors: Bruce Cam, San Jose, CA (US); Yaser Shanjani, San Jose, CA (US); Edi Fridman, Rishon le Zion (IL); Sergey Vinnichenko, Cary, NC (US); Jun Sato, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 235 days.

(21) Appl. No.: 16/104,781

(22) Filed: Aug. 17, 2018

(65) Prior Publication Data

US 2019/0069975 A1     Mar. 7, 2019

Related U.S. Application Data

(60) Provisional application No. 62/546,987, filed on Aug. 17, 2017.

(51) Int. Cl.
*A61C 7/08*      (2006.01)
*A61C 7/00*      (2006.01)
(Continued)

(52) U.S. Cl.
CPC .............. *A61C 7/08* (2013.01); *A61B 5/4833* (2013.01); *A61C 7/002* (2013.01); *A61C 19/04* (2013.01); *A61C 2204/007* (2013.01)

(58) Field of Classification Search
CPC ........... A61C 7/08; A61C 7/002; A61C 19/04; A61C 2204/007; A61C 2204/005; A61B 5/4833; A61B 5/48
(Continued)

(56) References Cited

U.S. PATENT DOCUMENTS 2,171,695 A     9/1939   Harper
2,194,790 A     3/1940   Gluck
(Continued)

FOREIGN PATENT DOCUMENTS

AU          517102 B      11/1977
AU         3031677 A      11/1977
(Continued)

OTHER PUBLICATIONS

US 8,553,966 B1, 10/2013, Alpern et al. (withdrawn)
(Continued)

*Primary Examiner* — Nicholas D Lucchesi
*Assistant Examiner* — Mirayda A Aponte
(74) *Attorney, Agent, or Firm* — Shay Glenn LLP

(57) ABSTRACT

The present disclosure describes devices, systems, and methods for monitoring use of an oral appliance in an oral cavity using extra-oral sensor(s). One method includes sensing one or more physical properties of an oral appliance using an extra-oral sensor, providing a compliance signal from the extra-oral sensor, the compliance signal including an electronic representation of the one or more physical properties of the oral appliance, identifying one or more patient compliance factors based on the compliance signal, the one or more patient compliance factors providing a basis to identify an extent of compliance of usage of the oral appliance with an orthodontic treatment plan, and providing one or more compliances indicators based on the one or more patient compliance factors, the one or more compliance indicators providing a basis to indicate the extent of compliance.

29 Claims, 11 Drawing Sheets

(51) Int. Cl.
*A61C 19/04* (2006.01)
*A61B 5/00* (2006.01)

(58) Field of Classification Search
USPC ........ 433/24; 206/63.5, 83, 368–369, 209.1;
602/349; 340/870.02
See application file for complete search history.

(56) References Cited

U.S. PATENT DOCUMENTS

| | | |
|---|---|---|
| 2,467,432 A | 4/1949 | Kesling |
| 2,531,222 A | 11/1950 | Kesling |
| 2,835,628 A | 5/1958 | Saffir |
| 3,089,487 A | 5/1963 | Enicks et al. |
| 3,092,907 A | 6/1963 | Traiger |
| 3,178,820 A | 4/1965 | Kesling |
| 3,211,143 A | 10/1965 | Grossberg |
| 3,379,193 A | 4/1968 | Monsghan |
| 3,385,291 A | 5/1968 | Martin |
| 3,407,500 A | 10/1968 | Kesling |
| 3,478,742 A | 11/1969 | Bohlmann |
| 3,496,936 A | 2/1970 | Gores |
| 3,503,127 A | 3/1970 | Kasdin et al. |
| 3,533,163 A | 10/1970 | Kirschenbaum |
| 3,556,093 A | 1/1971 | Quick |
| 3,600,808 A | 8/1971 | Reeve |
| 3,660,900 A | 5/1972 | Andrews |
| 3,683,502 A | 8/1972 | Wallshein |
| 3,724,075 A | 4/1973 | Kesling |
| 3,738,005 A | 6/1973 | Cohen et al. |
| 3,797,115 A | 3/1974 | Silverman et al. |
| 3,813,781 A | 6/1974 | Forgione |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,949,477 A | 4/1976 | Cohen et al. |
| 3,950,851 A | 4/1976 | Bergersen |
| 3,955,282 A | 5/1976 | McNall |
| 3,983,628 A | 10/1976 | Acevedo |
| 4,014,096 A | 3/1977 | Dellinger |
| 4,039,653 A | 8/1977 | DeFoney et al. |
| 4,055,895 A | 11/1977 | Huge |
| 4,094,068 A | 6/1978 | Schinhammer |
| 4,117,596 A | 10/1978 | Wallshein |
| 4,129,946 A | 12/1978 | Kennedy |
| 4,134,208 A | 1/1979 | Pearlman |
| 4,139,944 A | 2/1979 | Bergersen |
| 4,179,811 A | 12/1979 | Hinz |
| 4,179,812 A | 12/1979 | White |
| 4,183,141 A | 1/1980 | Dellinger |
| 4,195,046 A | 3/1980 | Kesling |
| 4,204,325 A | 5/1980 | Kaelble |
| 4,253,828 A | 3/1981 | Coles et al. |
| 4,255,138 A | 3/1981 | Frohn |
| 4,278,087 A | 7/1981 | Theeuwes |
| 4,299,568 A | 11/1981 | Crowley |
| 4,324,546 A | 4/1982 | Heitlinger et al. |
| 4,324,547 A | 4/1982 | Arcan et al. |
| 4,348,178 A | 9/1982 | Kurz |
| 4,368,040 A | 1/1983 | Weissman |
| 4,419,992 A | 12/1983 | Chorbajian |
| 4,433,956 A | 2/1984 | Witzig |
| 4,433,960 A | 2/1984 | Garito et al. |
| 4,439,154 A | 3/1984 | Mayclin |
| 4,449,928 A | 5/1984 | von Weissenfluh |
| 4,450,150 A | 5/1984 | Sidman |
| 4,478,580 A | 10/1984 | Barrut |
| 4,500,294 A | 2/1985 | Lewis |
| 4,505,672 A | 3/1985 | Kurz |
| 4,505,673 A | 3/1985 | Yoshii |
| 4,519,386 A | 5/1985 | Sullivan |
| 4,523,908 A | 6/1985 | Drisaldi et al. |
| 4,526,540 A | 7/1985 | Dellinger |
| 4,553,936 A | 11/1985 | Wang |
| 4,575,330 A | 3/1986 | Hull |
| 4,575,805 A | 3/1986 | Moermann et al. |
| 4,591,341 A | 5/1986 | Andrews |
| 4,608,021 A | 8/1986 | Barrett |
| 4,609,349 A | 9/1986 | Cain |
| 4,611,288 A | 9/1986 | Duret et al. |
| 4,629,424 A * | 12/1986 | Lauks ................. A61B 5/0002 257/417 |
| 4,638,145 A | 1/1987 | Sakuma et al. |
| 4,656,860 A | 4/1987 | Orthuber et al. |
| 4,663,720 A | 5/1987 | Duret et al. |
| 4,664,626 A | 5/1987 | Kesling |
| 4,665,621 A | 5/1987 | Ackerman et al. |
| 4,676,747 A | 6/1987 | Kesling |
| 4,741,700 A | 5/1988 | Barabe |
| 4,755,139 A | 7/1988 | Abbatte et al. |
| 4,757,824 A | 7/1988 | Chaumet |
| 4,763,791 A | 8/1988 | Halverson et al. |
| 4,764,111 A | 8/1988 | Knierim |
| 4,790,752 A | 12/1988 | Cheslak |
| 4,793,803 A | 12/1988 | Martz |
| 4,798,534 A | 1/1989 | Breads |
| 4,818,542 A | 4/1989 | De Luca et al. |
| 4,830,612 A | 5/1989 | Bergersen |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,861,268 A | 8/1989 | Garay et al. |
| 4,877,398 A | 10/1989 | Kesling |
| 4,880,380 A | 11/1989 | Martz |
| 4,886,451 A | 12/1989 | Cetlin |
| 4,889,238 A | 12/1989 | Batchelor |
| 4,890,608 A | 1/1990 | Steer |
| 4,932,866 A | 6/1990 | Guis |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,952,928 A | 8/1990 | Carroll et al. |
| 4,964,770 A | 10/1990 | Steinbichler et al. |
| 4,968,251 A | 11/1990 | Darnell |
| 4,971,557 A | 11/1990 | Martin |
| 4,975,052 A | 12/1990 | Spencer et al. |
| 4,983,334 A | 1/1991 | Adell |
| 4,997,369 A | 3/1991 | Shafir |
| 5,002,485 A | 3/1991 | Aagesen |
| 5,011,405 A | 4/1991 | Lemchen |
| 5,015,183 A | 5/1991 | Fenick |
| 5,017,133 A | 5/1991 | Miura |
| 5,018,969 A | 5/1991 | Andreiko et al. |
| 5,027,281 A | 6/1991 | Rekow et al. |
| 5,035,613 A | 7/1991 | Breads et al. |
| 5,037,295 A | 8/1991 | Bergersen |
| 5,049,077 A | 9/1991 | Goldin et al. |
| 5,055,039 A | 10/1991 | Abbatte et al. |
| 5,061,839 A | 10/1991 | Matsuno et al. |
| 5,083,919 A | 1/1992 | Quachi |
| 5,094,614 A | 3/1992 | Wildman |
| 5,100,316 A | 3/1992 | Wildman |
| 5,103,838 A | 4/1992 | Yousif |
| 5,114,339 A | 5/1992 | Guis |
| 5,121,333 A | 6/1992 | Riley et al. |
| 5,123,425 A | 6/1992 | Shannon et al. |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,194,003 A | 3/1993 | Garay et al. |
| 5,204,670 A | 4/1993 | Stinton |
| 5,222,499 A | 6/1993 | Allen et al. |
| 5,224,049 A | 6/1993 | Mushabac |
| 5,238,404 A | 8/1993 | Andreiko |
| 5,242,304 A | 9/1993 | Truax et al. |
| 5,245,592 A | 9/1993 | Kuemmel et al. |
| 5,273,429 A | 12/1993 | Rekow et al. |

(56) References Cited

U.S. PATENT DOCUMENTS

| | | |
|---|---|---|
| 5,278,756 A | 1/1994 | Lemchen et al. |
| 5,306,144 A | 4/1994 | Hibst et al. |
| 5,314,335 A | 5/1994 | Fung |
| 5,324,186 A | 6/1994 | Bakanowski |
| 5,328,362 A | 7/1994 | Watson et al. |
| 5,335,657 A | 8/1994 | Terry et al. |
| 5,338,198 A | 8/1994 | Wu et al. |
| 5,340,309 A | 8/1994 | Robertson |
| 5,342,202 A | 8/1994 | Deshayes |
| 5,344,315 A | 9/1994 | Hanson |
| 5,368,478 A | 11/1994 | Andreiko et al. |
| 5,372,502 A | 12/1994 | Massen et al. |
| D354,355 S | 1/1995 | Hilgers |
| 5,382,164 A | 1/1995 | Stern |
| 5,395,238 A | 3/1995 | Andreiko et al. |
| 5,415,542 A | 5/1995 | Kesling |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,449,703 A | 9/1995 | Mitra et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,487,662 A | 1/1996 | Kipke et al. |
| RE35,169 E | 3/1996 | Lemchen et al. |
| 5,499,633 A | 3/1996 | Fenton |
| 5,522,725 A | 6/1996 | Jordan et al. |
| 5,528,735 A | 6/1996 | Strasnick et al. |
| 5,533,895 A | 7/1996 | Andreiko et al. |
| 5,540,732 A | 7/1996 | Testerman |
| 5,542,842 A | 8/1996 | Andreiko et al. |
| 5,543,780 A | 8/1996 | McAuley et al. |
| 5,549,476 A | 8/1996 | Stern |
| 5,562,448 A | 10/1996 | Mushabac |
| 5,570,182 A | 10/1996 | Nathel et al. |
| 5,575,655 A | 11/1996 | Darnell |
| 5,583,977 A | 12/1996 | Seidl |
| 5,587,912 A | 12/1996 | Andersson et al. |
| 5,588,098 A | 12/1996 | Chen et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,626,537 A | 5/1997 | Danyo et al. |
| 5,636,736 A | 6/1997 | Jacobs et al. |
| 5,645,420 A | 7/1997 | Bergersen |
| 5,645,421 A | 7/1997 | Slootsky |
| 5,651,671 A | 7/1997 | Seay et al. |
| 5,655,653 A | 8/1997 | Chester |
| 5,659,420 A | 8/1997 | Wakai et al. |
| 5,683,243 A | 11/1997 | Andreiko et al. |
| 5,683,244 A | 11/1997 | Truax |
| 5,691,539 A | 11/1997 | Pfeiffer |
| 5,692,894 A | 12/1997 | Schwartz et al. |
| 5,711,665 A | 1/1998 | Adam et al. |
| 5,711,666 A | 1/1998 | Hanson |
| 5,725,376 A | 3/1998 | Poirier |
| 5,725,378 A | 3/1998 | Wang |
| 5,730,151 A | 3/1998 | Summer et al. |
| 5,737,084 A | 4/1998 | Ishihara |
| 5,740,267 A | 4/1998 | Echerer et al. |
| 5,742,700 A | 4/1998 | Yoon et al. |
| 5,769,631 A | 6/1998 | Williams |
| 5,774,425 A | 6/1998 | Ivanov et al. |
| 5,790,242 A | 8/1998 | Stern et al. |
| 5,799,100 A | 8/1998 | Clarke et al. |
| 5,800,162 A | 9/1998 | Shimodaira et al. |
| 5,800,174 A | 9/1998 | Andersson |
| 5,813,854 A | 9/1998 | Nikodem |
| 5,816,800 A | 10/1998 | Brehm et al. |
| 5,818,587 A | 10/1998 | Devaraj et al. |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,876,199 A | 3/1999 | Bergersen |
| 5,879,158 A | 3/1999 | Doyle et al. |
| 5,880,961 A | 3/1999 | Crump |
| 5,880,962 A | 3/1999 | Andersson et al. |
| 5,882,192 A | 3/1999 | Bergersen |
| 5,886,702 A | 3/1999 | Migdal et al. |
| 5,890,896 A | 4/1999 | Padial |
| 5,904,479 A | 5/1999 | Staples |
| 5,911,576 A | 6/1999 | Ulrich et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,975,906 A | 11/1999 | Knutson |
| 5,980,246 A | 11/1999 | Ramsay et al. |
| 5,989,023 A | 11/1999 | Summer et al. |
| 5,993,413 A | 11/1999 | Aaltonen et al. |
| 6,002,706 A | 12/1999 | Staver et al. |
| 6,018,713 A | 1/2000 | Coli et al. |
| 6,044,309 A | 3/2000 | Honda |
| 6,049,743 A | 4/2000 | Baba |
| 6,053,731 A | 4/2000 | Heckenberger |
| 6,068,482 A | 5/2000 | Snow |
| 6,070,140 A | 5/2000 | Tran |
| 6,099,303 A | 8/2000 | Gibbs et al. |
| 6,099,314 A | 8/2000 | Kopelman et al. |
| 6,102,701 A | 8/2000 | Engeron |
| 6,120,287 A | 9/2000 | Chen |
| 6,123,544 A | 9/2000 | Cleary |
| 6,152,731 A | 11/2000 | Jordan et al. |
| 6,154,676 A | 11/2000 | Levine |
| 6,183,248 B1 | 2/2001 | Chishti et al. |
| 6,183,249 B1 | 2/2001 | Brennan et al. |
| 6,186,780 B1 | 2/2001 | Hibst et al. |
| 6,190,165 B1 | 2/2001 | Andreiko et al. |
| 6,200,133 B1 | 3/2001 | Kittelsen |
| 6,201,880 B1 | 3/2001 | Elbaum et al. |
| 6,210,162 B1 | 4/2001 | Chishti et al. |
| 6,212,435 B1 | 4/2001 | Lattner et al. |
| 6,213,767 B1 | 4/2001 | Dixon et al. |
| 6,217,334 B1 | 4/2001 | Hultgren |
| 6,227,850 B1 | 5/2001 | Chishti et al. |
| 6,230,142 B1 | 5/2001 | Benigno et al. |
| 6,231,338 B1 | 5/2001 | de Josselin de Jong et al. |
| 6,239,705 B1 | 5/2001 | Glen |
| 6,243,601 B1 | 6/2001 | Wist |
| 6,263,234 B1 | 7/2001 | Engelhardt et al. |
| 6,283,761 B1 | 9/2001 | Joao |
| 6,288,138 B1 | 9/2001 | Yamamoto |
| 6,299,438 B1 | 10/2001 | Sahagian et al. |
| 6,309,215 B1 | 10/2001 | Phan et al. |
| 6,313,432 B1 | 11/2001 | Nagata et al. |
| 6,315,553 B1 | 11/2001 | Sachdeva et al. |
| 6,328,745 B1 | 12/2001 | Ascherman |
| 6,332,774 B1 | 12/2001 | Chikami |
| 6,334,073 B1 | 12/2001 | Levine |
| 6,350,120 B1 | 2/2002 | Sachdeva et al. |
| 6,364,660 B1 | 4/2002 | Durbin et al. |
| 6,382,975 B1 | 5/2002 | Poirier |
| 6,386,878 B1 | 5/2002 | Pavlovskaia et al. |
| 6,394,802 B1 | 5/2002 | Hahn |
| 6,402,510 B1 | 6/2002 | Williams |
| 6,402,707 B1 | 6/2002 | Ernst |
| 6,405,729 B1 | 6/2002 | Thornton |
| 6,406,292 B1 | 6/2002 | Chishti et al. |
| 6,409,504 B1 | 6/2002 | Jones et al. |
| 6,413,086 B1 | 7/2002 | Womack |
| 6,414,264 B1 | 7/2002 | von Falkenhausen |
| 6,414,708 B1 | 7/2002 | Carmeli et al. |
| 6,435,871 B1 | 8/2002 | Inman |
| 6,436,058 B1 | 8/2002 | Krahner et al. |
| 6,441,354 B1 | 8/2002 | Seghatol et al. |
| 6,450,167 B1 | 9/2002 | David et al. |
| 6,450,807 B1 | 9/2002 | Chishti et al. |
| 6,462,301 B1 | 10/2002 | Scott et al. |
| 6,470,338 B1 | 10/2002 | Rizzo et al. |

(56) References Cited

U.S. PATENT DOCUMENTS

| | | |
|---|---|---|
| 6,471,511 B1 | 10/2002 | Chishti et al. |
| 6,471,512 B1 | 10/2002 | Sachdeva et al. |
| 6,471,970 B1 | 10/2002 | Fanara et al. |
| 6,482,002 B2 | 11/2002 | Jordan et al. |
| 6,482,298 B1 | 11/2002 | Bhatnagar |
| 6,496,814 B1 | 12/2002 | Busche |
| 6,496,816 B1 | 12/2002 | Thiesson et al. |
| 6,499,026 B1 | 12/2002 | Rivette et al. |
| 6,499,995 B1 | 12/2002 | Schwartz |
| 6,507,832 B1 | 1/2003 | Evans et al. |
| 6,514,074 B1 | 2/2003 | Chishti et al. |
| 6,515,593 B1 | 2/2003 | Stark et al. |
| 6,516,288 B2 | 2/2003 | Bagne |
| 6,516,805 B1 | 2/2003 | Thornton |
| 6,520,772 B2 | 2/2003 | Williams |
| 6,523,009 B1 | 2/2003 | Wilkins |
| 6,523,019 B1 | 2/2003 | Borthwick |
| 6,524,101 B1 | 2/2003 | Phan et al. |
| 6,526,168 B1 | 2/2003 | Ornes et al. |
| 6,526,982 B1 | 3/2003 | Strong |
| 6,529,891 B1 | 3/2003 | Heckerman |
| 6,529,902 B1 | 3/2003 | Kanevsky et al. |
| 6,532,455 B1 | 3/2003 | Martin et al. |
| 6,535,865 B1 | 3/2003 | Skaaning et al. |
| 6,540,512 B1 | 4/2003 | Sachdeva et al. |
| 6,540,707 B1 | 4/2003 | Stark et al. |
| 6,542,593 B1 | 4/2003 | Bowman Amuah |
| 6,542,881 B1 | 4/2003 | Meidan et al. |
| 6,542,894 B1 | 4/2003 | Lee et al. |
| 6,542,903 B2 | 4/2003 | Hull et al. |
| 6,551,243 B2 | 4/2003 | Bocionek et al. |
| 6,554,837 B1 | 4/2003 | Hauri et al. |
| 6,556,659 B1 | 4/2003 | Bowman Amuah |
| 6,556,977 B1 | 4/2003 | Lapointe et al. |
| 6,560,592 B1 | 5/2003 | Reid et al. |
| 6,564,209 B1 | 5/2003 | Dempski et al. |
| 6,567,814 B1 | 5/2003 | Bankier et al. |
| 6,571,227 B1 | 5/2003 | Agrafiotis et al. |
| 6,572,372 B1 | 6/2003 | Phan et al. |
| 6,573,998 B2 | 6/2003 | Cohen Sabban |
| 6,574,561 B2 | 6/2003 | Alexander et al. |
| 6,578,003 B1 | 6/2003 | Camarda et al. |
| 6,580,948 B2 | 6/2003 | Haupert et al. |
| 6,587,529 B1 | 7/2003 | Staszewski et al. |
| 6,587,828 B1 | 7/2003 | Sachdeva |
| 6,592,368 B1 | 7/2003 | Weathers |
| 6,594,539 B1 | 7/2003 | Geng |
| 6,595,342 B1 | 7/2003 | Maritzen et al. |
| 6,597,934 B1 | 7/2003 | de Jong et al. |
| 6,598,043 B1 | 7/2003 | Baclawski |
| 6,599,250 B2 | 7/2003 | Webb et al. |
| 6,602,070 B2 | 8/2003 | Miller et al. |
| 6,604,527 B1 | 8/2003 | Palmisano |
| 6,606,744 B1 | 8/2003 | Mikurak |
| 6,607,382 B1 | 8/2003 | Kuo et al. |
| 6,611,783 B2 | 8/2003 | Kelly et al. |
| 6,611,867 B1 | 8/2003 | Bowman Amuah |
| 6,613,001 B1 | 9/2003 | Dworkin |
| 6,615,158 B2 | 9/2003 | Wenzel et al. |
| 6,616,447 B1 | 9/2003 | Rizoiu et al. |
| 6,616,579 B1 | 9/2003 | Reinbold et al. |
| 6,621,491 B1 | 9/2003 | Baumrind et al. |
| 6,623,698 B2 | 9/2003 | Kuo |
| 6,624,752 B2 | 9/2003 | Klitsgaard et al. |
| 6,626,180 B1 | 9/2003 | Kittelsen et al. |
| 6,626,569 B2 | 9/2003 | Reinstein et al. |
| 6,626,669 B2 | 9/2003 | Zegarelli |
| 6,633,772 B2 | 10/2003 | Ford et al. |
| 6,640,128 B2 | 10/2003 | Vilsmeier et al. |
| 6,643,646 B2 | 11/2003 | Su et al. |
| 6,647,383 B1 | 11/2003 | August et al. |
| 6,650,944 B2 | 11/2003 | Goedeke et al. |
| 6,671,818 B1 | 12/2003 | Mikurak |
| 6,675,104 B2 | 1/2004 | Paulse et al. |
| 6,678,669 B2 | 1/2004 | Lapointe et al. |
| 6,682,346 B2 | 1/2004 | Chishti et al. |
| 6,685,469 B2 | 2/2004 | Chishti et al. |
| 6,689,055 B1 | 2/2004 | Mullen et al. |
| 6,690,761 B2 | 2/2004 | Lang et al. |
| 6,691,110 B2 | 2/2004 | Wang et al. |
| 6,694,234 B2 | 2/2004 | Lockwood et al. |
| 6,697,164 B1 | 2/2004 | Babayoff et al. |
| 6,697,793 B2 | 2/2004 | McGreevy |
| 6,702,765 B2 | 3/2004 | Robbins et al. |
| 6,702,804 B1 | 3/2004 | Ritter et al. |
| 6,705,863 B2 | 3/2004 | Phan et al. |
| 6,729,876 B2 | 5/2004 | Chishti et al. |
| 6,733,289 B2 | 5/2004 | Manemann et al. |
| 6,736,638 B1 | 5/2004 | Sachdeva et al. |
| 6,739,869 B1 | 5/2004 | Taub et al. |
| 6,744,932 B1 | 6/2004 | Rubbert et al. |
| 6,749,414 B1 | 6/2004 | Hanson et al. |
| 6,769,913 B2 | 8/2004 | Hurson |
| 6,772,026 B2 | 8/2004 | Bradbury et al. |
| 6,790,036 B2 | 9/2004 | Graham |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,832,912 B2 | 12/2004 | Mao |
| 6,832,914 B1 | 12/2004 | Bonnet et al. |
| 6,843,370 B2 | 1/2005 | Tuneberg |
| 6,845,175 B2 | 1/2005 | Kopelman et al. |
| 6,885,464 B1 | 4/2005 | Pfeiffer et al. |
| 6,890,285 B2 | 5/2005 | Rahman et al. |
| 6,951,254 B2 | 10/2005 | Morrison |
| 6,976,841 B1 | 12/2005 | Osterwalder |
| 6,978,268 B2 | 12/2005 | Thomas et al. |
| 6,983,752 B2 | 1/2006 | Garabadian |
| 6,984,128 B2 | 1/2006 | Breining et al. |
| 6,988,893 B2 | 1/2006 | Haywood |
| 7,016,952 B2 | 3/2006 | Mullen et al. |
| 7,020,963 B2 | 4/2006 | Cleary et al. |
| 7,036,514 B2 | 5/2006 | Heck |
| 7,040,896 B2 | 5/2006 | Pavlovskaia et al. |
| 7,106,233 B2 | 9/2006 | Schroeder et al. |
| 7,112,065 B2 | 9/2006 | Kopelman et al. |
| 7,121,825 B2 | 10/2006 | Chishti et al. |
| 7,134,874 B2 | 11/2006 | Chishti et al. |
| 7,137,812 B2 | 11/2006 | Cleary et al. |
| 7,138,640 B1 | 11/2006 | Delgado et al. |
| 7,140,877 B2 | 11/2006 | Kaza |
| 7,142,312 B2 | 11/2006 | Quadling et al. |
| 7,155,373 B2 | 12/2006 | Jordan et al. |
| 7,156,655 B2 | 1/2007 | Sachdeva et al. |
| 7,156,661 B2 | 1/2007 | Choi et al. |
| 7,166,063 B2 | 1/2007 | Rahman et al. |
| 7,184,150 B2 | 2/2007 | Quadling et al. |
| 7,191,451 B2 | 3/2007 | Nakagawa |
| 7,192,273 B2 | 3/2007 | McSurdy |
| 7,194,781 B1 | 3/2007 | Orjela |
| 7,217,131 B2 | 5/2007 | Vuillemot |
| 7,220,122 B2 | 5/2007 | Chishti |
| 7,220,124 B2 | 5/2007 | Taub et al. |
| 7,229,282 B2 | 6/2007 | Andreiko et al. |
| 7,234,937 B2 | 6/2007 | Sachdeva et al. |
| 7,241,142 B2 | 7/2007 | Abolfathi et al. |
| 7,244,230 B2 | 7/2007 | Duggirala et al. |
| 7,245,753 B2 | 7/2007 | Squilla et al. |
| 7,257,136 B2 | 8/2007 | Mori et al. |
| 7,286,954 B2 | 10/2007 | Kopelman et al. |
| 7,292,759 B2 | 11/2007 | Boutoussov et al. |
| 7,294,141 B2 | 11/2007 | Bergersen |
| 7,302,842 B2 | 12/2007 | Biester et al. |
| 7,320,592 B2 | 1/2008 | Chishti et al. |
| 7,328,706 B2 | 2/2008 | Barach et al. |
| 7,329,122 B1 | 2/2008 | Scott |
| 7,338,327 B2 | 3/2008 | Sticker et al. |
| D565,509 S | 4/2008 | Fechner et al. |
| 7,351,116 B2 | 4/2008 | Dold |
| 7,354,270 B2 | 4/2008 | Abolfathi et al. |
| 7,357,637 B2 | 4/2008 | Liechtung |
| 7,435,083 B2 | 10/2008 | Chishti et al. |
| 7,450,231 B2 | 11/2008 | Johs et al. |
| 7,458,810 B2 | 12/2008 | Bergersen |

(56) References Cited

U.S. PATENT DOCUMENTS

| | | |
|---|---|---|
| 7,460,230 B2 | 12/2008 | Johs et al. |
| 7,462,076 B2 | 12/2008 | Walter et al. |
| 7,463,929 B2 | 12/2008 | Simmons |
| 7,476,100 B2 | 1/2009 | Kuo |
| 7,500,851 B2 | 3/2009 | Williams |
| D594,413 S | 6/2009 | Palka et al. |
| 7,543,511 B2 | 6/2009 | Kimura et al. |
| 7,544,103 B2 | 6/2009 | Walter et al. |
| 7,553,157 B2 | 6/2009 | Abolfathi et al. |
| 7,561,273 B2 | 7/2009 | Stautmeister et al. |
| 7,577,284 B2 | 8/2009 | Wong et al. |
| 7,596,253 B2 | 9/2009 | Wong et al. |
| 7,597,594 B2 | 10/2009 | Stadler et al. |
| 7,609,875 B2 | 10/2009 | Liu et al. |
| D603,796 S | 11/2009 | Sticker et al. |
| 7,616,319 B1 | 11/2009 | Woollam et al. |
| 7,626,705 B2 | 12/2009 | Altendorf |
| 7,632,216 B2 | 12/2009 | Rahman et al. |
| 7,633,625 B1 | 12/2009 | Woollam et al. |
| 7,637,262 B2 | 12/2009 | Bailey |
| 7,637,740 B2 | 12/2009 | Knopp |
| 7,641,473 B2 | 1/2010 | Sporbert et al. |
| 7,668,355 B2 | 2/2010 | Wong et al. |
| 7,670,179 B2 | 3/2010 | Müller |
| 7,695,327 B2 | 4/2010 | Bäuerle et al. |
| 7,698,068 B2 | 4/2010 | Babayoff |
| 7,711,447 B2 | 5/2010 | Lu et al. |
| 7,724,378 B2 | 5/2010 | Babayoff |
| D618,619 S | 6/2010 | Walter |
| 7,728,848 B2 | 6/2010 | Petrov et al. |
| 7,731,508 B2 | 6/2010 | Borst |
| 7,735,217 B2 | 6/2010 | Borst |
| 7,740,476 B2 | 6/2010 | Rubbert et al. |
| 7,744,369 B2 | 6/2010 | Imgrund et al. |
| 7,746,339 B2 | 6/2010 | Matov et al. |
| 7,780,460 B2 | 8/2010 | Walter |
| 7,787,132 B2 | 8/2010 | Körner et al. |
| 7,791,810 B2 | 9/2010 | Powell |
| 7,796,243 B2 | 9/2010 | Choo-Smith et al. |
| 7,806,687 B2 | 10/2010 | Minagi et al. |
| 7,806,727 B2 | 10/2010 | Dold et al. |
| 7,813,787 B2 | 10/2010 | de Josselin de Jong et al. |
| 7,824,180 B2 | 11/2010 | Abolfathi et al. |
| 7,828,601 B2 | 11/2010 | Pyczak |
| 7,841,464 B2 | 11/2010 | Cinader et al. |
| 7,845,969 B2 | 12/2010 | Stadler et al. |
| 7,854,609 B2 | 12/2010 | Chen et al. |
| 7,862,336 B2 | 1/2011 | Kopelman et al. |
| 7,869,983 B2 | 1/2011 | Raby et al. |
| 7,872,760 B2 | 1/2011 | Ertl |
| 7,874,836 B2 | 1/2011 | McSurdy |
| 7,874,837 B2 | 1/2011 | Chishti et al. |
| 7,874,849 B2 | 1/2011 | Sticker et al. |
| 7,878,801 B2 | 2/2011 | Abolfathi et al. |
| 7,878,805 B2 | 2/2011 | Moss et al. |
| 7,880,751 B2 | 2/2011 | Kuo et al. |
| 7,892,474 B2 | 2/2011 | Shkolnik et al. |
| 7,904,308 B2 | 3/2011 | Arnone et al. |
| 7,907,280 B2 | 3/2011 | Johs et al. |
| 7,929,151 B2 | 4/2011 | Liang et al. |
| 7,930,189 B2 | 4/2011 | Kuo |
| 7,947,508 B2 | 5/2011 | Tricca et al. |
| 7,959,308 B2 | 6/2011 | Freeman et al. |
| 7,963,766 B2 | 6/2011 | Cronauer |
| 7,970,627 B2 | 6/2011 | Kuo et al. |
| 7,985,414 B2 | 7/2011 | Knaack et al. |
| 7,986,415 B2 | 7/2011 | Thiel et al. |
| 7,987,099 B2 | 7/2011 | Kuo et al. |
| 7,991,485 B2 | 8/2011 | Zakim |
| 8,017,891 B2 | 9/2011 | Nevin |
| 8,026,916 B2 | 9/2011 | Wen |
| 8,027,709 B2 | 9/2011 | Arnone et al. |
| 8,029,277 B2 | 10/2011 | Imgrund et al. |
| 8,038,444 B2 | 10/2011 | Kitching et al. |
| 8,045,772 B2 | 10/2011 | Kosuge et al. |
| 8,054,556 B2 | 11/2011 | Chen et al. |
| 8,070,490 B1 | 12/2011 | Roetzer et al. |
| 8,075,306 B2 | 12/2011 | Kitching et al. |
| 8,077,949 B2 | 12/2011 | Liang et al. |
| 8,083,556 B2 | 12/2011 | Stadler et al. |
| D652,799 S | 1/2012 | Mueller |
| 8,092,215 B2 | 1/2012 | Stone-Collonge et al. |
| 8,095,383 B2 | 1/2012 | Arnone et al. |
| 8,099,268 B2 | 1/2012 | Kitching et al. |
| 8,099,305 B2 | 1/2012 | Kuo et al. |
| 8,108,189 B2 | 1/2012 | Chelnokov et al. |
| 8,118,592 B2 | 2/2012 | Tortorici |
| 8,126,025 B2 | 2/2012 | Takeda |
| 8,136,529 B2 | 3/2012 | Kelly |
| 8,144,954 B2 | 3/2012 | Quadling et al. |
| 8,152,518 B2 | 4/2012 | Kuo |
| 8,160,334 B2 | 4/2012 | Thiel et al. |
| 8,172,569 B2 | 5/2012 | Matty et al. |
| 8,197,252 B1 | 6/2012 | Harrison |
| 8,201,560 B2 | 6/2012 | Dembro |
| 8,215,312 B2 | 7/2012 | Garabadian et al. |
| 8,240,018 B2 | 8/2012 | Walter et al. |
| 8,275,180 B2 | 9/2012 | Kuo |
| 8,279,450 B2 | 10/2012 | Oota et al. |
| 8,292,617 B2 | 10/2012 | Brandt et al. |
| 8,294,657 B2 | 10/2012 | Kim et al. |
| 8,296,952 B2 | 10/2012 | Greenberg |
| 8,297,286 B2 | 10/2012 | Smernoff |
| 8,306,608 B2 | 11/2012 | Mandelis et al. |
| 8,314,764 B2 | 11/2012 | Kim et al. |
| 8,332,015 B2 | 12/2012 | Ertl |
| 8,354,588 B2 | 1/2013 | Sticker et al. |
| 8,366,479 B2 | 2/2013 | Borst et al. |
| 8,401,826 B2 | 3/2013 | Cheng et al. |
| 8,419,428 B2 | 4/2013 | Lawrence |
| 8,433,083 B2 | 4/2013 | Abolfathi et al. |
| 8,439,672 B2 | 5/2013 | Matov et al. |
| 8,465,280 B2 | 6/2013 | Sachdeva et al. |
| 8,477,320 B2 | 7/2013 | Stock et al. |
| 8,488,113 B2 | 7/2013 | Thiel et al. |
| 8,517,726 B2 | 8/2013 | Kakavand et al. |
| 8,520,922 B2 | 8/2013 | Wang et al. |
| 8,520,925 B2 | 8/2013 | Duret et al. |
| 8,523,565 B2 | 9/2013 | Matty et al. |
| 8,545,221 B2 | 10/2013 | Stone-Collonge et al. |
| 8,556,625 B2 | 10/2013 | Lovely |
| 8,570,530 B2 | 10/2013 | Liang |
| 8,573,224 B2 | 11/2013 | Thornton |
| 8,577,212 B2 | 11/2013 | Thiel |
| 8,601,925 B1 | 12/2013 | Coto |
| 8,639,477 B2 | 1/2014 | Chelnokov et al. |
| 8,650,586 B2 | 2/2014 | Lee et al. |
| 8,675,706 B2 | 3/2014 | Seurin et al. |
| 8,723,029 B2 | 5/2014 | Pyczak et al. |
| 8,738,394 B2 | 5/2014 | Kuo |
| 8,743,923 B2 | 6/2014 | Geske et al. |
| 8,753,114 B2 | 6/2014 | Vuillemot |
| 8,767,270 B2 | 7/2014 | Curry et al. |
| 8,768,016 B2 | 7/2014 | Pan et al. |
| 8,771,149 B2 | 7/2014 | Rahman et al. |
| 8,839,476 B2 | 9/2014 | Adachi |
| 8,843,381 B2 | 9/2014 | Kuo et al. |
| 8,856,053 B2 | 10/2014 | Mah |
| 8,870,566 B2 | 10/2014 | Bergersen |
| 8,874,452 B2 | 10/2014 | Kuo |
| 8,878,905 B2 | 11/2014 | Fisker et al. |
| 8,899,976 B2 | 12/2014 | Chen et al. |
| 8,936,463 B2 | 1/2015 | Mason et al. |
| 8,944,812 B2 | 2/2015 | Kou |
| 8,948,482 B2 | 2/2015 | Levin |
| 8,956,058 B2 | 2/2015 | Rösch |
| 8,992,216 B2 | 3/2015 | Karazivan |
| 9,004,915 B2 | 4/2015 | Moss et al. |
| 9,022,792 B2 | 5/2015 | Sticker et al. |
| 9,039,418 B1 | 5/2015 | Rubbert |
| 9,084,535 B2 | 7/2015 | Girkin et al. |
| 9,084,657 B2 | 7/2015 | Matty et al. |
| 9,108,338 B2 | 8/2015 | Sirovskiy et al. |
| 9,144,512 B2 | 9/2015 | Wagner |

(56) References Cited

U.S. PATENT DOCUMENTS

| | | |
|---|---|---|
| 9,192,305 B2 | 11/2015 | Levin |
| 9,204,952 B2 | 12/2015 | Lampalzer |
| 9,211,166 B2 | 12/2015 | Kuo et al. |
| 9,214,014 B2 | 12/2015 | Levin |
| 9,220,580 B2 | 12/2015 | Borovinskih et al. |
| 9,241,774 B2 | 1/2016 | Li et al. |
| 9,242,118 B2 | 1/2016 | Brawn |
| 9,261,358 B2 | 2/2016 | Atiya et al. |
| 9,277,972 B2 | 3/2016 | Brandt et al. |
| 9,336,336 B2 | 5/2016 | Deichmann et al. |
| 9,351,810 B2 | 5/2016 | Moon |
| 9,375,300 B2 | 6/2016 | Matov et al. |
| 9,403,238 B2 | 8/2016 | Culp |
| 9,408,743 B1 | 8/2016 | Wagner |
| 9,414,897 B2 | 8/2016 | Wu et al. |
| 9,433,476 B2 | 9/2016 | Khardekar et al. |
| 9,439,568 B2 | 9/2016 | Atiya et al. |
| 9,444,981 B2 | 9/2016 | Bellis et al. |
| 9,463,287 B1 | 10/2016 | Lorberbaum et al. |
| 9,492,243 B2 | 11/2016 | Kuo |
| 9,500,635 B2 | 11/2016 | Islam |
| 9,506,808 B2 | 11/2016 | Jeon et al. |
| 9,510,918 B2 | 12/2016 | Sanchez |
| 9,545,331 B2 | 1/2017 | Ingemarsson-Matzen |
| 9,566,132 B2 | 2/2017 | Stone-Collonge et al. |
| 9,584,771 B2 | 2/2017 | Mandelis et al. |
| 9,589,329 B2 | 3/2017 | Levin |
| 9,675,427 B2 | 6/2017 | Kopelman |
| 9,675,430 B2 | 6/2017 | Verker et al. |
| 9,693,839 B2 | 7/2017 | Atiya et al. |
| 9,730,769 B2 | 8/2017 | Chen et al. |
| 9,744,006 B2 | 8/2017 | Ross |
| 9,820,829 B2 | 11/2017 | Kuo |
| 9,830,688 B2 | 11/2017 | Levin |
| 9,844,421 B2 | 12/2017 | Moss et al. |
| 9,848,985 B2 | 12/2017 | Yang et al. |
| 9,861,451 B1 | 1/2018 | Davis |
| 9,936,186 B2 | 4/2018 | Jesenko et al. |
| 10,123,706 B2 | 11/2018 | Elbaz et al. |
| 10,123,853 B2 | 11/2018 | Moss et al. |
| 10,154,889 B2 | 12/2018 | Chen et al. |
| 10,159,541 B2 | 12/2018 | Bindayel |
| 10,172,693 B2 | 1/2019 | Brandt et al. |
| 10,195,690 B2 | 2/2019 | Culp |
| 10,231,801 B2 | 3/2019 | Korytov et al. |
| 10,238,472 B2 | 3/2019 | Levin |
| 10,248,883 B2 | 4/2019 | Borovinskih et al. |
| 10,258,432 B2 | 4/2019 | Webber |
| 10,275,862 B2 | 4/2019 | Levin |
| 2001/0002310 A1 | 5/2001 | Chishti et al. |
| 2001/0032100 A1 | 10/2001 | Mahmud et al. |
| 2001/0038705 A1 | 11/2001 | Rubbert et al. |
| 2001/0041320 A1 | 11/2001 | Phan et al. |
| 2002/0004727 A1 | 1/2002 | Knaus et al. |
| 2002/0007284 A1 | 1/2002 | Schurenberg et al. |
| 2002/0010568 A1 | 1/2002 | Rubbert et al. |
| 2002/0015934 A1 | 2/2002 | Rubbert et al. |
| 2002/0025503 A1 | 2/2002 | Chapoulaud et al. |
| 2002/0026105 A1 | 2/2002 | Drazen |
| 2002/0028417 A1 | 3/2002 | Chapoulaud et al. |
| 2002/0035572 A1 | 3/2002 | Takatori et al. |
| 2002/0064752 A1 | 5/2002 | Durbin et al. |
| 2002/0064759 A1 | 5/2002 | Durbin et al. |
| 2002/0087551 A1 | 7/2002 | Hickey et al. |
| 2002/0107853 A1 | 8/2002 | Hofmann et al. |
| 2002/0188478 A1 | 12/2002 | Breeland et al. |
| 2002/0192617 A1 | 12/2002 | Phan et al. |
| 2003/0000927 A1 | 1/2003 | Kanaya et al. |
| 2003/0008259 A1 | 1/2003 | Kuo et al. |
| 2003/0009252 A1 | 1/2003 | Pavlovskaia et al. |
| 2003/0019848 A1 | 1/2003 | Nicholas et al. |
| 2003/0021453 A1 | 1/2003 | Weise et al. |
| 2003/0035061 A1 | 2/2003 | Iwaki et al. |
| 2003/0049581 A1 | 3/2003 | Deluke |
| 2003/0057192 A1 | 3/2003 | Patel |
| 2003/0059736 A1 | 3/2003 | Lai et al. |
| 2003/0060532 A1 | 3/2003 | Subelka et al. |
| 2003/0068598 A1 | 4/2003 | Vallittu et al. |
| 2003/0095697 A1 | 5/2003 | Wood et al. |
| 2003/0101079 A1 | 5/2003 | McLaughlin |
| 2003/0103060 A1 | 6/2003 | Anderson et al. |
| 2003/0120517 A1 | 6/2003 | Eida et al. |
| 2003/0139834 A1 | 7/2003 | Nikolskiy et al. |
| 2003/0144886 A1 | 7/2003 | Taira |
| 2003/0172043 A1 | 9/2003 | Guyon et al. |
| 2003/0190575 A1 | 10/2003 | Hilliard |
| 2003/0192867 A1 | 10/2003 | Yamazaki et al. |
| 2003/0207224 A1 | 11/2003 | Lotte |
| 2003/0211440 A1 | 11/2003 | Kuo et al. |
| 2003/0215764 A1 | 11/2003 | Kopelman et al. |
| 2003/0224311 A1 | 12/2003 | Cronauer |
| 2003/0224313 A1 | 12/2003 | Bergersen |
| 2003/0224314 A1 | 12/2003 | Bergersen |
| 2004/0002873 A1 | 1/2004 | Sachdeva |
| 2004/0009449 A1 | 1/2004 | Mah et al. |
| 2004/0013994 A1 | 1/2004 | Goldberg et al. |
| 2004/0019262 A1 | 1/2004 | Perelgut |
| 2004/0029078 A1 | 2/2004 | Marshall |
| 2004/0038168 A1 | 2/2004 | Choi et al. |
| 2004/0054304 A1 | 3/2004 | Raby |
| 2004/0054358 A1 | 3/2004 | Cox et al. |
| 2004/0058295 A1 | 3/2004 | Bergersen |
| 2004/0068199 A1 | 4/2004 | Echauz et al. |
| 2004/0078222 A1 | 4/2004 | Khan et al. |
| 2004/0080621 A1 | 4/2004 | Fisher et al. |
| 2004/0094165 A1 | 5/2004 | Cook |
| 2004/0107118 A1 | 6/2004 | Harnsberger et al. |
| 2004/0133083 A1 | 7/2004 | Comaniciu et al. |
| 2004/0152036 A1 | 8/2004 | Abolfathi |
| 2004/0158194 A1 | 8/2004 | Wolff et al. |
| 2004/0166463 A1 | 8/2004 | Wen et al. |
| 2004/0167646 A1 | 8/2004 | Jelonek et al. |
| 2004/0170941 A1 | 9/2004 | Phan et al. |
| 2004/0193036 A1 | 9/2004 | Zhou et al. |
| 2004/0197728 A1 | 10/2004 | Abolfathi et al. |
| 2004/0214128 A1 | 10/2004 | Sachdeva et al. |
| 2004/0219479 A1 | 11/2004 | Malin et al. |
| 2004/0220691 A1 | 11/2004 | Hofmeister et al. |
| 2004/0229185 A1 | 11/2004 | Knopp |
| 2004/0259049 A1 | 12/2004 | Kopelman et al. |
| 2005/0003318 A1 | 1/2005 | Choi et al. |
| 2005/0003319 A1* | 1/2005 | Kuo ............... A61C 7/08 433/6 |
| 2005/0023356 A1 | 2/2005 | Wiklof et al. |
| 2005/0031196 A1 | 2/2005 | Moghaddam et al. |
| 2005/0037312 A1 | 2/2005 | Uchida |
| 2005/0038669 A1 | 2/2005 | Sachdeva et al. |
| 2005/0040551 A1 | 2/2005 | Biegler et al. |
| 2005/0042569 A1 | 2/2005 | Plan et al. |
| 2005/0042577 A1 | 2/2005 | Kvitrud et al. |
| 2005/0048433 A1 | 3/2005 | Hilliard |
| 2005/0074717 A1 | 4/2005 | Cleary et al. |
| 2005/0089822 A1 | 4/2005 | Geng |
| 2005/0100333 A1 | 5/2005 | Kerschbaumer et al. |
| 2005/0108052 A1 | 5/2005 | Omaboe |
| 2005/0131738 A1 | 6/2005 | Morris |
| 2005/0144150 A1 | 6/2005 | Ramamurthy et al. |
| 2005/0171594 A1 | 8/2005 | Machan et al. |
| 2005/0171630 A1 | 8/2005 | Dinauer et al. |
| 2005/0181333 A1 | 8/2005 | Karazivan et al. |
| 2005/0186524 A1 | 8/2005 | Abolfathi et al. |
| 2005/0186526 A1 | 8/2005 | Stewart et al. |
| 2005/0216314 A1 | 9/2005 | Secor |
| 2005/0233276 A1 | 10/2005 | Kopelman et al. |
| 2005/0239013 A1 | 10/2005 | Sachdeva |
| 2005/0244781 A1 | 11/2005 | Abels et al. |
| 2005/0244791 A1 | 11/2005 | Davis et al. |
| 2005/0271996 A1 | 12/2005 | Sporbert et al. |
| 2006/0056670 A1 | 3/2006 | Hamadeh |
| 2006/0057533 A1 | 3/2006 | McGann |
| 2006/0063135 A1 | 3/2006 | Mehl |
| 2006/0078842 A1 | 4/2006 | Sachdeva et al. |
| 2006/0084024 A1 | 4/2006 | Farrell |
| 2006/0093982 A1 | 5/2006 | Wen |

(56) References Cited

U.S. PATENT DOCUMENTS

| | | |
|---|---|---|
| 2006/0098007 A1 | 5/2006 | Rouet et al. |
| 2006/0099545 A1 | 5/2006 | Lia et al. |
| 2006/0099546 A1 | 5/2006 | Bergersen |
| 2006/0110698 A1 | 5/2006 | Robson |
| 2006/0111631 A1 | 5/2006 | Kelliher et al. |
| 2006/0115782 A1 | 6/2006 | Li et al. |
| 2006/0115785 A1 | 6/2006 | Li et al. |
| 2006/0137813 A1 | 6/2006 | Robrecht et al. |
| 2006/0147872 A1 | 7/2006 | Andreiko |
| 2006/0154198 A1 | 7/2006 | Durbin et al. |
| 2006/0154207 A1 | 7/2006 | Kuo |
| 2006/0173715 A1 | 8/2006 | Wang |
| 2006/0183082 A1 | 8/2006 | Quadling et al. |
| 2006/0188834 A1 | 8/2006 | Hilliard |
| 2006/0188848 A1 | 8/2006 | Tricca et al. |
| 2006/0194163 A1 | 8/2006 | Tricca et al. |
| 2006/0199153 A1 | 9/2006 | Liu et al. |
| 2006/0204078 A1 | 9/2006 | Orth et al. |
| 2006/0223022 A1 | 10/2006 | Solomon |
| 2006/0223023 A1 | 10/2006 | Lai et al. |
| 2006/0223032 A1 | 10/2006 | Fried et al. |
| 2006/0223342 A1 | 10/2006 | Borst et al. |
| 2006/0234179 A1 | 10/2006 | Wen et al. |
| 2006/0257815 A1 | 11/2006 | De Dominicis |
| 2006/0275729 A1 | 12/2006 | Fornoff |
| 2006/0275731 A1 | 12/2006 | Wen et al. |
| 2006/0275736 A1 | 12/2006 | Wen et al. |
| 2006/0277075 A1 | 12/2006 | Salwan |
| 2006/0290693 A1 | 12/2006 | Zhou et al. |
| 2006/0292520 A1 | 12/2006 | Dillon et al. |
| 2007/0031775 A1 | 2/2007 | Andreiko |
| 2007/0046865 A1 | 3/2007 | Umeda et al. |
| 2007/0053048 A1 | 3/2007 | Kumar et al. |
| 2007/0054237 A1 | 3/2007 | Neuschafer |
| 2007/0065768 A1 | 3/2007 | Nadav |
| 2007/0087300 A1 | 4/2007 | Willison et al. |
| 2007/0087302 A1 | 4/2007 | Reising et al. |
| 2007/0106138 A1 | 5/2007 | Beiski et al. |
| 2007/0122592 A1 | 5/2007 | Anderson et al. |
| 2007/0128574 A1 | 6/2007 | Kuo et al. |
| 2007/0141525 A1 | 6/2007 | Cinader, Jr. |
| 2007/0141526 A1 | 6/2007 | Eisenberg et al. |
| 2007/0143135 A1 | 6/2007 | Lindquist et al. |
| 2007/0168152 A1 | 7/2007 | Matov et al. |
| 2007/0172112 A1 | 7/2007 | Paley et al. |
| 2007/0172291 A1 | 7/2007 | Yokoyama |
| 2007/0178420 A1 | 8/2007 | Keski-Nisula et al. |
| 2007/0183633 A1 | 8/2007 | Hoffmann |
| 2007/0184402 A1 | 8/2007 | Boutoussov et al. |
| 2007/0185732 A1 | 8/2007 | Hicks et al. |
| 2007/0192137 A1 | 8/2007 | Ombrellaro |
| 2007/0199929 A1 | 8/2007 | Rippl et al. |
| 2007/0207434 A1 | 9/2007 | Kuo et al. |
| 2007/0215582 A1 | 9/2007 | Roeper et al. |
| 2007/0218422 A1 | 9/2007 | Ehrenfeld |
| 2007/0231765 A1 | 10/2007 | Phan et al. |
| 2007/0238065 A1 | 10/2007 | Sherwood et al. |
| 2007/0239488 A1 | 10/2007 | DeRosso |
| 2007/0263226 A1 | 11/2007 | Kurtz et al. |
| 2008/0013727 A1 | 1/2008 | Uemura |
| 2008/0020350 A1 | 1/2008 | Matov et al. |
| 2008/0045053 A1 | 2/2008 | Stadler et al. |
| 2008/0057461 A1 | 3/2008 | Cheng et al. |
| 2008/0057467 A1 | 3/2008 | Gittelson |
| 2008/0057479 A1 | 3/2008 | Grenness |
| 2008/0059238 A1 | 3/2008 | Park et al. |
| 2008/0090208 A1 | 4/2008 | Rubbert |
| 2008/0094389 A1 | 4/2008 | Rouet et al. |
| 2008/0113317 A1 | 5/2008 | Kemp et al. |
| 2008/0115791 A1 | 5/2008 | Heine |
| 2008/0118882 A1 | 5/2008 | Su |
| 2008/0118886 A1 | 5/2008 | Liang et al. |
| 2008/0141534 A1 | 6/2008 | Hilliard |
| 2008/0169122 A1 | 7/2008 | Shiraishi et al. |
| 2008/0171934 A1 | 7/2008 | Greenan et al. |
| 2008/0176448 A1 | 7/2008 | Muller et al. |
| 2008/0233530 A1 | 9/2008 | Cinader |
| 2008/0242144 A1 | 10/2008 | Dietz |
| 2008/0248443 A1 | 10/2008 | Chishti et al. |
| 2008/0254403 A1 | 10/2008 | Hilliard |
| 2008/0268400 A1 | 10/2008 | Moss et al. |
| 2008/0306724 A1 | 12/2008 | Kitching et al. |
| 2009/0029310 A1 | 1/2009 | Pumphrey et al. |
| 2009/0030290 A1 | 1/2009 | Kozuch et al. |
| 2009/0030347 A1 | 1/2009 | Cao |
| 2009/0040740 A1 | 2/2009 | Muller et al. |
| 2009/0061379 A1 | 3/2009 | Yamamoto et al. |
| 2009/0061381 A1 | 3/2009 | Durbin et al. |
| 2009/0075228 A1 | 3/2009 | Kumada et al. |
| 2009/0087050 A1 | 4/2009 | Gandyra |
| 2009/0098502 A1 | 4/2009 | Andreiko |
| 2009/0099445 A1 | 4/2009 | Burger |
| 2009/0103579 A1 | 4/2009 | Ushimaru et al. |
| 2009/0105523 A1 | 4/2009 | Kassayan et al. |
| 2009/0130620 A1 | 5/2009 | Yazdi et al. |
| 2009/0136890 A1 | 5/2009 | Kang et al. |
| 2009/0136893 A1 | 5/2009 | Zegarelli |
| 2009/0148809 A1 | 6/2009 | Kuo et al. |
| 2009/0170050 A1 | 7/2009 | Marcus |
| 2009/0181346 A1 | 7/2009 | Orth |
| 2009/0191502 A1 | 7/2009 | Cao et al. |
| 2009/0210032 A1 | 8/2009 | Beiski et al. |
| 2009/0218514 A1 | 9/2009 | Klunder et al. |
| 2009/0281433 A1 | 11/2009 | Saadat et al. |
| 2009/0286195 A1 | 11/2009 | Sears et al. |
| 2009/0298017 A1 | 12/2009 | Boerjes et al. |
| 2009/0305540 A1 | 12/2009 | Stadler et al. |
| 2009/0316966 A1 | 12/2009 | Marshall et al. |
| 2009/0317757 A1 | 12/2009 | Lemchen |
| 2010/0015565 A1 | 1/2010 | Carrillo Gonzalez et al. |
| 2010/0019170 A1 | 1/2010 | Hart et al. |
| 2010/0028825 A1 | 2/2010 | Lemchen |
| 2010/0045902 A1 | 2/2010 | Ikeda et al. |
| 2010/0062394 A1 | 3/2010 | Jones et al. |
| 2010/0068676 A1 | 3/2010 | Mason et al. |
| 2010/0138025 A1 | 6/2010 | Morton et al. |
| 2010/0142789 A1 | 6/2010 | Chang et al. |
| 2010/0145664 A1 | 6/2010 | Hultgren et al. |
| 2010/0145898 A1 | 6/2010 | Malfliet et al. |
| 2010/0152599 A1 | 6/2010 | DuHamel et al. |
| 2010/0165275 A1 | 7/2010 | Tsukamoto et al. |
| 2010/0167225 A1 | 7/2010 | Kuo |
| 2010/0179789 A1 | 7/2010 | Sachdeva et al. |
| 2010/0193482 A1 | 8/2010 | Ow et al. |
| 2010/0196837 A1 | 8/2010 | Farrell |
| 2010/0216085 A1 | 8/2010 | Kopelman |
| 2010/0217130 A1 | 8/2010 | Weinlaender |
| 2010/0231577 A1 | 9/2010 | Kim et al. |
| 2010/0268363 A1 | 10/2010 | Karim et al. |
| 2010/0268515 A1 | 10/2010 | Vogt et al. |
| 2010/0279243 A1 | 11/2010 | Cinader et al. |
| 2010/0280798 A1 | 11/2010 | Pattijn |
| 2010/0281370 A1 | 11/2010 | Rohaly et al. |
| 2010/0303316 A1 | 12/2010 | Bullis et al. |
| 2010/0312484 A1 | 12/2010 | DuHamel et al. |
| 2010/0327461 A1 | 12/2010 | Co et al. |
| 2011/0007920 A1 | 1/2011 | Abolfathi et al. |
| 2011/0012901 A1 | 1/2011 | Kaplanyan |
| 2011/0045428 A1 | 2/2011 | Boltunov et al. |
| 2011/0056350 A1 | 3/2011 | Gale et al. |
| 2011/0065060 A1 | 3/2011 | Teixeira et al. |
| 2011/0081625 A1 | 4/2011 | Fuh |
| 2011/0091832 A1 | 4/2011 | Kim et al. |
| 2011/0102549 A1 | 5/2011 | Takahashi |
| 2011/0102566 A1 | 5/2011 | Zakian et al. |
| 2011/0104630 A1 | 5/2011 | Matov et al. |
| 2011/0136072 A1 | 6/2011 | Li et al. |
| 2011/0136990 A1 | 6/2011 | Kazemi |
| 2011/0143300 A1 | 6/2011 | Villalba |
| 2011/0143673 A1 | 6/2011 | Landesman et al. |
| 2011/0159452 A1 | 6/2011 | Huang |
| 2011/0164810 A1 | 7/2011 | Zang et al. |
| 2011/0207072 A1 | 8/2011 | Schiemann |
| 2011/0212420 A1 | 9/2011 | Vuillemot |

(56) References Cited

U.S. PATENT DOCUMENTS

| | | |
|---|---|---|
| 2011/0220623 A1 | 9/2011 | Beutler |
| 2011/0235045 A1 | 9/2011 | Koerner et al. |
| 2011/0269092 A1 | 11/2011 | Kuo et al. |
| 2011/0316994 A1 | 12/2011 | Lemchen |
| 2012/0028210 A1 | 2/2012 | Hegyi et al. |
| 2012/0029883 A1 | 2/2012 | Heinz et al. |
| 2012/0040311 A1 | 2/2012 | Nilsson |
| 2012/0064477 A1 | 3/2012 | Schmitt |
| 2012/0081786 A1 | 4/2012 | Mizuyama et al. |
| 2012/0086681 A1 | 4/2012 | Kim et al. |
| 2012/0115107 A1 | 5/2012 | Adams |
| 2012/0129117 A1 | 5/2012 | McCance |
| 2012/0147912 A1 | 6/2012 | Moench et al. |
| 2012/0150494 A1 | 6/2012 | Anderson et al. |
| 2012/0166213 A1 | 6/2012 | Arnone et al. |
| 2012/0172678 A1 | 7/2012 | Logan et al. |
| 2012/0281293 A1 | 11/2012 | Gronenborn et al. |
| 2012/0295216 A1 | 11/2012 | Dykes et al. |
| 2012/0322025 A1 | 12/2012 | Ozawa et al. |
| 2013/0029284 A1 | 1/2013 | Teasdale |
| 2013/0081272 A1 | 4/2013 | Johnson et al. |
| 2013/0089828 A1 | 4/2013 | Borovinskih et al. |
| 2013/0095446 A1 | 4/2013 | Andreiko et al. |
| 2013/0103176 A1 | 4/2013 | Kopelman et al. |
| 2013/0110469 A1 | 5/2013 | Kopelman |
| 2013/0150689 A1 | 6/2013 | Shaw-Klein |
| 2013/0163627 A1 | 6/2013 | Seurin et al. |
| 2013/0201488 A1 | 8/2013 | Ishihara |
| 2013/0204599 A1 | 8/2013 | Matov et al. |
| 2013/0209952 A1 | 8/2013 | Kuo et al. |
| 2013/0235165 A1 | 9/2013 | Gharib et al. |
| 2013/0252195 A1 | 9/2013 | Popat |
| 2013/0266326 A1 | 10/2013 | Joseph et al. |
| 2013/0278396 A1 | 10/2013 | Kimmel |
| 2013/0280671 A1 | 10/2013 | Brawn et al. |
| 2013/0286174 A1 | 10/2013 | Urakabe |
| 2013/0293824 A1 | 11/2013 | Yoneyama et al. |
| 2013/0323664 A1 | 12/2013 | Parker |
| 2013/0323671 A1 | 12/2013 | Dillon et al. |
| 2013/0323674 A1 | 12/2013 | Hakomori et al. |
| 2013/0325431 A1 | 12/2013 | See et al. |
| 2013/0337412 A1 | 12/2013 | Kwon |
| 2014/0061974 A1 | 3/2014 | Tyler |
| 2014/0081091 A1 | 3/2014 | Abolfathi et al. |
| 2014/0093160 A1 | 4/2014 | Porikli et al. |
| 2014/0106289 A1 | 4/2014 | Kozlowski |
| 2014/0122027 A1 | 5/2014 | Andreiko et al. |
| 2014/0136222 A1 | 5/2014 | Arnone et al. |
| 2014/0142902 A1 | 5/2014 | Chelnokov et al. |
| 2014/0178829 A1 | 6/2014 | Kim |
| 2014/0265034 A1 | 9/2014 | Dudley |
| 2014/0272774 A1 | 9/2014 | Dillon et al. |
| 2014/0280376 A1 | 9/2014 | Kuo |
| 2014/0294273 A1 | 10/2014 | Jaisson |
| 2014/0313299 A1 | 10/2014 | Gebhardt et al. |
| 2014/0329194 A1 | 11/2014 | Sachdeva et al. |
| 2014/0342301 A1 | 11/2014 | Fleer et al. |
| 2014/0350354 A1* | 11/2014 | Stenzler ............... A61F 5/566 600/301 |
| 2014/0363778 A1 | 12/2014 | Parker |
| 2015/0002649 A1 | 1/2015 | Nowak et al. |
| 2015/0004553 A1 | 1/2015 | Li et al. |
| 2015/0021210 A1 | 1/2015 | Kesling |
| 2015/0079531 A1 | 3/2015 | Heine |
| 2015/0094564 A1 | 4/2015 | Tashman et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0132708 A1 | 5/2015 | Kuo |
| 2015/0140502 A1 | 5/2015 | Brawn et al. |
| 2015/0150501 A1 | 6/2015 | George et al. |
| 2015/0164335 A1 | 6/2015 | Van Der Poel et al. |
| 2015/0173856 A1 | 6/2015 | Iowe et al. |
| 2015/0182303 A1 | 7/2015 | Abraham et al. |
| 2015/0216626 A1 | 8/2015 | Ranjbar |
| 2015/0216716 A1 | 8/2015 | Anitua Aldecoa |
| 2015/0230885 A1 | 8/2015 | Wucher |
| 2015/0238280 A1 | 8/2015 | Wu et al. |
| 2015/0238283 A1 | 8/2015 | Tanugula et al. |
| 2015/0306486 A1 | 10/2015 | Logan et al. |
| 2015/0320320 A1 | 11/2015 | Kopelman et al. |
| 2015/0320532 A1 | 11/2015 | Matty et al. |
| 2015/0325044 A1 | 11/2015 | Lebovitz |
| 2015/0338209 A1 | 11/2015 | Knüttel |
| 2015/0351638 A1 | 12/2015 | Amato |
| 2015/0374469 A1 | 12/2015 | Konno et al. |
| 2016/0000332 A1 | 1/2016 | Atiya et al. |
| 2016/0003610 A1 | 1/2016 | Lampert et al. |
| 2016/0022185 A1 | 1/2016 | Agarwal et al. |
| 2016/0042509 A1 | 2/2016 | Andreiko et al. |
| 2016/0051345 A1 | 2/2016 | Levin |
| 2016/0064898 A1 | 3/2016 | Atiya et al. |
| 2016/0067013 A1 | 3/2016 | Morton et al. |
| 2016/0081768 A1 | 3/2016 | Kopelman et al. |
| 2016/0081769 A1 | 3/2016 | Kimura et al. |
| 2016/0095668 A1 | 4/2016 | Kuo et al. |
| 2016/0100924 A1* | 4/2016 | Wilson ................... H02J 50/10 206/63.5 |
| 2016/0106520 A1 | 4/2016 | Borovinskih et al. |
| 2016/0120621 A1 | 5/2016 | Li et al. |
| 2016/0135924 A1 | 5/2016 | Choi et al. |
| 2016/0135925 A1 | 5/2016 | Mason et al. |
| 2016/0163115 A1 | 6/2016 | Furst |
| 2016/0217708 A1 | 7/2016 | Levin et al. |
| 2016/0220105 A1 | 8/2016 | Durent |
| 2016/0220200 A1 | 8/2016 | Sandholm et al. |
| 2016/0225151 A1 | 8/2016 | Cocco et al. |
| 2016/0228213 A1 | 8/2016 | Tod et al. |
| 2016/0242871 A1 | 8/2016 | Morton et al. |
| 2016/0246936 A1 | 8/2016 | Kahn |
| 2016/0287358 A1 | 10/2016 | Nowak et al. |
| 2016/0296303 A1 | 10/2016 | Parker |
| 2016/0302885 A1 | 10/2016 | Matov et al. |
| 2016/0328843 A1 | 11/2016 | Graham et al. |
| 2016/0338799 A1 | 11/2016 | Wu et al. |
| 2016/0346063 A1 | 12/2016 | Schulhof et al. |
| 2016/0367188 A1 | 12/2016 | Malik et al. |
| 2016/0367339 A1 | 12/2016 | Khardekar et al. |
| 2017/0007365 A1 | 1/2017 | Kopelman et al. |
| 2017/0007366 A1 | 1/2017 | Kopelman et al. |
| 2017/0007367 A1 | 1/2017 | Li et al. |
| 2017/0007368 A1 | 1/2017 | Boronkay |
| 2017/0020633 A1 | 1/2017 | Stone-Collonge et al. |
| 2017/0049326 A1 | 2/2017 | Alfano et al. |
| 2017/0056131 A1 | 3/2017 | Alauddin et al. |
| 2017/0071705 A1 | 3/2017 | Kuo |
| 2017/0086943 A1 | 3/2017 | Mah |
| 2017/0100209 A1 | 4/2017 | Wen |
| 2017/0100212 A1 | 4/2017 | Sherwood et al. |
| 2017/0100213 A1 | 4/2017 | Kuo |
| 2017/0100214 A1 | 4/2017 | Wen |
| 2017/0105815 A1 | 4/2017 | Matov et al. |
| 2017/0135792 A1 | 5/2017 | Webber |
| 2017/0135793 A1 | 5/2017 | Webber et al. |
| 2017/0156821 A1 | 6/2017 | Kopelman et al. |
| 2017/0165032 A1 | 6/2017 | Webber et al. |
| 2017/0215739 A1 | 8/2017 | Miyasato |
| 2017/0251954 A1 | 9/2017 | Lotan et al. |
| 2017/0258555 A1 | 9/2017 | Kopelman |
| 2017/0265970 A1 | 9/2017 | Verker |
| 2017/0319054 A1 | 11/2017 | Miller et al. |
| 2017/0319296 A1 | 11/2017 | Webber et al. |
| 2017/0325690 A1 | 11/2017 | Salah et al. |
| 2017/0340411 A1 | 11/2017 | Akselrod |
| 2017/0340415 A1 | 11/2017 | Choi et al. |
| 2018/0000563 A1 | 1/2018 | Shanjani et al. |
| 2018/0000565 A1 | 1/2018 | Shanjani et al. |
| 2018/0028064 A1 | 2/2018 | Elbaz et al. |
| 2018/0028065 A1 | 2/2018 | Elbaz et al. |
| 2018/0055602 A1 | 3/2018 | Kopelman et al. |
| 2018/0071054 A1 | 3/2018 | Ha |
| 2018/0071055 A1 | 3/2018 | Kuo |
| 2018/0085059 A1 | 3/2018 | Lee |
| 2018/0125610 A1 | 5/2018 | Carrier et al. |

(56) References Cited

U.S. PATENT DOCUMENTS

| | | |
|---|---|---|
| 2018/0153648 A1 | 6/2018 | Shanjani et al. |
| 2018/0153649 A1 | 6/2018 | Wu et al. |
| 2018/0153733 A1 | 6/2018 | Kuo |
| 2018/0168788 A1 | 6/2018 | Fernie |
| 2018/0192877 A1 | 7/2018 | Atiya et al. |
| 2018/0228359 A1 | 8/2018 | Meyer et al. |
| 2018/0280118 A1 | 10/2018 | Cramer |
| 2018/0284727 A1 | 10/2018 | Cramer et al. |
| 2018/0318043 A1 | 11/2018 | Li et al. |
| 2018/0353264 A1 | 12/2018 | Riley et al. |
| 2018/0360567 A1 | 12/2018 | Xue et al. |
| 2018/0368944 A1 | 12/2018 | Sato et al. |
| 2018/0368961 A1 | 12/2018 | Shanjani et al. |
| 2019/0019187 A1 | 1/2019 | Miller et al. |
| 2019/0021817 A1 | 1/2019 | Sato et al. |
| 2019/0026599 A1 | 1/2019 | Salah et al. |
| 2019/0029522 A1 | 1/2019 | Sato et al. |
| 2019/0029784 A1 | 1/2019 | Moalem et al. |
| 2019/0046296 A1 | 2/2019 | Kopelman et al. |
| 2019/0046297 A1 | 2/2019 | Kopelman et al. |
| 2019/0076026 A1 | 3/2019 | Elbaz et al. |
| 2019/0076214 A1 | 3/2019 | Nyukhtikov et al. |
| 2019/0076216 A1 | 3/2019 | Moss et al. |
| 2019/0090983 A1 | 3/2019 | Webber et al. |
| 2019/0095539 A1 | 3/2019 | Elbaz et al. |
| 2019/0099129 A1 | 4/2019 | Kopelman et al. |
| 2019/0105130 A1 | 4/2019 | Grove et al. |
| 2019/0125494 A1 | 5/2019 | Li et al. |

FOREIGN PATENT DOCUMENTS

| | | |
|---|---|---|
| CA | 1121955 A1 | 4/1982 |
| CN | 1655732 A | 8/2005 |
| CN | 1655733 A | 8/2005 |
| CN | 1867317 A | 11/2006 |
| CN | 102017658 A | 4/2011 |
| CN | 103889364 A | 6/2014 |
| CN | 204092220 U | 1/2015 |
| CN | 105496575 A | 4/2016 |
| CN | 105997274 A | 10/2016 |
| DE | 2749802 A1 | 5/1978 |
| DE | 3526198 A1 | 2/1986 |
| DE | 4207169 A1 | 9/1993 |
| DE | 69327661 T2 | 7/2000 |
| DE | 102005043627 A1 | 3/2007 |
| DE | 202010017014 U1 | 3/2011 |
| DE | 102011051443 A1 | 1/2013 |
| DE | 202012011899 U1 | 1/2013 |
| DE | 102014225457 A1 | 6/2016 |
| EP | 0428152 A1 | 5/1991 |
| EP | 490848 A2 | 6/1992 |
| EP | 541500 A1 | 5/1993 |
| EP | 714632 B1 | 5/1997 |
| EP | 774933 B1 | 12/2000 |
| EP | 731673 B1 | 5/2001 |
| EP | 1941843 A2 | 7/2008 |
| EP | 2437027 A2 | 4/2012 |
| EP | 2447754 A1 | 5/2012 |
| EP | 1989764 B1 | 7/2012 |
| EP | 2332221 B1 | 11/2012 |
| EP | 2596553 B1 | 12/2013 |
| EP | 2612300 B1 | 2/2015 |
| EP | 2848229 A1 | 3/2015 |
| ES | 463897 A1 | 1/1980 |
| ES | 2455066 A1 | 4/2014 |
| FR | 2369828 A1 | 6/1978 |
| FR | 2867377 A1 | 9/2005 |
| FR | 2930334 A1 | 10/2009 |
| GB | 1550777 A | 8/1979 |
| JP | 53-058191 A | 5/1978 |
| JP | 04-028359 A | 1/1992 |
| JP | 08-508174 A | 9/1996 |
| JP | 09-19443 A | 1/1997 |
| JP | 2003245289 A | 9/2003 |
| JP | 2000339468 A | 9/2004 |
| JP | 2005527320 A | 9/2005 |
| JP | 2005527321 A | 9/2005 |
| JP | 2006043121 A | 2/2006 |
| JP | 2007151614 A | 6/2007 |
| JP | 2007260158 A | 10/2007 |
| JP | 2007537824 A | 12/2007 |
| JP | 2008067732 A | 3/2008 |
| JP | 2008523370 A | 7/2008 |
| JP | 04184427 B1 | 11/2008 |
| JP | 2009000412 A | 1/2009 |
| JP | 2009018173 A | 1/2009 |
| JP | 2009078133 A | 4/2009 |
| JP | 2009101386 A | 5/2009 |
| JP | 2009205330 A | 9/2009 |
| JP | 2010017726 A | 1/2010 |
| JP | 2011087733 A | 5/2011 |
| JP | 2012045143 A | 3/2012 |
| JP | 2013007645 A | 1/2013 |
| JP | 2013192865 A | 9/2013 |
| JP | 201735173 A | 2/2017 |
| KR | 10-20020062793 A | 7/2002 |
| KR | 10-20070108019 A | 11/2007 |
| KR | 10-20090065778 A | 6/2009 |
| KR | 10-1266966 B1 | 5/2013 |
| KR | 10-2016-041632 A | 4/2016 |
| KR | 10-2016-0071127 A | 6/2016 |
| KR | 10-1675089 B1 | 11/2016 |
| TW | 480166 B | 3/2002 |
| WO | WO91/004713 A1 | 4/1991 |
| WO | WO92/03102 A1 | 3/1992 |
| WO | WO94/010935 A1 | 5/1994 |
| WO | WO96/23452 A1 | 8/1996 |
| WO | WO-9712299 A1 * | 4/1997 ............... A61C 7/06 |
| WO | WO98/032394 A1 | 7/1998 |
| WO | WO98/044865 A1 | 10/1998 |
| WO | WO01/08592 A1 | 2/2001 |
| WO | WO01/85047 A2 | 11/2001 |
| WO | WO02/017776 A2 | 3/2002 |
| WO | WO02/024100 A1 | 3/2002 |
| WO | WO02/058583 A1 | 8/2002 |
| WO | WO02/062252 A1 | 8/2002 |
| WO | WO02/095475 A1 | 11/2002 |
| WO | WO03/003932 A2 | 1/2003 |
| WO | WO2005/114183 A1 | 12/2005 |
| WO | WO2006/096558 A2 | 9/2006 |
| WO | WO2006/100700 A1 | 9/2006 |
| WO | WO2006/133548 A1 | 12/2006 |
| WO | WO2007/019709 A2 | 2/2007 |
| WO | WO2007/071341 A1 | 6/2007 |
| WO | WO2007/103377 A2 | 9/2007 |
| WO | WO2008/115654 A1 | 9/2008 |
| WO | WO2009/016645 A2 | 2/2009 |
| WO | WO2009/085752 A2 | 7/2009 |
| WO | WO2009/089129 A1 | 7/2009 |
| WO | WO2009/146788 A1 | 12/2009 |
| WO | WO2009/146789 A1 | 12/2009 |
| WO | WO2010/059988 A1 | 5/2010 |
| WO | WO2010/123892 A2 | 10/2010 |
| WO | WO2012/007003 A1 | 1/2012 |
| WO | WO2012/064684 A2 | 5/2012 |
| WO | WO2012/074304 A2 | 6/2012 |
| WO | WO2012/078980 A2 | 6/2012 |
| WO | WO2012/083968 A1 | 6/2012 |
| WO | WO2012/140021 A2 | 10/2012 |
| WO | WO2013/058879 A2 | 4/2013 |
| WO | WO2014/068107 A1 | 5/2014 |
| WO | WO2014/091865 A1 | 6/2014 |
| WO | WO2014/143911 A1 | 9/2014 |
| WO | WO2015/015289 A2 | 2/2015 |
| WO | WO2015/063032 A1 | 5/2015 |
| WO | WO2015/112638 A1 | 7/2015 |
| WO | WO2015/176004 A1 | 11/2015 |
| WO | WO2016/004415 A1 | 1/2016 |
| WO | WO2016/042393 A1 | 3/2016 |
| WO | WO2016/061279 A1 | 4/2016 |
| WO | WO2016/084066 A1 | 6/2016 |
| WO | WO2016/099471 A1 | 6/2016 |
| WO | WO2016/113745 A1 | 7/2016 |
| WO | WO2016/116874 A1 | 7/2016 |

(56) References Cited

FOREIGN PATENT DOCUMENTS

| WO | WO2016/200177 A1 | 12/2016 |
| --- | --- | --- |
| WO | WO2017/006176 A1 | 1/2017 |
| WO | WO2017/182654 A1 | 10/2017 |
| WO | WO2018/057547 A1 | 3/2018 |
| WO | WO2018/085718 A2 | 5/2018 |
| WO | WO2018/232113 A1 | 12/2018 |
| WO | WO2019/018784 A1 | 1/2019 |

OTHER PUBLICATIONS

AADR. American Association for Dental Research; Summary of Activities; Los Angeles, CA; p. 195; Mar. 20-23,(year of pub. sufficiently earlier than effective US filed and any foreign priority date) 1980.

Alcaniz et aL; An Advanced System for the Simulation and Planning of Orthodontic Treatments; Karl Heinz Hohne and Ron Kikinis (eds.); Visualization in Biomedical Computing, 4th Intl. Conf, VBC '96, Hamburg, Germany; Springer-Verlag; pp. 511-520; Sep. 22-25, 1996.

Alexander et al.; The DigiGraph Work Station Part 2 Clinical Management; J. Clin. Orthod.; pp. 402-407; (Author Manuscript); Jul. 1990.

Align Technology; Align technology announces new teen solution with introduction of invisalign teen with mandibular advancement; 2 pages; retrieved from the internet (http://investor.aligntech.com/static-files/eb4fa6bb-3e62-404f-b74d-32059366a01b); Mar. 6, 2017.

Allesee Orthodontic Appliance: Important Tip About Wearing the Red White & Blue Active Clear Retainer System; Allesee Orthodontic Appliances—Pro Lab; 1 page; (year of pub. sufficiently earlier than effective US filing date and any foreign priority date); 1998.

Allesee Orthodontic Appliances: DuraClearTM; Product information; 1 page; (year of pub. sufficiently earlier than effective US filing date and any foreign priority date) 1997.

Allesee Orthodontic Appliances; The Choice Is Clear: Red, White & Blue . . . The Simple, Affordable, No-Braces Treatment; ( product information for doctors); retrieved from the internet (http://ormco.com/aoa/appliancesservices/RWB/doctorhtml); 5 pages on May 19, 2003.

Allesee Orthodontic Appliances; The Choice Is Clear: Red, White & Blue . . . The Simple, Affordable, No-Braces Treatment; (product information), 6 pages; (year of pub. sufficiently earlier than effective US filing date and any foreign priority date) 2003.

Allesee Orthodontic Appliances; The Choice is Clear: Red, White & Blue . . . The Simple, Affordable, No-Braces Treatment;(Patient Information); retrieved from the internet (http://ormco.com/aoa/appliancesservices/RWB/patients.html); 2 pages on May 19, 2003.

Allesee Orthodontic Appliances; The Red, White & Blue Way to Improve Your Smile; (information for patients), 2 pages; (year of pub. sufficiently earlier than effective US filing date and any foreign priority date) 1992.

Allesee Orthodontic Appliances; You may be a candidate for this invisible no-braces treatment; product information for patients; 2 pages; (year of pub. sufficiently earlier than effective US filing date and any foreign priority date) 2002.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Alves et al.; New trends in food allergens detection: toward biosensing strategies; Critical Reviews in Food Science and Nutrition; 56(14); pp. 2304-2319; doi: 10.1080/10408398.2013.831026; Oct. 2016.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

Arakawa et al; Mouthguard biosensor with telemetry system for monitoring of saliva glucose: A novel cavitas sensor; Biosensors and Bioelectronics; 84; pp. 106-111; Oct. 2016.

Bandodkar et al.; All-printed magnetically self-healing electrochemical devices; Science Advances; 2(11); 11 pages; e1601465; Nov. 2016.

Bandodkar et al.; Self-healing inks for autonomous repair of printable electrochemical devices; Advanced Electronic Materials; 1(12); 5 pages; 1500289; Dec. 2015.

Bandodkar et al.; Wearable biofuel cells: a review; Electroanalysis; 28(6); pp. 1188-1200; Jun. 2016.

Bandodkar et al.; Wearable chemical sensors: present challenges and future prospects; Acs Sensors; 1(5); pp. 464-482; May 11, 2016.

Barone et al.; Creation of 3D multi-body orthodontic models by using independent imaging sensors; Sensors; 13(2); pp. 2033-2050; Feb. 5, 2013.

Bartels et al.; An Introduction to Splines for Use in Computer Graphics and Geometric Modeling; Morgan Kaufmann Publishers; pp. 422-425 Jan. 1, 1987.

Baumrind et al, "Mapping the Skull in 3-D," reprinted from J. Calif. Dent. Assoc, 48(2), 11 pages; (year of pub. sufficiently earlier than effective US filing date and any foreign priority date) Fall Issue 1972.

Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.

Baumrind; Integrated Three-Dimensional Craniofacial Mapping: Background, Principles, and Perspectives; Seminars in Orthodontics; 7(4); pp. 223-232; Dec. 2001.

beautyworlds.com; Virtual plastic surgery—beautysurge.com announces launch of cosmetic surgery digital imaging services; 5 pages; retrieved from the internet (http://www.beautyworlds.com/cosmossurgdigitalimagning.htm); Mar. 2004.

Begole et al.; A Computer System for the Analysis of Dental Casts; The Angle Orthodontist; 51(3); pp. 252-258; Jul. 1981.

Berland; The use of smile libraries for cosmetic dentistry; Dental Tribune: Asia Pacific Edition; pp. 16-18; Mar. 29, 2006.

Bernabe et al.; Are the lower incisors the best predictors for the unerupted canine and premolars sums? An analysis of peruvian sample; The Angle Orthodontist; 75(2); pp. 202-207; Mar. 2005.

Bernard et al; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.

Bhatia et al.; A Computer-Aided Design for Orthognathic Surgery; British Journal of Oral and Maxillofacial Surgery; 22(4); pp. 237-253; Aug. 1, 1984.

Biggerstaff et al.; Computerized Analysis of Occlusion in the Postcanine Dentition; American Journal of Orthodontics; 61(3); pp. 245-254; Mar. 1972.

Biggerstaff; Computerized Diagnostic Setups and Simulations; Angle Orthodontist; 40(I); pp. 28-36; Jan. 1970.

(56) References Cited

OTHER PUBLICATIONS

Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.
Blu et al.; Linear interpolation revitalized; IEEE Transactions on Image Processing; 13(5); pp. 710-719; May 2004.
Bookstein; Principal warps: Thin-plate splines and decomposition of deformations; IEEE Transactions on pattern analysis and machine intelligence; 11(6); pp. 567-585; Jun. 1989.
Bourke, Coordinate System Transformation; 1 page; retrived from the internet (http://astronomy.swin.edu.au/˜ pbourke/prolection/coords) on Nov. 5, 2004; Jun. 1996.
Boyd et al.; Three Dimensional Diagnosis and Orthodontic Treatment of Complex Malocclusions With the Invisalipn Appliance; Seminars in Orthodontics; 7(4); pp. 274-293; Dec. 2001.
Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.
Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.
Burstone et al.; Precision Adjustment of the Transpalatal Lingual Arch: Computer Arch Form Predetermination; American Journal of Orthodontics; 79(2);pp. 115-133; Feb. 1981.
Burstone; Dr. Charles J. Burstone on the Uses of the Computer in Orthodontic Practice (Part 1); Journal of Clinical Orthodontics; 13(7); pp. 442-453; (interview); Jul. 1979.
Burstone; Dr. Charles J. Burstone on the Uses of the Computer in Orthodontic Practice (Part 2); journal of Clinical Orthodontics; 13(8); pp. 539-551 (interview); Aug. 1979.
Cadent Inc.; OrthoCAD ABO user guide; 38 pages; Dec. 21, 2005.
Cadent Inc.; Reviewing and modifying an orthoCAD case; 4 pages; Feb. 14, 2005.
Cardinal Industrial Finishes; Powder Coatings; 6 pages; retrieved from the internet (http://www.cardinalpaint.com) on Aug. 25, 2000.
Carnaghan, An Alternative to Holograms for the Portrayal of Human Teeth; 4th Int'l. Conf. on Holographic Systems, Components and Applications; pp. 228-231; Sep. 15, 1993.
Chaconas et al,; The DigiGraph Work Station, Part 1, Basic Concepts; Journal of Clinical Orthodontics; 24(6); pp. 360-367; (Author Manuscript); Jun. 1990.
Chafetz et al.; Subsidence of the Femoral Prosthesis, A Stereophotogrammetric Evaluation; Clinical Orthopaedics and Related Research; No. 201; pp. 60-67; Dec. 1985.
Chiappone; Constructing the Gnathologic Setup and Positioner; Journal of Clinical Orthodontics; 14(2); pp. 121-133; Feb. 1980.
Chishti et al.; U.S. Appl. No. 60/050,342 entitled "Procedure for moving teeth using a seires of retainers," filed Jun. 20, 1997.
Collins English Dictionary; Teeth (definition); 9 pages; retrieved from the internet (https:www.collinsdictionary.com/us/dictionary/english/teeth) on May 13, 2019.
Cottingham; Gnathologic Clear Plastic Positioner; American Journal of Orthodontics; 55(1); pp. 23-31; Jan. 1969.
Crawford; CAD/CAM in the Dental Office: Does It Work?; Canadian Dental Journal; 57(2); pp. 121-123 Feb. 1991.
Crawford: Computers in Dentistry: Part 1: CAD/CAM: The Computer Moves Chairside, Part 2: F. Duret ' A Man With a Vision, Part 3: The Computer Gives New Vision—Literally, Part 4: Bytes 'N Bites the Computer Moves From the Front Desk to the Operatory; Canadian Dental Journal; 54(9); pp. 661-666 Sep. 1988.
Crooks; CAD/CAM Comes to USC; USC Dentistry; pp. 14-17; (year of pub. sufficiently earlier than effective US filing date and any foreign priority date) Spring 1990.
CSI Computerized Scanning and Imaging Facility; What is a maximum/minimum intensity projection (MIP/MinIP); 1 page; retrived from the internet (http://csi.whoi.edu/content/what-maximumminimum-intensity-projection-mipminip); Jan. 4, 2010.

Cureton; Correcting Malaligned Mandibular Incisors with Removable Retainers; Journal of Clinical Orthodontics; 30(7); pp. 390-395; Jul. 1996.
Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.
Cutting et al.; Three-Dimensional Computer-Assisted Design of Craniofacial Surgical Procedures: Optimization and Interaction with Cephalometric and CT-Based Models; Plastic and Reconstructive Surgery; 77(6); pp. 877-885; Jun. 1986.
Daniels et al.; The development of the index of complexity outcome and need (ICON); British Journal of Orthodontics; 27(2); pp. 149-162; Jun. 2000.
DCS Dental AG; The CAD/CAM 'DCS Titan System' for Production of Crowns/Bridges; DSC Production; pp. 1-7; Jan. 1992.
Defranco et al.; Three-Dimensional Large Displacement Analysis of Orthodontic Appliances; Journal of Biomechanics; 9(12); pp. 793-801; Jan. 1976.
Dental Institute University of Zurich Switzerland; Program for International Symposium on Computer Restorations: State of the Art of the CEREC-Method; 2 pages; May 1991.
Dentrac Corporation; Dentrac document; pp. 4-13; (year of pub. sufficiently earlier than effective US filing date and any foreign priority date) 1992.
Dentrix; Dentrix G3, new features; 2 pages; retrieved from the internet (http://www.dentrix.com/g3/new_features/index.asp); on Jun. 6, 2008.
Dent-X; Dentsim . . . Dent-x's virtual reality 3-D training simulator . . . A revolution in dental education; 6 pages; retrieved from the internet (http://www.dent-x.com/DentSim.htm); on Sep. 24, 1998.
Di Giacomo et al.; Clinical application of sterolithographic surgical guides for implant placement: Preliminary results; Journal Periodontolgy; 76(4); pp. 503-507; Apr. 2005.
Di Muzio et al.; Minimum intensity projection (MinIP); 6 pages; retrieved from the internet (https://radiopaedia.org/articles/minimum-intensity-projection-minip) on Sep. 6, 2018.
DICOM to surgical guides; (Screenshot)1 page; retrieved from the internet at YouTube (https://youtu.be/47KtOmCEFQk); Published Apr. 4, 2016.
dictionary.com; Plural (definition); 6 pages; retrieved from the internet ( https://www.dictionary.com/browse/plural#) on May 13, 2019.
dictionary.com; Quadrant (definition); 6 pages; retrieved from the internet ( https://www.dictionary.com/browse/quadrant?s=t) on May 13, 2019.
Doruk et al.; The role of the headgear timer in extraoral co-operation; European Journal of Orthodontics; 26; pp. 289-291; Jun. 1, 2004.
Doyle; Digital Dentistry; Computer Graphics World; pp. 50-52 andp. 54; Oct. 2000.
Dummer et al.; Computed Radiography Imaging Based on High-Density 670 nm VCSEL Arrays; International Society for Optics and Photonics; vol. 7557; p. 75570H; 7 pages; (Author Manuscript); Feb. 24, 2010.
Duret et al.; CAD/CAM Imaging in Dentistry; Current Opinion in Dentistry; 1(2); pp. 150-154; Apr. 1991.
Duret et al; CAD-CAM in Dentistry; Journal of the American Dental Association; 117(6); pp. 715-720; Nov. 1988.
Duret; The Dental CAD/CAM, General Description of the Project; Hennson International Product Brochure, 18 pages; Jan. 1986.
Duret; Vers Une Prosthese Informatisee; Tonus; 75(15); pp. 55-57; (English translation attached); 23 pages; Nov. 15, 1985.
Economides; The Microcomputer in the Orthodontic Office; Journal of Clinical Orthodontics; 13(11); pp. 767-772; Nov. 1979.
Ellias et al.; Proteomic analysis of saliva identifies potential biomarkers for orthodontic tooth movement; The Scientific World Journal; vol. 2012; Article ID 647240; dio:10.1100/2012/647240; 7 pages; Jul. 2012.
Elsasser; Some Observations on the History and Uses of the Kesling Positioner; American Journal of Orthodontics; 36(5); pp. 368-374; May 1, 1950.
English translation of Japanese Laid-Open Publication No. 63-11148 to inventor T. Ozukuri (Laid-Open on Jan. 18, 1998) pp. 1-7.

(56) References Cited

OTHER PUBLICATIONS

Faber et al.; Computerized Interactive Orthodontic Treatment Planning; American Journal of Orthodontics; 73(1); pp. 36-46; Jan. 1978.

Farooq et al.; Relationship between tooth dimensions and malocclusion; JPMA: The Journal of the Pakistan Medical Association; 64(6); pp. 670-674; Jun. 2014.

Felton et al.; A Computerized Analysis of the Shape and Stability of Mandibular Arch Form; American Journal of Orthodontics and Dentofacial Orthopedics; 92(6); pp. 478-483; Dec. 1987.

Florez-Moreno; Time-related changes in salivary levels of the osteotropic factors sRANKL and OPG through orthodontic tooth movement; American Journal of Orthodontics and Dentofacial Orthopedics; 143(1); pp. 92-100; Jan. 2013.

Friede et al.; Accuracy of Cephalometric Prediction in Orthognathic Surgery; Journal of Oral and Maxillofacial Surgery; 45(9); pp. 754-760; Sep. 1987.

Friedrich et al; Measuring system for in vivo recording of force systems in orthodontic treatment-concept and analysis of accuracy; J. Biomech.; 32(1); pp. 81-85; (Abstract Only) Jan. 1999.

Futterling et al.; Automated Finite Element Modeling of a Human Mandible with Dental Implants; JS WSCG '98—Conference Program; 8 pages; retrieved from the Internet (https://dspace5.zcu.cz/bitstream/11025/15851/1/Strasser_98.pdf); on Aug. 21, 2018.

Gansky; Dental data mining: potential pitfalls and practical issues; Advances in Dental Research; 17(1); pp. 109-114; Dec. 2003.

Gao et al.; 3-D element Generation for Multi-Connected Complex Dental and Mandibular Structure; IEEE Proceedings International Workshop in Medical Imaging and Augmented Reality; pp. 267-271; Jun. 12, 2001.

Geomagic; Dental reconstruction; 1 page; retrieved from the internet (http://geomagic.com/en/solutions/industry/detal_desc.php) on Jun. 6, 2008.

Gim-Alldent Deutschland, "Das DUX System: Die Technik," 3 pages; (English Translation Included); (year of pub. sufficiently earlier than effective US filing date and any foreign priority date); 2002.

Gottleib et al.; JCO Interviews Dr. James A. McNamura, Jr., on the Frankel Appliance: Part 2: Clinical 1-1 Management; Journal of Clinical Orthodontics; 16(6); pp. 390-407; retrieved from the internet (http://www.jco-online.com/archive/print_article.asp?Year=1982&Month=06&ArticleNum+); 21 pages; Jun. 1982.

Gottschalk et al.; OBBTree: A hierarchical structure for rapid interference detection; 12 pages; (http://www.cs.unc.edu/?geom/OBB/OBBT.html); retrieved from te internet (https://www.cse.iitk.ac.in/users/amit/courses/RMP/presentations/dslamba/presentation/sig96.pdf) on Apr. 25, 2019.

gpsdentaire.com; Get a realistic smile simulation in 4 steps with GPS; a smile management software; 10 pages; retrieved from the internet (http://www.gpsdentaire.com/en/preview/) on Jun. 6, 2008.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Grest, Daniel; Marker-Free Human Motion Capture in Dynamic Cluttered Environments from a Single View-Point, PhD Thesis; 171 pages; Dec. 2007.

Guess et al.; Computer Treatment Estimates in Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Highbeam Research; Simulating stress put on jaw. (ANSYS Inc.'s finite element analysis software); 2 pages; retrieved from the Internet (http://static.highbeam.eom/t/toolingampproduction/november011996/simulatingstressputonfa . . . ); on Nov. 5, 2004.

Hikage; Integrated Orthodontic Management System for Virtual Three-Dimensional Computer Graphic Simulation and Optical Video Image Database for Diagnosis and Treatment Planning; Journal of Japan KA Orthodontic Society; 46(2); pp. 248-269; 56 pages; (English Translation Included); Feb. 1987.

Hoffmann et al.; Role of Cephalometry for Planning of Jaw Orthopedics and Jaw Surgery Procedures; Informatbnen, pp. 375-396; (English Abstract Included); Mar. 1991.

Hojjatie et al.; Three-Dimensional Finite Element Analysis of Glass-Ceramic Dental Crowns; Journal of Biomechanics; 23(11); pp. 1157-1166; Jan. 1990.

Huckins; CAD-CAM Generated Mandibular Model Prototype from MRI Data; AAOMS, p. 96; (Abstract Only); (year of pub. sufficiently earlier than effective US filing date and any foreign priority date) 1999.

Imani et al.; A wearable chemical-electrophysiological hybrid biosensing system for real-time health and fitness monitoring; Nature Communications; 7; 11650. doi 1038/ncomms11650; 7 pages; May 23, 2016.

Invisalign; You were made to move. There's never been a better time to straighten your teeth with the most advanced clear aligner in the world; Product webpage; 2 pages; retrieved from the internet (www.invisalign.com/) on Dec. 28, 2017.

JCO Interviews; Craig Andreiko , DDS, MS on the Elan and Orthos Systems; Interview by Dr. Larry W. White; Journal of Clinical Orthodontics; 28(8); pp. 459-468; 14 pages; (Author Manuscript); Aug. 1994.

JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.

Jeerapan et al.; Stretchable biofuel cells as wearable textile-based self-powered sensors; Journal of Materials Chemistry A; 4(47); pp. 18342-18353; Dec. 21, 2016.

Jerrold; The Problem, Electronic Data Transmission and the Law; American Journal of Orthodontics and Dentofacial Orthopedics; 113(4); pp. 478-479; 5 pages; (Author Manuscript); Apr. 1998.

Jia et al.; Epidermal biofuel cells: energy harvesting from human perspiration; Angewandle Chemie International Edition; 52(28); pp. 7233-7236; Jul. 8, 2013.

Jia et al.; Wearable textile biofuel cells for powering electronics; Journal of Materials Chemistry A; 2(43); pp. 18184-18189; Oct. 14, 2014.

Jones et al.; An Assessment of the Fit of a Parabolic Curve to Pre- and Post-Treatment Dental Arches; British Journal of Orthodontics; 16(2); pp. 85-93; May 1989.

Kamada et.al.; Case Reports on Tooth Positioners Using LTV Vinyl Silicone Rubber; J. Nihon University School of Dentistry; 26(1); pp. 11-29; (year of pub. sufficiently earlier than effective US filing date and any foreign priority date) 1984.

Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.

Kanazawa et al.; Three-Dimensional Measurements of the Occlusal Surfaces of Upper Molars in a Dutch Population; Journal of Dental Research; 63(11); pp. 1298-1301; Nov. 1984.

Karaman et al.; A practical method of fabricating a lingual retainer; Am. Journal of Orthodontic and Dentofacial Orthopedics; 124(3); pp. 327-330; Sep. 2003.

Kesling et al.; The Philosophy of the Tooth Positioning Appliance; American Journal of Orthodontics and Oral surgery; 31(6); pp. 297-304; Jun. 1945.

Kesling; Coordinating the Predetermined Pattern and Tooth Positioner with Conventional Treatment; American Journal of Orthodontics and Oral Surgery; 32(5); pp. 285-293; May 1946.

Kim et al.; A wearable fingernail chemical sensing platform: pH sensing at your fingertips; Talanta; 150; pp. 622-628; Apr. 2016.

Kim et al.; Advanced materials for printed wearable electrochemical devices: A review; Advanced Electronic Materials; 3(1); 15 pages; 1600260; Jan. 2017.

Kim et al.; Noninvasive alcohol monitoring using a wearable tatto-based iontophoretic-biosensing system; Acs Sensors; 1(8); pp. 1011-1019; Jul. 22, 2016.

(56) References Cited

OTHER PUBLICATIONS

Kim et al.; Non-invasive mouthguard biosensor for continuous salivary monitoring of metabolites; Analyst; 139(7); pp. 1632-1636; Apr. 7, 2014.
Kim et al.; Wearable salivary uric acid mouthguard biosensor with integrated wireless electronics; Biosensors and Bioelectronics; 74; pp. 1061-1068; 19 pages; (Author Manuscript); Dec. 2015.
Kleeman et al.; The Speed Positioner; J. Clin. Orthod.; 30(12); pp. 673-680; Dec. 1996.
Kochanek; Interpolating Splines with Local Tension, Continuity and Bias Control; Computer Graphics; 18(3); pp. 33-41; Jan. 1, 1984.
Kumar et al.; All-printed, stretchable Zn—Ag2o rechargeable battery via, hyperelastic binder for self-powering wearable electronics; Advanced Energy Materials; 7(8); 8 pages; 1602096; Apr. 2017.
Kumar et al.; Biomarkers in orthodontic tooth movement; Journal of Pharmacy Bioallied Sciences; 7(Suppl 2); pp. S325-S330; 12 pages; (Author Manuscript); Aug. 2015.
Kumar et al.; Rapid maxillary expansion: A unique treatment modality in dentistry; J. Clin. Diagn. Res.; 5(4); pp. 906-911; Aug. 2011.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Leinfelder et al.; A New Method for Generating Ceramic Restorations: a CAD-CAM System; Journal of the American Dental Association; 118(6); pp. 703-707; Jun. 1989.
Manetti et al.; Computer-Aided Cefalometry and New Mechanics in Orthodontics; Fortschr Kieferorthop; 44; pp. 370-376; 8 pages; (English Article Summary Included); (year of pub. sufficiently earlier than effective US filing date and any foreign priority date) 1983.
Mantzikos et al.; Case report: Forced eruption and implant site development; The Angle Orthodontist; 68(2); pp. 179-186; Apr. 1998.
Martinelli et al.; Prediction of lower permanent canine and premolars width by correlation methods; The Angle Orthodontist; 75(5); pp. 805-808; Sep. 2005.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Methot; Get the picture with a gps for smile design in 3 steps; Spectrum; 5(4); pp. 100-105; (year of pub. sufficiently earlier than effective US filing date and any foreign priority date) 2006.
Moermann et al, Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Moles; Correcting Mild Malalignments—As Easy as One, Two, Three; AOA/Pro Corner; 11(2); 2 pages; (year of pub. sufficiently earlier than effective US filing date and any foreign priority date) 2002.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.
Nash; CEREC CAD/CAM Inlays: Aesthetics and Durability in a Single Appointment; Dentistry Today; 9(8); pp. 20, 22-23 and 54; Oct. 1990.

Nedelcu et al.; "Scanning Accuracy and Precision in 4 Intraoral Scanners: An In Vitro Comparison Based on 3-Dimensional Analysis"; J. Prosthet. Dent.; 112(6); pp. 1461-1471; Dec. 2014.
Newcombe; DTAM: Dense tracking and mapping in real-time; 8 pages; retrieved from the internet (http://www.doc.ic.ac.uk/?ajd/Publications/newcombe_etal_iccv2011.pdf; on Dec. 2011.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Nourallah et al.; New regression equations for predicitng the size of unerupted canines and premolars in a contemporary population; The Angle Orthodontist; 72(3); pp. 216-221; Jun. 2002.
Ogawa et al.; Mapping, profiling and clustering of pressure pain threshold (PPT) in edentulous oral muscosa; Journal of Dentistry; 32(3); pp. 219-228; Mar. 2004.
Ogimoto et al.; Pressure-pain threshold determination in the oral mucosa; Journal of Oral Rehabilitation; 29(7); pp. 620-626; Jul. 2002.
ormco.com; Increasing clinical performance with 3D interactive treatment planning and patient-specific appliances; 8 pages; retrieved from the internet (http://www.konsident.com/wp-content/files_mf/1295385693http_ormco.com_index_cmsfilesystemaction_fileOrmcoPDF_whitepapers.pdf) on Feb. 27, 2019.
OrthoCAD downloads; retrieved Jun. 27, 2012 from the internet (www.orthocad.com/download/downloads.asp); 2 pages; Feb. 14, 2005.
Page et al.; Validity and accuracy of a risk calculator in predicting periodontal disease; Journal of the American Dental Association; 133(5); pp. 569-576; May 2002.
Paredes et al.; A new, accurate and fast digital method to predict unerupted tooth size; The Angle Orthodontist; 76(1); pp. 14-19; Jan. 2006.
Parrilla et al.; A textile-based stretchable multi-ion potentiometric sensor; Advanced Healthcare Materials; 5(9); pp. 996-1001; May 2016.
Patterson Dental; Cosmetic imaging; 2 pages retrieved from the internet (http://patterson.eaglesoft.net/cnt_di_cosimg.html) on Jun. 6, 2008.
Paul et al.; Digital Documentation of Individual Human Jaw and Tooth Forms for Applications in Orthodontics; Oral Surgery and Forensic Medicine Proc. of the 24th Annual Conf. of the IEEE Industrial Electronics Society (IECON '98); vol. 4; pp. 2415-2418; Sep. 4, 1998.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment alignment and leveling; Contemporary Orthodontics, 3rd Ed.; Chapter 16; Mosby Inc.; pp. 534-537; (year of pub. sufficiently earlier than effective US filing date and any foreign priority date) 2000.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & ARS Materials, Inc., Raintree Essix, Technical Magazine Table of contents and Essix Appliances, 7 pages; retrieved from the internet (http://www.essix.com/magazine/defaulthtml) on Aug. 13, 1997.
Redmond et al.; Clinical Implications of Digital Orthodontics; American Journal of Orthodontics and Dentofacial Orthopedics; 117(2); pp. 240-242; Feb. 2000.
Rekow et al.; CAD/CAM for Dental Restorations—Some of the Curious Challenges; IEEE Transactions on Biomedical Engineering; 38(4); pp. 314-318; Apr. 1991.
Rekow et al.; Comparison of Three Data Acquisition Techniques for 3-D Tooth Surface Mapping; Annual International Conference of

(56) References Cited

OTHER PUBLICATIONS the IEEE Engineering in Medicine and Biology Society; 13(1); pp. 344-345 (year of pub. sufficiently earlier than effective US filing date and any foreign priority date) 1991.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art; Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording the Dental Cast in Three Dimensions; American Journal of Orthodontics and Dentofacial Orthopedics; 92(3); pp. 199-206; Sep. 1987.
Rose et al.; The role of orthodontics in implant dentistry; British Dental Journal; 201(12); pp. 753-764; Dec. 23, 2006.
Rubin et al.; Stress analysis of the human tooth using a three-dimensional finite element model; Journal of Dental Research; 62(2); pp. 82-86; Feb. 1983.
Rudge; Dental Arch Analysis: Arch Form, A Review of the Literature; The European Journal of Orthodontics; 3(4); pp. 279-284; Jan. 1981.
Sahm et al.; "Micro-Electronic Monitoring of Functional Appliance Wear"; Eur J Orthod.; 12(3); pp. 297-301; Aug. 1990.
Sahm; Presentation of a wear timer for the clarification of scientific questions in orthodontic orthopedics; Fortschritte der Kieferorthopadie; 51 (4); pp. 243-247; (Translation Included) Jul. 1990.
Sakuda et al.; Integrated Information-Processing System in Clinical Orthodontics: An Approach with Use of a Computer Network System; American Journal of Orthodontics and Dentofacial Orthopedics; 101(3); pp. 210-220; 20 pages; (Author Manuscript) Mar. 1992.
Sarment et al.; Accuracy of implant placement with a sterolithographic surgical guide; journal of Oral and Maxillofacial Implants; 118(4); pp. 571-577; Jul. 2003.
Schafer et al.; "Quantifying patient adherence during active orthodontic treatment with removable appliances using microelectronic wear-time documentation"; Eur J Orthod.; 37(1)pp. 1-8; doi:10.1093/ejo/cju012; Jul. 3, 2014.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Shilliday; Minimizing finishing problems with the mini-positioner; American Journal of Orthodontics; 59(6); pp. 596-599; Jun. 1971.
Shimada et al.; Application of optical coherence tomography (OCT) for diagnosis of caries, cracks, and defects of restorations; Current Oral Health Reports; 2(2); pp. 73-80; Jun. 2015.
Siemens; CEREC—Computer-Reconstruction, High Tech in der Zahnmedizin; 15 pagesl, (Includes Machine Translation); (year of pub. sufficiently earlier than effective US filing date and any foreign priority date); 2004.
Sinclair; The Readers' Corner; Journal of Clinical Orthodontics; 26(6); pp. 369-372; 5 pages; retrived from the internet (http://www.jco-online.com/archive/print_article.asp?Year=1992&Month=06&ArticleNum=); Jun. 1992.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Smalley; Implants for tooth movement: Determining implant location and orientation: Journal of Esthetic and Restorative Dentistry; 7(2); pp. 62-72; Mar. 1995.
Smart Technology; Smile library II; 1 page; retrieved from the internet (http://smart-technology.net/) on Jun. 6, 2008.
Smile-Vision_The smile-vision cosmetic imaging system; 2 pages; retrieved from the internet (http://www.smile-vision.net/cos_imaging.php) on Jun. 6, 2008.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
Sturman; Interactive Keyframe Animation of 3-D Articulated Models; Proceedings Graphics Interface '84; vol. 86; pp. 35-40; May-Jun. 1984.
Szeliski; Introduction to computer vision: Structure from motion; 64 pages; retrieved from the internet (http://robots.stanford.edu/cs223b05/notes/CS%20223-B%20L10%structurefrommotion1b.ppt, on Feb. 3, 2005.
The American Heritage, Stedman's Medical Dictionary; Gingiva; 3 pages; retrieved from the interent (http://reference.com/search/search?q=gingiva) on Nov. 5, 2004.
The Dental Company Sirona: Cerc omnicam and cerec bluecam brochure: The first choice in every case; 8 pages; (year of pub. sufficiently earlier than effective US filing date and any foreign priority date) 2014.
Thera Mon; "Microsensor"; 2 pages; retrieved from the internet (www.english.thera-mon.com/the-product/transponder/index.html); on Sep. 19, 2016.
Thorlabs; Pellin broca prisms; 1 page; retrieved from the internet (www.thorlabs.com); Nov. 30, 2012.
Tiziani et al.; Confocal principle for macro and microscopic surface and defect analysis; Optical Engineering; 39(1); pp. 32-39; Jan. 1, 2000.
Truax; Truax Clasp-Less(TM) Appliance System; The Functional Orthodontist; 9(5); pp. 22-24, 26-28; Sep.-Oct. 1992.
Tru-Tatn Orthodontic & Dental Supplies, Product Brochure, Rochester, Minnesota 55902, 16 pages; (year of pub. sufficiently earlier than effective US filing date and any foreign priority date) 1996.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Vadapalli; Minimum intensity projection (MinIP) is a data visualization; 7 pages; retrieved from the internet (https://prezi.com/tdmttnmv2knw/minimum-intensity-projection-minip-is-a-data-visualization/) on Sep. 6, 2018.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Van Hilsen et al.; Comparing potential early caries assessment methods for teledentistry; BMC Oral Health; 13(16); doi: 10.1186/1472-6831-13-16; 9 pages; Mar. 2013.

(56) References Cited

OTHER PUBLICATIONS

Varady et al.; Reverse Engineering of Geometric Models'An Introduction; Computer-Aided Design; 29(4); pp. 255-268; 20 pages; (Author Manuscript); Apr. 1997.

Verstreken et al.; An Image-Guided Planning System for Endosseous Oral Implants; IEEE Transactions on Medical Imaging; 17(5); pp. 842-852; Oct. 1998.

Vevin et al.; Pose estimation of teeth through crown-shape matching; In Medical Imaging: Image Processing of International Society of Optics and Photonics; vol. 4684; pp. 955-965; May 9, 2002.

Virtual Orthodontics; Our innovative software; 2 pages; (http://www.virtualorthodontics.com/innovativesoftware.html); retrieved from the internet (https://web.archive.org/web/20070518085145/http://www.virtualorthodontics.com/innovativesoftware.html); (year of pub. sufficiently earlier than effective US filing date and any foreign priority date) 2005.

Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.

Warunek et.al.; Clinical Use of Silicone Elastomer Applicances; JCO; 23(10); pp. 694-700; Oct. 1989.

Watson et al.; Pressures recorded at te denture base-mucosal surface interface in complete denture wearers; Journal of Oral Rehabilitation 14(6); pp. 575-589; Nov. 1987.

Wells; Application of the Positioner Appliance in Orthodontic Treatment; American Journal of Orthodontics; 58(4); pp. 351-366; Oct. 1970.

Wiedmann; According to the laws of harmony to find the right tooth shape with assistance of the computer; Digital Dental News; 2nd vol.; pp. 0005-0008; (English Version Included); Apr. 2008.

Wikipedia; Palatal expansion; 3 pages; retrieved from the internet (https://en.wikipedia.org/wiki/Palatal_expansion) on Mar. 5, 2018.

Williams; Dentistry and CAD/CAM: Another French Revolution; J. Dent. Practice Admin.; 4(1); pp. 2-5 Jan./Mar. 1987.

Williams; The Switzerland and Minnesota Developments in CAD/CAM; Journal of Dental Practice Administration; 4(2); pp. 50-55; Apr./Jun. 1987.

Windmiller et al.; Wearable electrochemical sensors and biosensors: a review; Electroanalysis; 25(1); pp. 29-46; Jan. 2013.

Wireless Sensor Networks Magazine; Embedded Teeth for Oral Activity Recognition; 2 pages; retrieved on Sep. 19, 2016 from the internet (www.wsnmagazine.com/embedded-teeth/); Jul. 29, 2013.

Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery; p. 5; Presented on Sep. 13, 1990.

Witt et al.; The wear-timing measuring device in orthodontics-cui Bono? Reflections on the state-of-the-art in wear-timing measurement and compliance research in orthodontics; Fortschr Kieferorthop.; 52(3); pp. 117-125; (Translation Included) Jun. 1991.

Wolf; Three-dimensional structure determination of semi-transparent objects from holographic data; Optics Communications; 1(4); pp. 153-156; Sep. 1969.

Wong et al.; Computer-aided design/computer-aided manufacturing surgical guidance for placement of dental implants: Case report; Implant Dentistry; 16(2); pp. 123-130; Sep. 2007.

Wong et al.; The uses of orthodontic study models in diagnosis and treatment planning; Hong Kong Dental Journal; 3(2); pp. 107-115; Dec. 2006.

WSCG'98—Conference Program, The Sixth International Conference in Central Europe on Computer Graphics and Visualization '98; pp. 1-7; retrieved from the Internet on Nov. 5, 2004, (http://wscg.zcu.cz/wscg98/wscg98.htm); Feb. 9-13, 1998.

Xia et al.; Three-Dimensional Virtual-Reality Surgical Planning and Soft-Tissue Prediction for Orthognathic Surgery; IEEE Transactions on Information Technology in Biomedicine; 5(2); pp. 97-107; Jun. 2001.

Yaltara Software; Visual planner; 1 page; retrieved from the internet (http://yaltara.com/vp/) on Jun. 6, 2008.

Yamada et al.; Simulation of fan-beam type optical computed-tomography imaging of strongly scattering and weakly absorbing media; Applied Optics; 32(25); pp. 4808-4814; Sep. 1, 1993.

Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.

Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.

Yamany et al.; A System for Human Jaw Modeling Using Intra-Oral Images; Proc. of the 20th Annual Conf. of the IEEE Engineering in Medicine and Biology Society; vol. 2; pp. 563-566; Oct. 1998.

Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports; Nippon Dental Review; 457; pp. 146-164; 43 pages; (Author Manuscript); Nov. 1980.

Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.

Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.

Yoshii; Research on a New Orthodontic Appliance: The Dynamic Positioner (D.P.); III—The General Concept of the D.P. Method and Its Therapeutic Effect, Part 2. Skeletal Reversed Occlusion Case Reports; Nippon Dental Review; 458; pp. 112-129; 40 pages; (Author Manuscript); Dec. 1980.

Zhang et al.; Visual speech features extraction for improved speech recognition; 2002 IEEE International conference on Acoustics, Speech and Signal Processing; vol. 2; 4 pages; May 13-17, 2002.

Zhou et al.; Biofuel cells for self-powered electrochemical biosensing and logic biosensing: A review; Electroanalysis; 24(2); pp. 197-209; Feb. 2012.

Zhou et al.; Bio-logic analysis of injury biomarker patterns in human serum samples; Talanta; 83(3); pp. 955-959; Jan. 15, 2011.

Morton et al.; U.S. Appl. No. 16/177,067 entitled "Dental appliance having selective occlusal loading and controlled intercuspation," filed Oct. 31, 2018.

Akopov et al.; U.S. Appl. No. 16/178,491 entitled "Automatic treatment planning," filed Nov. 1, 2018.

O'Leary et al.; U.S. Appl. No. 16/195,701 entitled "Orthodontic retainers," filed Nov. 19, 2018.

Shanjani et al., U.S. Appl. No. 16/206,894 entitled "Sensors for monitoring oral appliances," filed Nov. 28, 2019.

Shanjani et al., U.S. Appl. No. 16/231,906 entitled "Augmented reality enhancements for dental practitioners." Dec. 24, 2018.

Kopleman et al., U.S. Appl. No. 16/220,381 entitled "Closed loop adaptive orthodontic treatment methods and apparatuses," Dec. 14, 2018.

Sabina et al., U.S. Appl. No. 16/258,516 entitled "Diagnostic intraoral scanning" filed Jan. 25, 2019.

Sabina et al., U.S. Appl. No. 16/258,523 entitled "Diagnostic intraoral tracking" filed Jan. 25, 2019.

Sabina et al., U.S. Appl. No. 16/258,527 entitled "Diagnostic intraoral methods and apparatuses" filed Jan. 25, 2019.

Culp; U.S. Appl. No. 16/236,220 entitled "Laser cutting," filed Dec. 28, 2018.

Culp; U.S. Appl. No. 16/265,287 entitled "Laser cutting," filed Feb. 1, 2019.

Arnone et al.; U.S. Appl. No. 16/235,449 entitled "Method and system for providing indexing and cataloguing of orthodontic related treatment profiles and options," filed Dec. 28, 2018.

Mason et al.; U.S. Appl. No. 16/374,648 entitled "Dental condition evaluation and treatment," filed Apr. 3, 2019.

Brandt et al.; U.S. Appl. No. 16/235,490 entitled "Dental wire attachment," filed Dec. 28, 2018.

(56) References Cited

OTHER PUBLICATIONS

Kuo; U.S. Appl. No. 16/270,891 entitled "Personal data file," filed Feb. 8, 2019.
Dental Monitoring; Basics: How to put the cheek retractor?; 1 page (Screenshot); retrieved from the interenet (https://www.youtube.com/watch?v=6K1HXw4Kq3c); May 27, 2016.
Dental Monitoring; Dental monitoring tutorial; 1 page (Screenshot); retrieved from the internet (https:www.youtube.com/watch?v=Dbe3udOf9_c); Mar. 18, 2015.
Ecligner Selfie; Change your smile; 1 page (screenshot); retrieved from the internet (https:play.google.com/store/apps/details?id=parklict.ecligner); on Feb. 13, 2018.
Lawrence; Salivary markers of systemic disease: noninvasive diagnosis of disease and monitoring of general health; Journal of the Canadian Dental Association Clinical Practice; 68(3); pp. 170-174; Mar. 2002.
Nishanian et al.; Oral fluids as an alternative to serum for measurement of markers of immune activation; Clinical and Diagnostic Laboratory Immunology; 5(4); pp. 507-512; Jul. 1998.
Sobral De Agular et al.; The gingival crevicular fluid as a source of biomarkers to enhance efficiency of orthodontic and functional treatment of growing patients; Bio. Med. Research International; vol. 2017; 7 pages; Article ID 3257235; (year of pub. sufficiently earlier than effective US filing date and any foreign priority date) 2017.
Svec et al.; Molded rigid monolithic porous polymers: an inexpensive, efficient, and versatile alternative to beads for design of materials for numerous applications; Industrial and Engineering Chemistry Research; 38(1); pp. 34-48; Jan. 4, 1999.
U.S. Food and Drug Administration; Color additives; 3 pages; retrieved from the internet (https://websrchive.org/web/20070502213911/http://www.cfsan.fda.gov/~dms/col-toc.html); last known as May 2, 2007.
Levin; U.S. Appl. No. 16/282,431 entitled "Estimating a surface texture of a tooth," filed Feb. 2, 2019.
Chen et al.; U.S. Appl. No. 16/223,019 entitled "Release agent receptacle," filed Dec. 17, 2018.
PCT/ISA/220 International Search Report & Written Opinion for related PCT Application PCT/US2018/046982, dated Nov. 14, 2018 (12 pgs).

\* cited by examiner

DENTAL APPLIANCE COMPLIANCE MONITORING

BACKGROUND

Dental treatments may involve restorative and/or orthodontic procedures. Restorative procedures may include implanting a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth or a jaw of a patient over a period of time.

As an example, orthodontic repositioning may be provided through a dental process that uses positioning appliances for realigning teeth. Such appliances may utilize a shell of material having resilient properties, referred to as an "aligner," and/or "orthodontic aligner."

Placement of an aligner over teeth may provide controlled forces in specific locations to gradually move teeth into a new configuration. Repetition of this process with successive appliances in progressive configurations can move the teeth through a series of intermediate arrangements to a final desired arrangement. Aligners can also be used for other dental conditions, such as application of medications, appliances to help with sleep apnea, and other issues.

Some aligner systems utilize a set of aligners that can be used to incrementally reposition teeth without requiring impressions/scans after an initial impression/scan. These aligner systems may use attachments, such as bonded/adhered structures on teeth that interact with active regions of aligners to implement forces on the teeth. The same attachments may be utilized or attachments may be added, removed, or replaced with other attachment shapes that may impart different force characteristics than a previous appliance and attachment combination (i.e., appliance and one or more attachments).

Many treatment plans require patients to wear oral appliances for specified circumstances, such as specified duration(s) or in specified manner(s). While it may be desirable to monitor compliance, it is often difficult to do so. Monitoring compliance may also provide insight into the efficacy of an oral appliance and/or treatment plan is.

DETAILED DESCRIPTION

The present disclosure describes devices, systems, and methods for monitoring use of an oral appliance in an oral cavity using an extra-oral compliance indicator system in which extra-oral sensor(s) are configured to gather compliance information about the oral appliance while remaining outside the oral cavity.

In the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

Figure 1A:
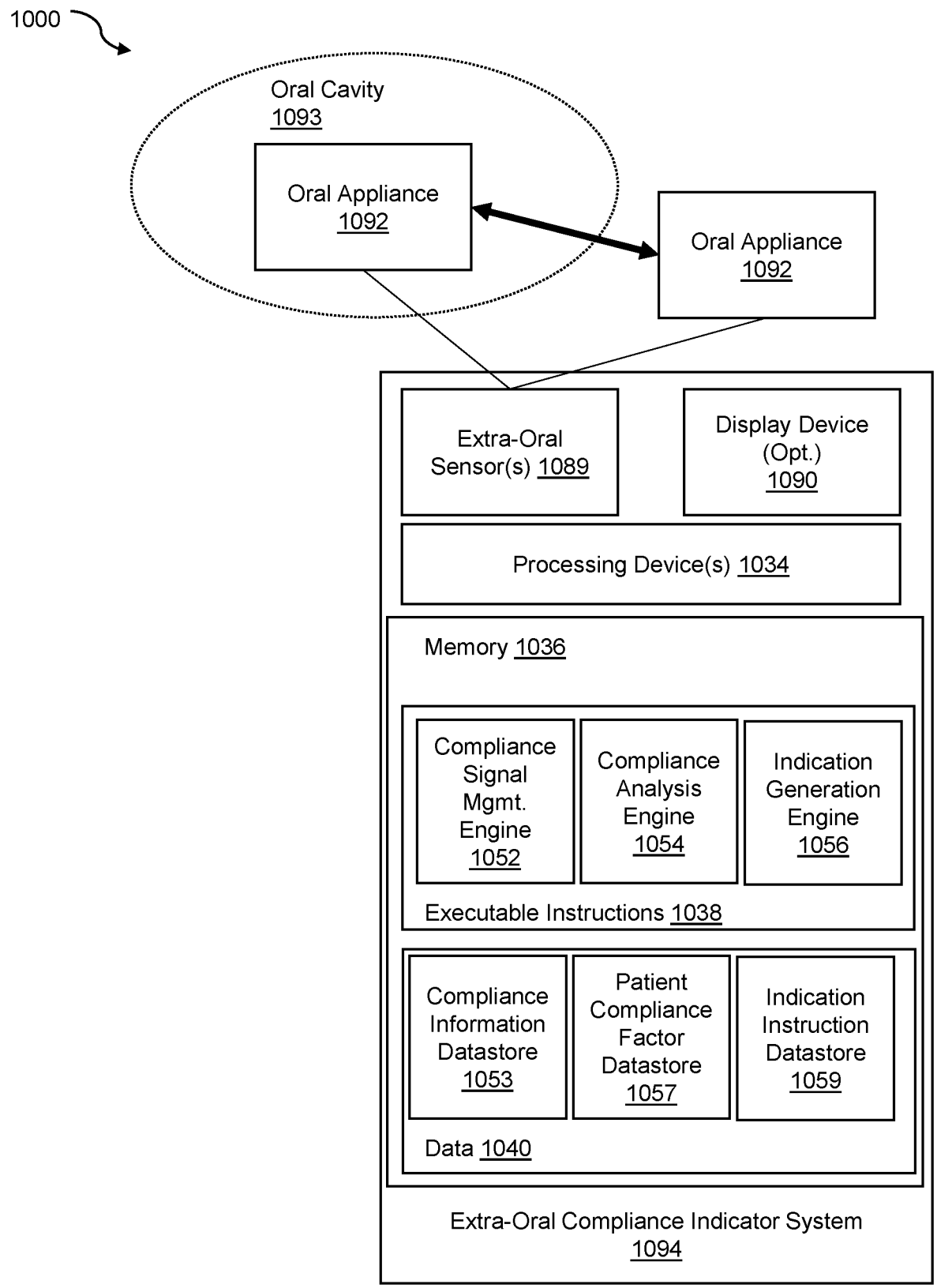
FIG. 1A illustrates an extra-oral compliance monitoring environment for monitoring use of an oral appliance within an oral cavity, according to some implementations of the present disclosure.

FIG. 1A illustrates an extra-oral compliance monitoring environment 100A, according to some implementations. In this example, the extra-oral compliance monitoring environment 100A includes an oral appliance 1092, an oral cavity 1093, an extra-oral compliance indicator system 1094, and a case (not shown in FIG. 1A). One or more of the elements of the extra-oral compliance monitoring environment 100A may be coupled to one another or to modules not explicitly shown.

The oral cavity 1093 may include the oral cavity of a patient. The oral cavity 1093 may correspond to some or all of a patient's mouth. The case (not shown in FIG. 1A) may include a physical container to encase the oral appliance 1092. The case may include a dental appliance packaging box.

The oral appliance 1092 (and any "oral devices" used herein) may include any device used to adjust or maintain teeth and/or skeletal structures within the oral cavity. The oral appliance 1092 may reside in the oral cavity 1093 for various duration(s) and/or under various circumstances. Examples of oral appliances include orthodontic appliances (braces, orthodontic aligners alone or in combination with attachments, etc.), palatal expanders, mandibular modification devices/features, retainers, bruxism devices, etc. As used herein, the language, "dental appliance" and the language, "oral appliance" may be used interchangeably and include a device that implements at least a part of a treatment plan on a patient's teeth and is placed into the patient's oral cavity. In this example, the oral appliance 1092 may reside within the oral cavity 1093 at some times and may reside outside the oral cavity 1093 at other times. The durations of time the oral appliance 1092 resides in the oral cavity 1093 may correspond to times a patient complies with a treatment plan. As an example, some orthodontic treatment plans may require patient's to wear orthodontic appliances for a specified amount of time per day. The oral appliance 1092 may reside within the oral cavity 1093 for time(s) the patient actually complies with the requirements of the orthodontic treatment plan. As patient compliance with a treatment plan may vary, it is noted the durations of time the oral appliance 1092 resides in the oral cavity 1093 may, but need not, correspond with the specifications of a treatment plan.

The extra-oral compliance indicator system 1094 may include extra-oral sensor(s) 1089, a display device 1090, one or more processing devices 1034, and memory 1036. The extra-oral compliance indicator system 1094 and any "extra-oral" device described herein may operate outside the oral cavity 1093. For instance, in some implementations, one or more of the components of the extra-oral compliance indicator system 1094 may not reside on the oral appliance 1092. Some or all of the extra-oral compliance indicator system 1094 may be incorporated into the oral appliance 1092. Some or all of the extra-oral compliance indicator system 1094 may be incorporated extra-orally, e.g., on a case that holds the oral appliance, on extra-oral portions of a patient's body (e.g., portions in a patient's ear), on a computing device such as a mobile phone, tablet, laptop, desktop, etc.

The extra-oral sensor(s) 1089 may comprise a sensor with components that operate outside the oral cavity 1093. The extra-oral sensor(s) 1089 may include physical and/or electrical components that detect or measure one or more physical properties of usage of the oral appliance 1092 and record, indicate, and/or respond to those properties. The extra-oral sensor 1098 may be configured to sense when an oral appliance is inside, or alternatively, outside, a patient's oral cavity. In some implementations, some portions or all of the extra-oral sensor(s) 1089 is incorporated extra-orally. As an example, some portions or all of the extra-oral sensor(s) 1089 may be incorporated into a case configured to hold the oral appliance 1092. As another example, some portions or all of the extra-oral sensor(s) 1089 are incorporated into extra-oral portions of the patient's body, such as portions of the patient's ear. As yet another example, some portions or all of the extra-oral sensor(s) 1089 may be incorporated into a computing device such as a mobile phone, tablet, laptop, desktop, etc. The extra-oral sensor(s) 1089 may be configured to detect whether the oral appliance 1092 is at a specified orientation relative to the oral cavity 1093 (e.g., inside the oral cavity 1093, outside the oral cavity 1093, etc.).

The extra-oral sensor(s) 1089 may be implemented according to a variety of techniques. In some implementations, the extra-oral sensor(s) 1089 comprises an energy source and a discharge circuit that senses discharge of power, energy, current, etc. from the energy source. The discharge circuit may discharge power from a power source through a power draining element when the oral appliance 1092 is at a specified orientation relative to the oral cavity 1093 (e.g., inside the oral cavity 1093, outside the oral cavity 1093, etc.). As one example, the discharge circuit may be configured to implement an open circuit when the oral appliance 1092 is inside the oral cavity 1093 and a closed circuit when the oral appliance 1092 is outside the oral cavity 1093. In such implementations, the energy source may be drained when the oral appliance 1092 is outside the oral cavity 1093. Conversely, the discharge circuit may implement an open circuit when the oral appliance 1092 is outside the oral cavity 1093 and a closed circuit when the oral appliance 1092 is inside the oral cavity 1093, thereby causing the energy source to be drained when the oral appliance 1092 is inside the oral cavity 1093. In various implementations, the extra-oral sensor(s) 1089 comprises a discharge circuit incorporated into a case that is configured to hold the oral appliance 1092.

The extra-oral sensor(s) 1089 may comprise a magnetic sensor that varies a voltage in response to changes in a magnetic field. The changes in the magnetic field may indicate whether the oral appliance 1092 is at a specified orientation relative to the oral cavity 1093. The magnetic sensor may use the Hall effect (e.g., the production of a potential difference across an electrical conductor when a magnetic field is applied in a direction perpendicular to that of the flow of current) in order to sense changes to a magnetic field. In some implementations, a first portion of the magnetic sensor is incorporated into the oral appliance 1092 and a second portion of the magnetic sensor is located outside the oral cavity 1093. As examples, the first portion of the magnetic sensor may comprise a magnetic and/or metallic portion of the oral appliance 1092. The second portion of the magnetic sensor may be incorporated outside the oral cavity 1093, e.g., in a patient's ear, nose, throat, and/or on jewelry or other items that can be attached to the patient.

In some implementations, the extra-oral sensor(s) 1089 comprises a metallic sensor that senses when the oral appliance 1092 is inside its case. In some implementations, a first portion of the metallic sensor is incorporated into the oral appliance 1092 and a second portion of the metallic sensor is incorporated into the case. In such implementations, the metallic sensor may be configured to sense proximity, conductive characteristics, or other characteristics of the oral appliance 1092.

In various implementations, the extra-oral sensor(s) 1089 may comprise a biosensor that senses living organism(s), biological molecule(s) (e.g., especially enzymes, antibodies, etc.), etc. to detect the presence of specific chemicals on the oral appliance 1092. Such chemicals may be included, even residually, on saliva or other biological materials on the oral appliance 1092 after the oral appliance 1092 has been removed from the oral cavity 1093.

The extra-oral sensor(s) 1089 may include one or more image sensors that are configured to use image recognition techniques to determine whether or not the oral appliance 1092 is proximate to it and/or within the case of the oral appliance 1092. The extra-oral sensor(s) 1089 may, for instance, comprise a light source sensor incorporated into the case. The light source sensor may comprise a light source and a light detector that determines when the light source has been blocked. As noted herein, the light source may be blocked when the oral appliance 1092 is inside its case; the detector may provide information corresponding to detection of the oral appliance 1092 accordingly. Alternatively, the light source may be blocked when the oral appliance is outside its case; the detector may correspondingly provide information corresponding to detection of the oral appliance 1092.

The extra-oral sensor(s) 1089 may include image sensor(s) that detect features of the oral appliance 1092. As such, the extra-oral sensor(s) 1089 may implement cameras and/or other image capture devices that allow images of the oral appliance 1092 to be captured. The cameras and/or image capture devices may be used to compare depictions of the oral appliance 1092 with depictions of known or estimated properties (shapes, sizes, use properties, thicknesses, stages, etc.) of the oral appliance 1092. The cameras and/or image capture devise may be used to compare locations and/or other metadata of depictions of the oral appliance 1092 to see, e.g., if the oral appliance 1092 is at known location.

As another example, the extra-oral sensor(s) 1089 may comprise one or more locational sensors that sense locations of the oral appliance 1092. The extra-oral sensor(s) 1089 may include, e.g., sensors using Bluetooth, near field communication (NFC), Ultraband, and Zigbee, among other communication types, or longer range (greater than 15 meters), such as infrared or W-Fi communication types.

As yet another example, the extra-oral sensor(s) 1089 may include sensors configured to detect material properties of the oral appliance 1092 based on a response to a light source (e.g., infrared light source). For instance, the extra-oral sensor(s) 1089 may be configured to identify reflective, refractory, diffusive, etc. patterns from light shined on the oral appliance 1092. In some implementations, the extra-oral sensor(s) 1089 may be part of a system to detect whether the materials used to form the oral appliance 1092 are of a specific polymeric material or are counterfeits, fakes, etc.

The extra-oral sensor(s) 1089 may be configured to provide a compliance signal that indicates whether or not the oral appliance is inside/outside the patient's oral cavity. The compliance signal may be used to determine compliance information. "Compliance information," as used herein, may include any information related to patient compliance with a treatment plan, and can include such factors as time(s) an oral appliance has been worn and/or in an oral cavity, time(s) an oral appliance has not been worn and/or in an oral cavity, physical modification (e.g., of shapes, sizes, material properties, etc.) of an oral appliance as a result of wear and/or residence in/out of an oral cavity, etc. In various implementations, the compliance information may be used to determine whether or not a patient is sufficiently complying with parameters of a treatment plan. The compliance information may, for instance, be used to determine whether or not a patient is wearing oral appliance(s) for prescribed periods of time. The compliance information may also be used as the basis of one or more display elements that display to the patient and/or treatment professionals the extent a patient is complying with parameters of a treatment plan.

The display device 1090 may include a physical device configured to display data. The display device 1090 may include a computer screen, video and/or graphics hardware, a touchscreen, etc. In some implementations, the display device 1090 includes a light, e.g., a Light Emitting Diode (LED) that provides an indicator to a user. The display device 1090 may be configured to display the data to a patient, to a treatment professional, etc.

The processing device(s) 1034 may include one or more physical computer processors that can execute computer-program instructions and/or computer-implemented methods. The processing device(s) 1034 may execute the executable instructions 1038 in the memory 1036. The memory 1036 may include volatile and/or non-volatile memory. The memory 1036 may include executable instructions 1038 and data 1040.

The executable instructions 1038 may include a compliance signal management engine 1052, a compliance analysis engine 1054, and an indication generation engine 1056. As used herein, an engine may include computer-program instructions executed by one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like.

As such, a first engine and a second engine can be executed by one or more dedicated processors or a first engine and a second engine can share one or more processors with one another or other engines. Depending upon implementation-specific or other considerations, an engine can be centralized or its functionality distributed. An engine can be executed by hardware, firmware, or software embodied in computer-readable medium for execution by the processor(s). The processing device(s) 1034 may transform data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices and need not be restricted to only one computing device. In some embodiments, the cloud-based engines can execute functionalities and/or modules that end users access through a web browser or container application without having the functionalities and/or modules installed locally on the end-users' computing devices.

The compliance signal management engine 1052 may implement one or more automated agents configured to process a compliance signal from the extra-oral sensor 1089. The compliance signal management engine 1052 may receive the compliance signal over a computer-readable medium coupling the extra-oral sensor 1089 to it. The compliance signal may be relevant to compliance information, as noted further herein. In some implementations, the compliance signal management engine 1052 is configured to extract and/or provide compliance information to other modules, such as the compliance analysis engine 1052.

The compliance analysis engine 1054 may implement one or more automated agents configured to analyze patient compliance with an orthodontic treatment plan based on the compliance information. In some implementations, the compliance analysis engine 1054 may implement rules to identify patient compliance factors based on compliance information. "Patient compliance factors," as used herein, may include factors that indicate whether or not a patient usage of the oral appliance 1092 complies with a treatment plan. Patient compliance factors may include whether time(s), date(s), material properties, etc. of usage correspond with usage typically found for a treatment plan. As an example, if a treatment plan calls for the oral appliance 1092 to be worn a specified amount of time in a day, the compliance analysis engine 1054 may determine whether compliance information indicates wear for the specified amount of time.

The indication generation engine 1056 may implement one or more automated agents configured to provide a compliance indicator based on patient compliance factors. A "compliance indicator," as used herein, may include an indication of the extent a patient is complying with a treatment plan that calls for use of the oral appliance 1092. Compliance indicators may include a determination of whether or not a patient is complying with parameters of a treatment plan. In various implementations, the compliance analysis engine 1054 may represent the compliance indicator as a Boolean value, other numerical score representing compliance, an alphanumeric sequence representing compliance, etc. In some implementations, the indication generation engine 1056 instructs the display device 1090 to display compliance indicators.

The memory 1040 may include a compliance information datastore 1053, a patient compliance factor datastore 1057, and an indication instruction datastore 1059.

As used herein, datastores may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud based datastore is a datastore that is compatible with cloud-based computing systems and engines.

The compliance information datastore 1053 may be configured to store compliance information. The patient compliance factor datastore 1057 may be configured to store patient compliance factors. The indication instruction datastore 1059 may be configured to store compliance indicators.

In some implementations, the devices of the extra-oral compliance monitoring environment 100A may operate to monitor patient compliance with an orthodontic treatment plan, which is discussed further herein. As noted herein, depending on the implementation, the extra-oral sensor(s) 1089 may, through communication and/or sensing of the oral appliance 1092, determine whether or not the oral appliance 1092 resides within the oral cavity 1093. The extra-oral sensor(s) 1089 may provide to the compliance signal management engine 1052 a compliance signal which may contain therein compliance information representative of compliance to an orthodontic treatment plan. The compliance signal management engine 1052 may operate to process the compliance signal from the extra-oral sensor 1089 and provide it to the compliance analysis engine 1054, which may operate to identify patient compliance factors based on the compliance information. In various implementations, the indication generation engine 1056 may operate to provide a compliance indicator based on the patient compliance factors. The indication generation engine 1056 may further configure the display device 1090 to display a representation of the compliance indicator.

Figure 1B:
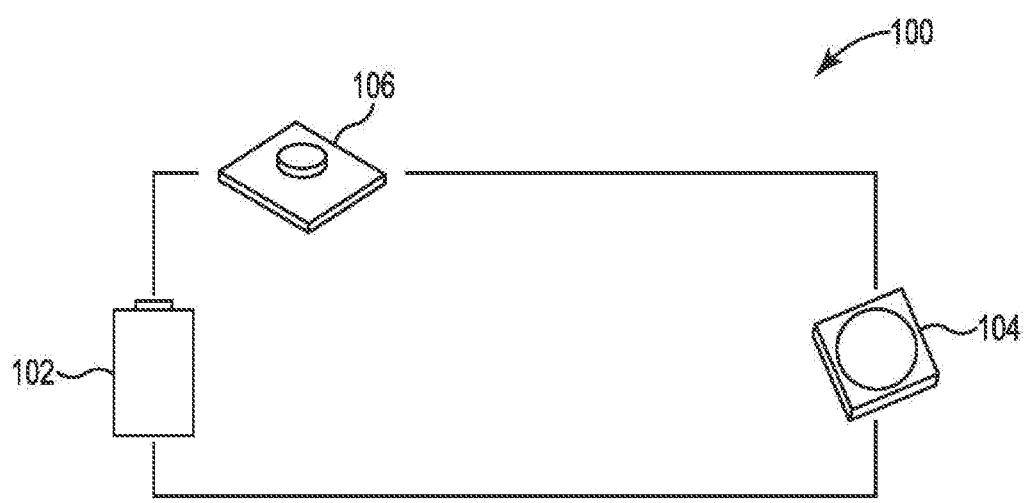
FIG. 1B illustrates a circuit diagram of a compliance monitoring device according to a number of embodiments of the present disclosure.

FIG. 1B illustrates a diagram of a compliance monitoring circuit 100 according to some embodiments. The compliance monitoring circuit 100 may correspond to portions of the extra-oral sensor(s) 1089 shown in FIG. 1A. More particularly, the compliance monitoring circuit 100 may implement a discharge circuit that discharges power from a power source 102 through a power draining element 104 when a circuit actuation mechanism 106 has indicated the oral appliance 1092 is (depending on implementation) either inside or outside the oral cavity 1093. The compliance monitoring circuit 100 may be incorporated into and/or coupled to the compliance signal management engine 1052 and/or the oral appliance 1092 (shown in FIG. 1A). In some embodiments of the present disclosure, an oral appliance compliance system can include an oral appliance having a body. The oral appliance can also include a power source attached to the body, wherein the power source has a predetermined power level and a power draining element and a compliance component attached to the body, the compliance component connected to the power source, wherein a comparison of the predetermined power level and a power level of the power source after interaction with the power draining element is used to indicate whether the patient is wearing the oral appliance in compliance with an amount of time provided in a treatment plan created for the patient.

The compliance component can include a power source having a predetermined power level and a power draining element, wherein a comparison of the predetermined power level and a power level of the power source after interaction with the power draining element is used to indicate whether the patient is wearing the oral appliance in compliance with an amount of time provided in a treatment plan created for the patient, the compliance component including a sensor to indicate whether the oral appliance is out of a patient's mouth. FIG. 1B illustrates one such system.

FIG. 1B illustrates a circuit diagram of a compliance monitoring device according to a number of embodiments of the present disclosure. In the embodiment of FIG. 1B, the compliance monitoring circuit 100 has the power source (e.g., battery or other type of power cell) 102, a capacitor (not shown in FIG. 1B), the power draining element 104, and the circuit actuation mechanism 106. This design can be configured in two ways. Specifically, the device can have a first configuration wherein the device is actuated when the patient is wearing the device and a second configuration wherein the device is actuated when the patient is not wearing the device.

In the first configuration, the circuit actuation mechanism 106 can be actuated when the oral appliance is being worn. For example, the circuit actuation mechanism can be a button that when depressed, allows power to flow through the circuit to the power draining element which thereby reduces the power in the power source over time. If the amount of power (a starting power level) is known at the beginning of treatment and the amount of power that is drained from the circuit over time is also known, then the amount of time that the oral appliance is worn can be calculated based upon the comparison of the power level before treatment commences and the power level after the treatment period has ended.

In the second configuration, the circuit actuation mechanism 106 can be actuated when the oral appliance is not being worn. For example, the circuit actuation mechanism can be a button that when not depressed, allows power to flow through the circuit to the power draining element which thereby reduces the power in the power source over time. As with the first configuration, if the amount of power (a starting power level) is known at the beginning of treatment and the amount of power that is drained from the circuit over time is also known, then the amount of time that the oral appliance is worn can be calculated based upon the comparison of the power level before treatment commences and the power level after the treatment period has ended.

This second configuration may need less power, in comparison to the power needed for the first configuration, available in the power source (and, therefore, potentially a smaller power source) as the patient should be wearing the oral appliance a substantial majority of the time during the treatment period. For example, some treatment plans recommend that a patient wear their dental appliance eighteen hours out of a twenty-four hour period. Accordingly, the circuit of the first configuration would be actuated and draining power for eighteen hours out of a twenty-four hour period for each day over the period of treatment. As this configuration tracks the actual time that the oral appliance is in the mouth of the patient, it may be beneficial in some implementations.

The circuit of the second configuration alternatively tracks the time the oral appliance is not in the mouth of the patient. Such a configuration would be actuated and draining power for six hours out of a twenty-four hour period for each day over the period of treatment. As can be determined by this analysis, the power source could accordingly, be reduced by two thirds the capacity of the first configuration, which could be a substantial savings in form factor, amount of power, cost, and comfort of the patient and could offer more options with regard to placement of the power source and/or the compliance monitoring device as a whole, among other benefits.

The compliance monitoring device can be configured to track the total time of use of the oral appliance or non-use of the oral appliance or can be set to track compliance to a threshold. For example, as discussed above, if the starting power level (e.g., voltage) is known and the power source can be drained in a metered manner to a lower power level that is above zero, then the difference in power levels can be compared and the time of compliance can be calculated based upon the power used and the known level of substantially uniform draining of the power source over time.

However, if a treatment professional simply wants to know whether the oral appliance was worn for a threshold amount of time, the initial power level can be selected such that compliance is achieved when the power source is fully depleted (power level is zero). In this manner, a smaller power source may be used and less power may be needed.

Such an embodiment could also be used to provide the amount of compliance below the threshold. For example, a similar calculation could be done with respect to that above regarding ending power levels above zero (e.g., (initial power level minus ending power level above zero)/drainage rate=amount of compliance).

The circuit 100 is preferably of a form factor sufficiently small to be attached to an oral appliance and not be noticeable to the patient wearing of the appliance with regard to the comfort of the patient. For example, a preferable embodiment would be sized such that it can be substantially embedded (as will be discussed in more detail below) and not change the exterior shape of the oral appliance.

In some embodiments, the form factor of the compliance monitoring device being attached and/or embedded within the oral appliance may change the exterior shape of the oral appliance up to 2 mm in each of one or more dimensions without substantially affecting the patient's comfort. Accordingly, such embodiments and perhaps others with even larger changes would be acceptable to the patient and, as such, are suitable embodiments of the present disclosure.

In some embodiments, the power source may be located remotely from one or more of the other components of the circuit. For example, an oral appliance may have surfaces that form separate cavities for the placement of each tooth along one jaw of the patient and the power source may be positioned on a first surface forming a cavity of a first tooth while the other components are positioned on a second surface forming a cavity of a second tooth. In some embodiments, the power source may be on a lingual surface of a cavity of a tooth and the one or more other components may be on a buccal surface of the cavity of the same tooth.

The power source 102 is preferably of a small form factor and, as discussed above, has sufficient power to allow the compliance device to function over the course of the length of the treatment period in which the patient is to be using the oral appliance (e.g., a week, a month, a year, etc.) upon which the compliance monitoring device is to be worn. For example, in some embodiments, if the oral appliance is supposed to be used by the patient for two weeks, the power source should last slightly longer than two weeks, such that the power source is not fully exhausted before the end of the treatment period.

Further, in some embodiments, compliance can be checked during treatment by comparing a pretreatment power level with a current power level. Once the difference is calculated the resultant power level can be compared to an amount of compliance based on the power drain rate for the time period the treatment has been on going to see if compliance is being achieved. This can be helpful during a treatment period to correct dental appliance usage before a full treatment period has gone by, among other benefits.

In some embodiments, the power source can be rechargeable to enable the oral appliance to be reused. For example, the oral appliance can be a retainer and the power source can have sufficient power to measure compliance between visits to the treatment professional. The power source can then be recharged with sufficient power to track compliance between the present visit and the next visit.

In some embodiments, the amount of recharge power can be different for times between visits that are different lengths, such as six months between visits and three months between visits. For example, is some embodiments, a first patient may have regular visits every three months and a second patient may have visits every six months.

In such embodiments, the treatment professional may fill the power supplies to different levels and/or the power supplies may be of different sizes. In some embodiments, a single patient may have a period of six months between visits and another period of three months between visits. In such an embodiment, the treatment professional could fill the power source to different levels or, in some embodiments, the treatment professional could install a larger or smaller power source to accommodate the different time period.

The power draining element can be any resistive element that will drain power at a known metered rate over time. One suitable element is a light source such as a light emitting diode (LED). Light emitting diodes can be beneficial as they are relatively inexpensive, among other benefits.

In such an embodiment, a compliance determination device can be used to measure a characteristic of emitted light from the light source and determine whether a user of the oral appliance is in compliance based on the characteristic of the emitted light. Suitable examples of characteristics that can be measured can be luminosity, intensity, wavelength, and any other characteristic that can change as a power supply providing power to a light source loses power over time.

Another suitable element is a clock circuit. For example, a clock circuit can be provided that records the time when it stops. If the start time is known, then the time of compliance can be calculated based on the difference between the start and stop times. If the clock records the time it stops, this computation can be done at any time after it stops and therefore can be beneficial in some implementations, as it does not need to be calculated right away or before the power source is exhausted, among other benefits.

The circuit actuation mechanism can be any suitable actuation mechanism. For instance, a pressure sensitive actuation mechanism can be used to activate the sensor. In such an implementation, the pressure sensitive actuation mechanism can be used to activate the sensor when the pressure sensitive actuation mechanism is placed against a surface of a tooth of the patient. This mechanism can be used to either actuate the circuit or disable the circuit depending on whether the circuit is designed to track time that the appliance is in use or not in use.

For example, as discussed above, a button type mechanism that actuates the circuit either when it is depressed or not depressed can be a suitable type of circuit actuation mechanism. Other suitable types of actuation mechanisms can be a proximity mechanism, where the mechanism senses proximity to a tooth, a chemical sensor where the sensor determines contact with a chemical in the air or saliva in the mouth of the patient, or a wetness sensor wherein the sensor determines contact with saliva. In each of these examples, the detection of the sensed item can either be used to actuate the circuit or turn off the circuit depending on whether the circuit is being used to monitor the time the oral appliance is in the mouth of the patient or out of the mouth of the patient.

In some embodiments, as shown in FIG. 1B, the system can include the circuit 100, having a power source (e.g., battery or other type of power cell) 102, a power draining element 104, and a circuit actuation mechanism 106 (e.g., to sense whether the oral appliance is out of a patient's mouth). In such an embodiment, the power draining element would be continuously draining the power source when the circuit actuation mechanism is activated. Such an embodiment may be beneficial, for example, in reducing the complexity of the system, assembly time, parts costs, among other benefits.

However, in some embodiments, a resistor-capacitor (RC) circuit can be used in the system. Such a circuit, when, for example, used with an LED or other light source, causes the light to blink.

In this manner, the light can be used to monitor compliance, but it is not on all the time when actuated and thereby less power needs to be provided by the power source. This allows less power to be added to the power source and/or a smaller power source to be used.

Some embodiments can include a transmitter to transmit compliance data from the compliance component to a remote device. In various embodiments, compliance data can be power level data or clock circuit data such as a number of total clock cycles and/or cycles since the last time a transmission of such data was sent.

A compliance component can, for example, analyze a power level of the power source and determine whether a user of the oral appliance is in compliance based on the power level indicated as compared to a pretreatment power level or based on a predetermined threshold power level that has been determined, for example, through testing of the circuit. This, for instance, can be accomplished when a compliance determination device is connected to the power source, analyzes a power level of the power source, and determines whether a user of the oral appliance is in compliance.

Figure 2:
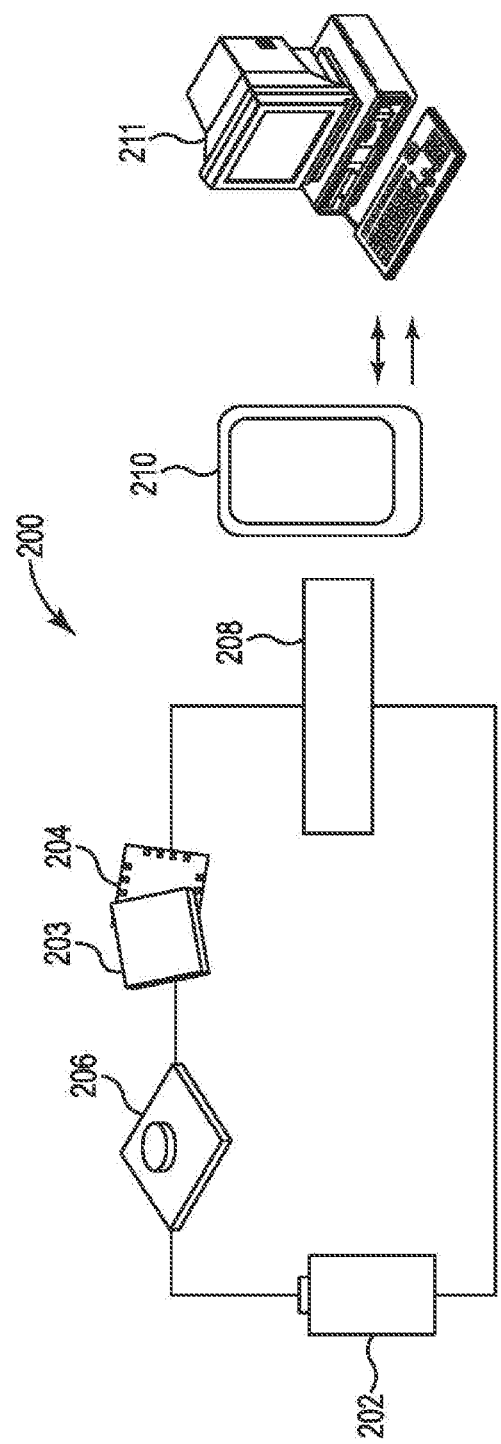
FIG. 2 illustrates a circuit diagram of another compliance monitoring device according to a number of embodiments of the present disclosure.

As discussed in more detail in FIG. 2, in some embodiments, the oral appliance compliance system can include a compliance determination device that receives the compliance data (in a wired or wireless communication) and determines whether a user of the oral appliance is in compliance with a defined threshold of usage for a treatment period based on a comparison of the compliance data received and a threshold value. As discussed herein a threshold value could be a continuous period, such as three hours in the case in one day (24 hour period), or a cumulative period, such as 25 hours during an entire treatment period. The threshold can be any suitable threshold and can be determined and set, for example, by the manufacturer of the circuit or case, by the treatment professional, or by the patient or their parent or guardian, in various embodiments.

The compliance determination device could, in some implementations be used to provide power to the power source in a wired or wireless manner. This could be accomplished by having a power scavenging component as part of the circuit to collect energy from the compliance determination device and use the collected energy to increase the amount of power stored by the power source. This can, for example, be accomplished via near field communication (NFC) technology that can be used to transfer energy from a device that comes within the range of a near field antenna. Movement, temperature, light, or other power sources used to provide power can be used with scavenging technologies to provide power to the power source connected to the compliance component.

Additionally, any power scavenging technology can be used to provide power to the power source connected to the compliance component. Further, although described in some areas of this disclosure as having power provided from the compliance determination device, it should be noted that any device can be used to provide power to the power source connected to the compliance component.

As described above, in some embodiments, an oral appliance compliance system can include a compliance component to be attached to a body of an oral appliance that has a power source with a predetermined power level and a power draining element. In such an embodiment, a comparison of the predetermined power level and a power level of the power source after interaction with the power draining element can be used to indicate whether the patient is wearing the oral appliance in compliance with an amount of time provided in a treatment plan created for the patient. In this manner, compliance can be measured without having a sensor as part of the circuit on the body of the oral appliance. Such an implementation reduces the amount of components used and could reduce the form factor of the compliance component, which has several benefits, as discussed above.

In another embodiment, an oral appliance compliance system includes a compliance component attached to a body of an oral appliance to be positioned in the mouth of a patient that has a power source with a predetermined power level and a power draining element. A power sensor can be used to determine the predetermined power level. For example, this can be accomplished through use of a voltage measuring device connected to the compliance component and measured at manufacture, packaging of the oral appliance, presentation to the patient by a treatment professional, or other suitable time. Additionally, a power sensor can measure the power level of the power source after interaction with the power draining element to determine values to compare the predetermined value with the after interaction value.

The comparison of the predetermined power level and a power level of the power source after interaction with the power draining element can be used to indicate whether the patient is wearing the oral appliance in compliance with an amount of time provided in a treatment plan created for the patient. The compliance component also can include a power source and a sensor to indicate whether the patient is wearing the oral appliance in compliance with an amount of time provided in a treatment plan created for the patient.

In such an embodiment, the sensor can, for example, be a clock circuit that counts elapsed time since a last reading. The sensor can, for example, be activated when the appliance is removed from the mouth of the patient.

FIG. 2 illustrates a circuit diagram of a compliance monitoring circuit 200 according to a number of embodiments of the present disclosure. The embodiment of FIG. 2 is similar to FIG. 1B in that the circuit 200 tracks the depletion of the power source 202 over time by a power draining element 203. The compliance monitoring circuit 200 may correspond to portions of the extra-oral sensor(s) 1089 shown in FIG. 1A. More particularly, the compliance monitoring circuit 200 may implement a discharge circuit that discharges power from a power source 202 through a power draining element 204 when a circuit actuation mechanism 206 has indicated the oral appliance 1092 is (depending on implementation) either inside or outside the oral cavity 1093. The compliance monitoring circuit 200 may be incorporated into and/or coupled to the compliance signal management engine 1052 and/or the oral appliance 1092 (shown in FIG. 1A). As an example, at least parts of a transmission component 208, a remote device 210, and/or another remote device 211 may be incorporated into the extra-oral compliance indicator system 1094, shown in FIG. 1A.

In the embodiment of FIG. 2, however, the circuit also includes a transmission component 208 that can transmit current compliance information to a remote device 210. The transmission component can be any suitable transmitter. The circuit can also include an integrated circuit 204, as is described herein. In some embodiments, the transmission component can be an antenna and the transmitter can either be part of the transmission component 208 or part of the integrated circuit 204.

For example, in some embodiments, it would be beneficial to use a small form factor to minimize any potential change in the form factor of the oral appliance. Additionally, in some embodiments, the transmission component can be placed at a location that is on the body of the oral appliance but not near the power source and/or other components of the circuit. The transmission component can be used to send information, via a wireless or wired connection, to a device that is not on the oral appliance.

As with other wireless communication elements described herein, the communication type can be either short range (up to 15 meters), such as Bluetooth, near field communication, Ultraband, and Zigbee, among other communication types, or longer range (greater than 15 meters), such as infrared or W-Fi communication types. As is commonly understood, longer range communication types can be used in short range applications, but short range communications types cannot be used for longer range applications that require distances longer than their maximum range.

As indicated in FIG. 2 by the arrows next to remote device 210, in some embodiments, short range communication (e.g., Bluetooth) can be used to communicate the compliance information to the remote device 210 and short or long range communication (e.g., W-Fi) can be used to communicate the information to another remote device 211, such as a desktop or portable computing device or to an output device, such as a printer or memory device. Such an implementation can be beneficial, for example, where the compliance information can be taken at a dentist's chair and its location is not within short range communication of the transmission component. This can allow for the use of a short range transmission component, which typically have a smaller form factor, less expensive, and use less power than longer range components.

In such embodiments, the compliance system 200 may also include a processor or other logic type circuitry to process the collecting, storage, and sending of the compliance information. Examples of a computing system and memory layout that may be suitable for use with embodiments of the present disclosure are provided in FIGS. 6 and 7 below. In some embodiments, the processor can also analyze the compliance data received and provide a compliance determination that can be sent to the remote device. Memory can also be provided to store the data or other compliance information (e.g., compliance determination). The processor/logic and memory can be provided by separate components, or can be provided by an integrated circuit, such as element 204 of FIG. 2.

As discussed, some embodiments may use a processor and memory or logic to perform various functions. Memory can be coupled to processor or logic circuit. The memory can be volatile or nonvolatile memory. Memory can also be removable (e.g., portable) memory, or non-removable (e.g., internal) memory. For example, memory 108 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disk read-only memory (CD-ROM)), flash memory, a laser disk, a digital versatile disk (DVD) or other optical disk storage, and/or a magnetic medium such as magnetic cassettes, tapes, or disks, among other types of memory.

Memory can also be located internal to another remote device (e.g., enabling data or computer readable instructions to be uploaded or downloaded over the Internet or another wired or wireless connection). Memory can also store executable instructions, such as, for example, computer readable instructions (e.g., software), for providing the functionalities described and executed by the processor according one or more embodiments of the present disclosure.

A processor can be any suitable computing device processor for accomplishing the functions described herein.

Logic can be provided by an integrated circuit and can be used in place of a processor (and in some cases, memory) to provide the functionalities described herein.

Remote devices can be various devices capable performing the functions of a remote device in accordance with embodiments of the present disclosure (e.g., a desktop computer, laptop computer, tablet, smart phone, and/or personal digital assistant (PDAs), for instance, among others).

In some embodiments, the remote device includes a display. In some embodiments, the display can be a portion of a device separate from the remote device and may be alternatively referred to as a display device. Display 104 can be a graphic user interface (GUI) that can provide (e.g., display and/or present) and/or receive information (e.g., data and/or images) to and/or from a user. For example, display can include a screen that can provide information to a user and/or receive information entered into display by the user. However, embodiments of the present disclosure are not limited to a particular type of display.

Figure 3:
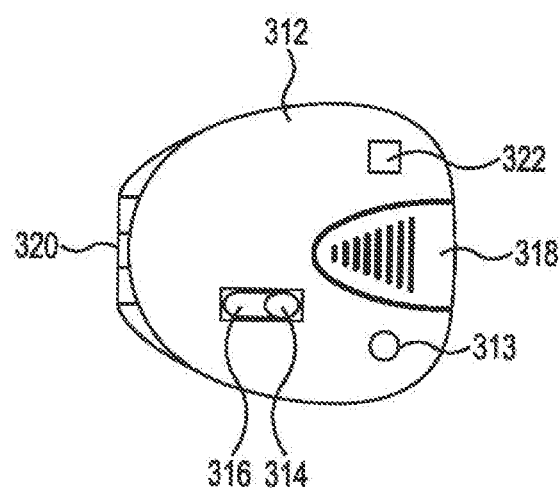
FIG. 3 illustrates a front view of a storage case for an oral appliance according to a number of embodiments of the present disclosure.

FIG. 3 illustrates a front view of a storage case for an oral appliance according to a number of embodiments of the present disclosure. The embodiment shown in FIG. 3 is another type of compliance system that can be used to determine whether a patient is complying with their treatment plan with regard to the amount of time they are supposed to be wearing their dental appliance. The storage case may incorporate one or more portions of the extra-oral compliance indication system 1094, shown in FIG. 1A.

In the embodiment of FIG. 3, the oral appliance compliance system includes an oral appliance storage case wherein an oral appliance is to be placed when not in the mouth of a patient. The storage case includes a compliance component attached to a body 312 of the storage case. The compliance component includes a power source 322 and a sensor to indicate whether the patient is not storing the device for a period over a threshold period of time.

The sensor can be any suitable sensing mechanism that allows the tracking of the time that the oral appliance is within the storage case. In the embodiment illustrated in FIG. 3, the sensor is a switch mechanism having a slider 314 located within a slot 316 that closes a circuit attached to the power source. The circuit can be similar to those described in FIGS. 1 and 2 or could be a circuit having the power supply, a clock circuit, and the switch mechanism.

In some embodiments, the sensor includes a patient actuated sensor to indicate at least one of the placement into and the removal from the storage case of the appliance. For example, as shown in the embodiment of FIG. 3, the patient places the switch in the "on" position when the patient places their dental appliance in the storage case, thereby activating the circuit. When they remove the oral appliance from the storage case, they place the switch in the "off" position and the circuit is deactivated.

In some embodiments, the threshold period of time represents the maximum amount of time that a patient can have the appliance out of their mouth during a particular treatment period. This would indicate that the oral appliance has been in the mouth for the minimum amount of time as prescribed by the patient's treatment plan and therefore, the patient is in compliance.

The threshold period of time for storing the oral appliance can be any suitable amount of time determined by a treatment professional. This time can be set, for example, by the treatment professional and can be kept on a remote computing device (mobile device such as a phone, tablet, or laptop or a desktop computing device, accessed via a wired or wireless connection) that is used to determine whether compliance is met once data from the circuit is received. This time period can be a standard time period for a particular stage of a treatment plan (e.g., stage 2's threshold is 240 hours over wear over a two week period regardless of the patient) or can be determined by the treatment professional and provided to the computing device once the treatment plan has been created by the treatment professional. A treatment plan as used herein can describe plans having just one period of treatment (e.g., when describing a period of use for some types of mandibular adjustment devices, some devices for addressing a malocclusion, such as overjet or overbite, a bruxism device, some types of retainers, etc.) or can describe plans having multiple stages of treatment each having a period of treatment (e.g., when describing a period of use for some types of mandibular adjustment devices, some devices for addressing a malocclusion, such as overjet or overbite, treatment for aligning teeth using aligners, etc.).

In some embodiments, rather than having a switch mechanism, the sensor is activated by the closure of the storage case. For example, the sensor can be activated by a mechanism on the latch 318 of the storage case 312 wherein closure of the storage case and securing of the latch closes the circuit, thereby activating the sensor. In some embodiments, the securing of the latch can open the circuit.

Alternatively, the actuation mechanism can be associated with the hinge 320 of the storage case. For example, the sensor can be activated by a mechanism on the hinge 320 of the storage case 318 wherein closure of the storage case and positioning the hinge in a closed position closes the circuit, thereby activating the sensor. In some embodiments, the positioning of the hinge in a closed position can open the circuit.

Some such devices can also activate an alarm on or in the case if the oral device has been in the case for greater than a threshold time period. The time period can, for example, be a continuous time that the oral device is in the case (e.g., more than three consecutive hours in the case) or can be a cumulative time period that is made up of several non-continuous time periods that are accumulated over a treatment period (e.g., a few hours each 24 hour day). The time period threshold can be determined and set, for example, in the hardware or software of the case, during manufacture, after manufacture, set by the treatment professional, or by the patient.

Further, the data from the sensor and/or an indication to initiate an alarm can be sent to a mobile device, desktop device, or other suitable device that can be accessed by the treatment professional or the patient, or other interested party (e.g., parent or guardian of the patient). Where an alarm indication is sent, the alarm can be initiated on a device such as a remote computing device accessible by the user or treatment professional. Such transfer of information can be accomplished in any suitable manner, for example, via Bluetooth or other wireless communication method.

Similar to the embodiment of FIG. 2, the embodiment of FIG. 3 can include a transmitter for transmitting compliance data. In this manner, less information needs to be stored on the storage case and therefore, the components of the circuit can cost less, among other benefits. For example, in some embodiments, the compliance component includes memory for storing compliance data. If the data is periodically transmitted to a remote device, the data can be removed from memory and therefore a smaller memory store may be used with the system.

In such embodiments, the compliance component includes a transmitter for transmitting compliance data and the memory stores the compliance data in a transmission queue until a device to receive the compliance data is within range to receive the data. Utilizing a queue can be beneficial, for example, by allowing the memory to hold compliance information that has been collected over a period of time and then transmit the data at a later time, such as at a check-up with the treatment professional or at the end of the treatment period in which the oral appliance is being used.

In some embodiments, the storage case can include a light source that can be used for various functions related to compliance. For example, a light source may be provided as an indicator that the patient is meeting a compliance goal. A light source may be provided as an indicator that the appliance has been placed correctly in the storage case such that compliance is being tracked. Further, a light source could be provided to aid an imaging sensor in sensing the appliance, as will be discussed in more detail with respect to the embodiment illustrated in FIG. 4 below.

When used to indicate compliance, in some implementations, the storage case can have one or more indicators, such as indicator 313, thereon that can be used to indicate compliance of other important information to the user and/or treatment professional. Any suitable indicator can be used that will alert a user or treatment professional to information that they should be aware of (e.g., status of compliance, etc.).

For example, light sources that illuminate to indicate whether the patient is in compliance or out of compliance with their wearing of the appliance. For example, the storage case may have a light that illuminates when the user is in compliance, such as the indicator 313 (e.g., a light source) shown on the exterior surface of the body of the storage case 312 of FIG. 3. Systems such as this could, alternatively, be designed to illuminate only when the patient is out of compliance.

Additionally, in some embodiments, the light source may be a display that displays text or one or more symbols that indicate compliance or non-compliance. Any suitable text or symbols could be used for such a purpose and the display utilized could be sized to accommodate such text and/or symbols.

Further, multiple lights could be used to indicate a level of compliance. For example, two lights, one green to indicate compliance and one red to indicate non-compliance, three lights with a green and red as above and a yellow to indicate they are nearing non-compliance, multiple lights where all illuminated indicates compliance and less lights indicates their level of non-compliance, etc. As the reader will understand, any suitable light arrangement could be used in the various embodiments of the present disclosure.

In another embodiment, an oral appliance compliance system includes a compliance component attached to a body of an oral appliance storage case wherein an oral appliance is to be placed when not in the mouth of a patient and the compliance component includes a power source and a sensor to indicate whether the patient is not storing the device for a period over a threshold period of time. In such an embodiment, the actual time that the appliance is not in the storage case is measured, which may be a better indicator of compliance by a patient in some implementations. One such embodiment is discussed with respect to FIG. 4.

Figure 4:
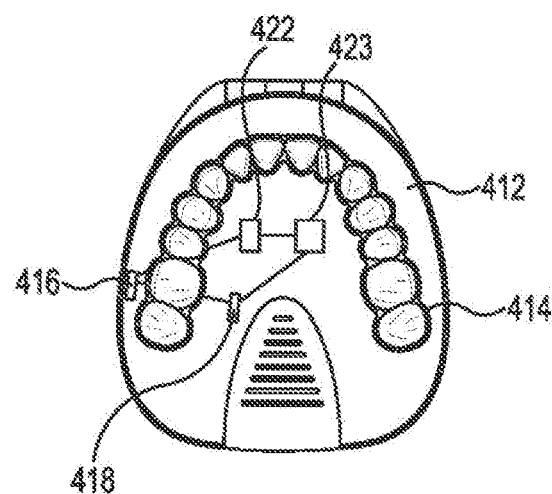
FIG. 4 illustrates an interior view of a storage case having an oral appliance therein according to a number of embodiments of the present disclosure.

FIG. 4 illustrates an interior view of a storage case having an oral appliance therein according to a number of embodiments of the present disclosure. In the embodiment of FIG. 4, the storage case includes a sensor that senses a characteristic of the oral appliance when the appliance is positioned within the storage case. The characteristic can be any characteristic of the oral appliance that can indicate its presence within the storage case. For example, in some embodiments, the characteristic can be the presence of a metallic material within the oral appliance. This could, for example, be accomplished through use of a magnetic sensor. Some or all of the components of the storage case in FIG. 4 may correspond to the components of FIG. 1A. For instance, the components of the storage case in FIG. 4 incorporate one or more portions of the extra-oral compliance indication system 1094, shown in FIG. 1A.

In some embodiments, the compliance component can be positioned within an oral appliance storage case where an oral appliance is to be placed when not in the mouth of a patient. The compliance component can include a power source and a sensor to indicate whether the patient is not storing the device for a period exceeding a threshold period of time.

In some embodiments, the compliance components can be added to a storage case that has already been fabricated. In this manner, compliance functionality can be added to any existing storage case for an oral appliance. This can be accomplished by, for example, placing the elements of the compliance system inside the storage case or using adhesive to affix one or more of the elements of the compliance system to the inside and/or outside surfaces of the body of the storage case.

For instance, in some embodiments, the sensor senses a characteristic of the oral appliance when the appliance is positioned within the storage case. Alternatively, the sensor can be designed to sense a characteristic of the oral appliance when the appliance is not positioned within the storage case (when the appliance is removed, it is no longer proximate to the sensor and, if the sensor is a proximity sensor, the sensor senses that the appliance is no longer proximate to the sensor). Examples of suitable sensors can be one or more of a proximity, density, mass, pressure, magnetic, and/or an imaging sensor, among other suitable types of sensors that can identify the physical presence of the appliance in the storage case.

In some embodiments, the characteristic of the appliance can be of an element provided on or within the appliance body. If the element is on the body or has a portion of the element that is in contact with the patient's tissue or fluids, it may be beneficial that the material be biocompatible. In some such embodiments, the oral appliance can include a biocompatible element that can be sensed by the sensor. Some magnetic materials would be examples of such biocompatible materials capable of being sensed by a sensor.

In embodiments where a storage case is utilized to accommodate the elements of the compliance system or where the power supply can sufficiently power such a functionality, compliance information can be pushed to a remote device by the transmitter of the compliance system. This may allow the compliance system to have little or no memory for storage and will allow the patient and/or treatment professional to immediately see the compliance data or analysis of compliance, or to allow such compliance analysis to take place within a close time period to when the data is being taken. This may be beneficial, for example, as the patient can rectify their behavior before the end of a treatment period and may be able to come into compliance with their treatment plan if their appliance wearing behavior is changed to increase the amount of time they are wearing the appliance.

As discussed above, in some implementations, one or more light sources may be part of the compliance system. A light source may, for example, be provided as an indicator that the appliance has been placed correctly in the storage case such that compliance is being tracker. Further, a light source could be provided to aid an imagine sensor in sensing the appliance.

In the embodiment shown in FIG. 4, a light source 416 is placed on one inside surface of the storage case 412 and an imaging sensor 418 is placed on another inside surface of the storage case, such that when an appliance 414 is placed into the storage case, the appliance can diminish or block the transmission of light from the light source that is received by the imaging sensor.

In this manner, the emitter (light source) and the detector (imaging sensor) can work together to identify whether the appliance is in the storage case. For example, if the imaging sensor indicates a certain voltage when the appliance is present and a different voltage when the appliance is not present, this data can be compared and a determination as to whether the appliance is present can be made.

Additionally, a system may just look at one voltage and compare it with a threshold voltage stored in memory of the device doing the analysis to determine whether the appliance is present or not. For example, a device may have a threshold reference voltage stored in memory 423 (e.g., provided in a processor/memory component 422) that indicates that the appliance is in the storage case.

The imaging sensor can provide a voltage level to the device doing the analysis and a determination can be made based upon whether the voltage level sent from the imaging sensor meets the threshold reference voltage. If the threshold reference voltage is met, then the appliance can be determined to be within the storage case. Alternatively, the analysis could be performed with a threshold reference voltage indicating that an appliance is not in the storage case. As the reader will understand, such a system could alternatively be used to show that the appliance is not in the storage case.

In other imaging sensor embodiments, the imaging sensor can be used to detect a feature on the dental appliance. For example, in some embodiments, the dental appliance can include a bar code or other identifier that indicates that it is a dental appliance as opposed to another object placed in the case. Any suitable identification marker can be used in such embodiments (e.g., one or more letters, numbers, shapes that can be identified by the system, or combination thereof). This could be accomplished by providing a known image on the appliance and comparing an image captured of the image with an image stored in memory on a computing device, for example.

Alternatively, a location on the appliance could be identified as being the location where an identifier will be present and if any identifier is located in an image captured of that location, then the appliance is deemed to be present. In this manner, analysis of the image captured is easy as it can just identify where an identifier is in the location or not.

The shape of the dental appliance may also change over time and could be used to determine whether the dental appliance is being used according to the treatment plan. For example, as a dental aligner is used to move teeth, it will change shape in a manner that may be predicted. In such an embodiment, the shape of the entire dental appliance or a portion that shows such deformation can be imaged and evaluated by the system. This can, for example, be accomplished by comparing an image of the appliance taken by the imaging sensor against one or more other images to determine if the appliance has deformed beyond a threshold change in shape.

Additionally, a pigment may be added to a portion of the dental appliance that, when interacting with saliva of the patient, changes color. In such embodiments, an imaging sensor can be used to capture the color of the pigment and determine whether the patient is being compliant based on comparing the captured image to colors stored in memory of a computing device that are indicative of dental appliances at certain periods of wear. In this manner, a pigment sample from an appliance that has been worn for 48 hours can be compared to the appliance of the patient, at a time when they should have worn their appliance for 48 hours, to see if the color of the pigments are within a threshold difference of being a match. If they are within the threshold of matching, then the patient is considered as being compliant in their wearing of the dental appliance.

This information can be used to determine the amount of time the appliance is in the storage case or out of the storage case, which can be used to infer how much time the appliance is in the patient's mouth and, thereby, compliance with the treatment plan. In some implementations, the emitter and detector can be positioned near each other and may even be on the same surface of the storage case.

In some embodiments, such as when used to provide illumination to an imaging sensor, the light source may not be visible to the human eye. This may be beneficial if the patient keeps their storage case near their bed so it does not disturb their sleep. For example, the light source and imaging sensor may operate in the UV or infrared wavelength ranges that are outside a human vision range.

Figure 5:
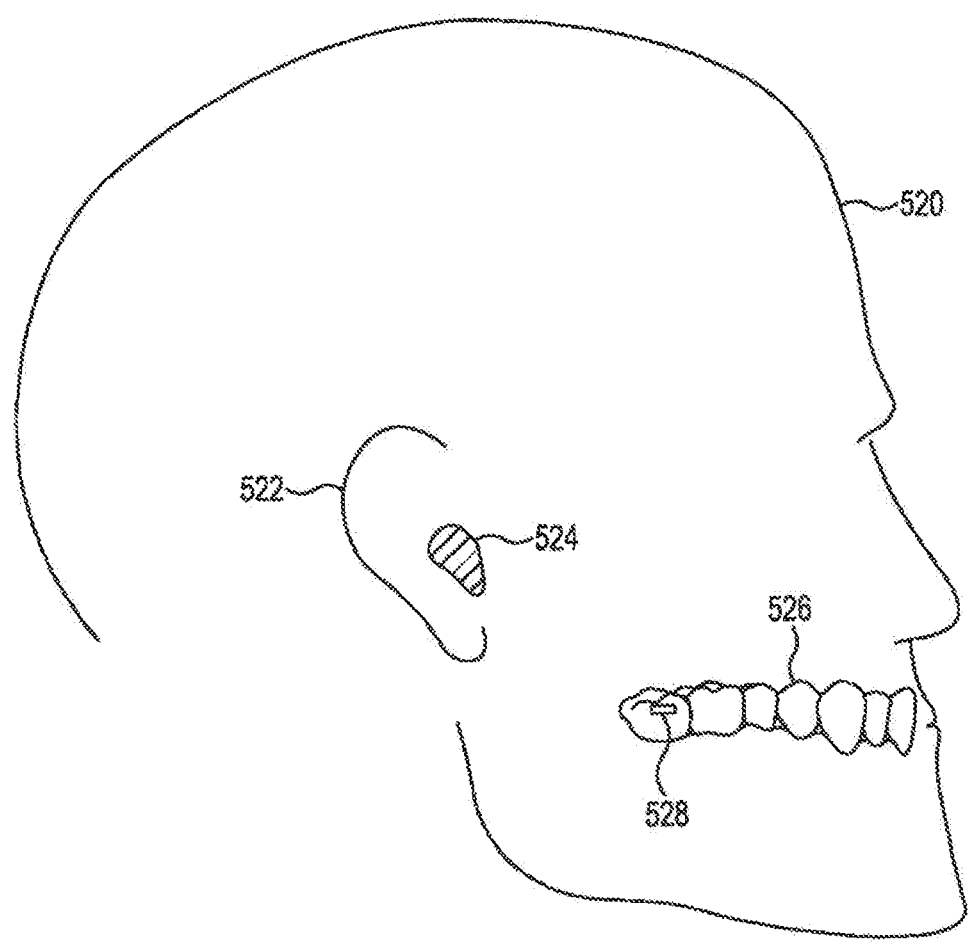
FIG. 5 illustrates a side view of the head of a patient with an oral appliance having a compliance indicator thereon positioned within the mouth of the patient and a remote sensor located in the ear of the patient according to a number of embodiments of the present disclosure.

FIG. 5 illustrates a side view of the head of a patient with an oral appliance having a compliance indicator thereon positioned within the mouth of the patient and a remote sensor located in the ear of the patient according to a number of embodiments of the present disclosure. For example, in some embodiments, an oral appliance compliance system includes an oral appliance and a compliance component attached to the body. In such embodiments, the compliance component can include a material that can be sensed by a remote sensor to indicate whether the oral appliance is in a patient's mouth.

In the embodiment of FIG. 5, the oral appliance 526 having a compliance component 528 thereon is positioned in the mouth of the patient. A remote sensing device 524 is placed within a threshold distance within which the compliance component 528 can be sensed. For example, in the embodiment illustrated in FIG. 5, the remote sensing device 524 is an ear piece that is positioned in the ear 522 of the patient. In other embodiments, the remote sensing device may be of a different form factor that may be positioned elsewhere on the head 520 or on another part of the patient's body or clothing, as will be described in more detail below.

The compliance component can be a passive component that is sensed when the remote sensor interacts with the compliance component. For example, some embodiments can have a passive detectable component (non-powered and/or non-transmitting) on or in the oral appliance and active detector components located outside the mouth of the patient. In such an embodiment, the active detector components can send out a signal that: can be received and a return signal sent by the passive detectable component (e.g., if the passive detectable component receives power from the active detector components) or be bounced off the passive detectable component, or the passive detectable component can be sensed (e.g., magnetic) by the active detector components.

For example, a small earpiece or other wearable or portable device, embedded with a Hall Effect sensor, can be worn throughout treatment. This device would detect when a magnet embedded in the aligner is detected. In such embodiments, the detection distance can be calibrated to the distance between where the device will be located and, for example, the 2nd molar of a particular patient (customized to a particular patient's needs), of an average patient (designed to be effective for most patients), or of a largest possible patient (to ensure the system will detect properly for all patients).

The device having the active detector components that is located outside the patient's mouth (extra-oral) can have various form factors. For example, the extra-oral wearable device can be a skin patch, wristband, watch, necklace, earing, accessory to a smart phone, etc. The passive detectable component could be or include a magnet, capacitor, or coil antenna. One benefit of such designs is that an extra-oral appliance may have more relaxed design constraints (e.g., size, biocompatibility, temperature and/or wetness of the environment), than an intra-oral appliance, which would only contain passive components.

As inferred by the possible form factors discussed above, the remote sensing device can be a portable device. This can be beneficial as the device can be removed from the body of the patient when the oral appliance is not being used, among other benefits. Further, as discussed with respect to the case in FIG. 3, in some embodiments, the portable device can include an indicator (e.g., one or more light sources, a display, etc.) that allows a user to see an indication of the level of compliance thereon.

The compliance component (passive detectable component) can be made from a variety of suitable materials depending on the conditions in which the compliance component is implemented. For example, in some embodiments, the compliance component material is a metallic material. In some implementations, the material is magnetic.

This can allow the compliance component to be non-power and detectable by a magnetic or electric field. This is accomplished because the magnetic or electric field will be slightly perturbed by the presence of a metallic object in proximity to the field and this perturbation can be sensed by a sensor.

In some embodiments, the compliance component includes a power source and the material that can be sensed is in the form of an antenna or a transmitter, wherein the transmitter transmits a signal that can be sensed by the remote sensor in the extra-oral appliance. For example, the material can be in the form of an antenna and the antenna transmits a signal that can be sensed by the remote sensor of the extra-oral device. The intra-oral device can be powered by a power source similar to the devices shown in FIGS. 1B and 2. In some embodiments, the intra-oral device can be energized by a signal from the extra-oral device received by the antenna of the intra-oral device and, once energized, can transmit a signal via the antenna to the extra-oral device.

In some embodiments, one extra-oral device can provide the power to the intra-oral device and another extra-oral device can receive the signal. For example, the signaling material of the intra-oral device can be in the form of an antenna and wherein the antenna transmits a signal that can be sensed by the remote sensor of a first device when the antenna is energized by a signal received by the antenna from a second remote device.

In some embodiments, an oral appliance compliance system can include a compliance component to be attached to a body of an oral appliance, wherein the compliance component includes a material that can be sensed by a remote sensor to indicate whether the oral appliance is in a patient's mouth. In this example embodiment, a remote sensing device can have the remote sensor therein to sense the presence of the material within a threshold distance from the remote sensor. In this manner, the sensing functionality can be performed by components that do not have to be located in the mouth of the patient. This can allow for a large form factor, components with more functionality or power, less biocompatibility considerations with respect to placing items in the patient's mouth, and other benefits.

In some such embodiments, the remote sensing device is a device that is wearable by the patient. For example, the remote sensing device is a device having the remote sensor therein selected from the group including: a piece of jewelry worn on the head of the patient (e.g., earring, ear piece, etc.), a piece of jewelry worn on the neck of the patient (e.g., necklace, etc.), a piece of jewelry worn on an appendage on the patient (e.g., watch, bracelet, anklet, etc.), a hair accessory, a pair of eyeglasses, or a device mounted to any such item.

The device may also be incorporated into an item that can be attached to the patient. For example a patch could include the remote sensing device and could be attached via an adhesive or other suitable type of attachment to attach to the body or the patient or to their clothing.

In some embodiments, an oral appliance compliance system includes an oral appliance to be placed into the mouth of a patient, a compliance component including a material that can be sensed by a remote sensor to indicate whether the oral appliance is in a patient's mouth, wherein the compliance component is attached to the oral appliance, and a remote sensing device having the remote sensor therein to sense the presence of the material within a threshold distance from the remote sensor. In this manner, compliance can be determined based on a proximity type of sensing and, as such, the sensing functionality can be located outside the mouth of the patient, in some implementations.

In embodiments where the compliance component is inside the mouth of the patient, the compliance component can be made from one or more biocompatible materials. Additionally or alternatively, the material that can be sensed is a biocompatible material. These types of embodiments can be beneficial, for example, if the compliance component is exposed to the patient's tissue or bodily fluids and as such may be review for compatibility by a government agency such as the US Food and Drug Administration.

The interaction between a compliance component and a remote sensor can be accomplished in a variety of suitable manners. For example, the interaction between the compliance component and the remote sensor can be accomplished via electromagnetic interaction. For instance radio frequency signals can be passed between an active or passive compliance component and a remote sensor.

In some implementations, the electromagnetic interaction between the compliance component and the remote sensor is via sensing of changes in an electromagnetic field. As discussed herein, this can be accomplished with a material that can be sensed when located within an electric or magnetic field that can be sensed by a sensing component. Examples of such material include magnetic materials and metallic materials, among others.

An embodiment such as those shown in FIGS. 1B-5 can generally be described as being an extra-oral dental appliance compliance indicator configured to be operational outside an oral cavity of a patient and configured to detect whether or not a dental appliance is being worn in the oral cavity of the patient. It should be noted that some embodiments of the present disclosure can be actuated intraorally as discussed herein.

Embodiments such as those shown in FIGS. 1B-5 also include an extra-oral sensor of the extra-oral dental appliance compliance indicator configured to sense whether a dental appliance is within the oral cavity of the patient and to provide a compliance signal to a processing device indicating whether the extra-oral sensor sensed that the dental appliance is within the oral cavity of the patient.

Figure 6:
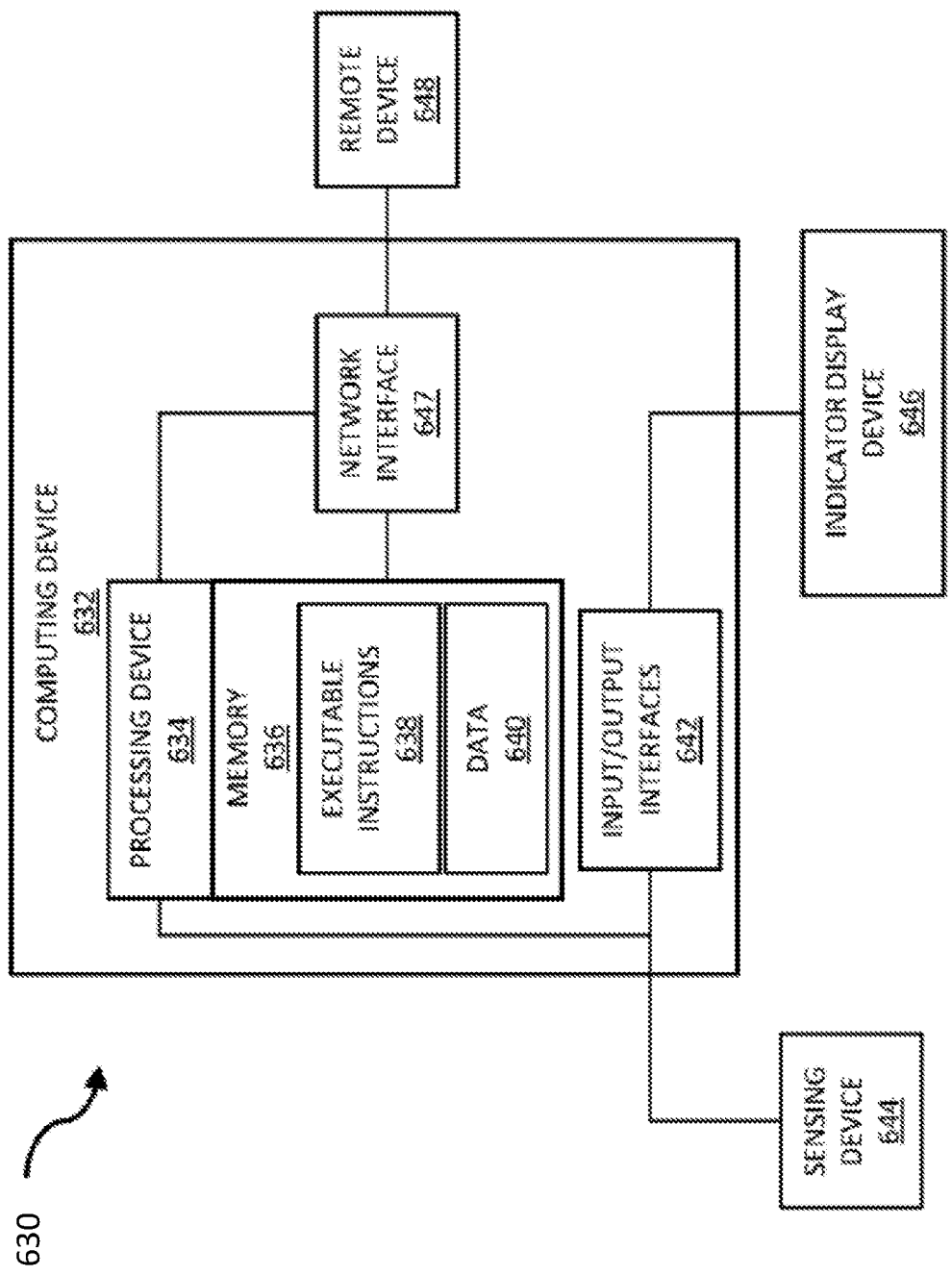
FIG. 6 illustrates a computing system for use in a number of embodiments of the present disclosure.

A processing device, such as device 634 discussed in FIG. 6, can be coupled (i.e., communicatively coupled) to the extra-oral sensor and the processing device configured to receive the compliance signal and to provide an indicator as to how much time the dental appliance has been worn. Such embodiments can also include a display device coupled to the processing device, the display device configured to display whether the patient is complying with a treatment plan based on how much time the dental appliance has been worn.

The extra-oral sensor can be several elements from FIGS. 1B-5. For example, the extra-oral sensor can be a power sensor configured to measure when an energy powered device on the appliance has lost energy such that an energy level of the energy powered device falls below an energy threshold indicative of the dental appliance being outside the oral cavity of the patient for more than a threshold period of time. In various embodiments, the extra-oral sensor is a power sensor that measures a power level of energy stored in an energy storage device. The embodiments of FIGS. 1B and 2 may have such power sensors as described above, in some implementations.

In various embodiments, the extra-oral sensor is incorporated into a case configured to store the dental appliance when the dental appliance is not in the oral cavity of the patient. The embodiments described with respect to FIGS. 3 and 4 may have such an extra-oral sensor, in some implementations.

As shown in the embodiment of FIG. 5, the extra-oral sensor can be a magnetic sensor configured to sense a magnetic field from a magnet on the dental appliance. For example, a Hall effect sensor or other suitable magnetic sensor could be utilized in various implementations.

In some implementations, the extra-oral dental appliance compliance indicator has the extra-oral sensor incorporated into a dental appliance packaging box and/or case.

FIG. 6 illustrates a computing system for use in a number of embodiments of the present disclosure. As shown in FIG. 6, computing device 632 of the computing system 630 can have a number of components coupled thereto. The computing device 632 can include a processor 634 and a memory 636. The memory 636 can have various types of information including executable instructions 638 and data 640, as discussed herein.

The processor 634 can execute instructions 638 that are stored on an internal or external non-transitory computer device readable medium (CRM). A non-transitory CRM, as used herein, can include volatile and/or non-volatile memory.

As discussed above with respect to FIG. 2, memory 636 and/or the processor 638 may be located on the computing device 632 or off of the computing device 632, in some embodiments. As such, as illustrated in the embodiment of FIG. 6, the computing device 632 can include a network interface 647.

Such an interface 647 can allow for processing on another networked computing device, can be used to obtain information about the patient (e.g., characteristics of the patient's mouth and/or treatment planning information) and/or can be used to obtain data and/or executable instructions for use with various embodiments provided herein. Also, as shown in FIG. 6, the network interface can allow for connection to one or more remote devices 648 (e.g., a mobile phone or other mobile or non-mobile computing device used by a patient, guardian, or treatment professional) to receive information from the compliance indication system regarding compliance of the patient in wearing the dental appliance.

In some embodiments, a computing device can be used to calculate time that the dental appliance has been worn and determine whether to initiate an indicator that the patient is either in compliance with their treatment plan regarding the amount of time the patient should be wearing the dental appliance or is not in compliance. This can be accomplished, for example, by executing instructions, via a processing device (e.g., computer processor), to compare an amount of time the patient has worn the dental appliance over a period of time to a treatment plan time threshold for that period of time. For example, if the time the patient has worn their dental appliance is calculated at 100 hours for a one week period of time and the time threshold for that time period is 98 hours, the patient can be considered as being in compliance with the treatment plan, which includes the time threshold for one or more periods of time over the time that the treatment plan is being performed.

As illustrated in the embodiment of FIG. 6, the computing device 632 can include one or more input and/or output interfaces 642. Such interfaces 642 can be used to connect the computing device 632 with one or more input and/or output devices 644, 646.

For example, in the embodiment illustrated in FIG. 6, the input and/or output devices can include a sensing device 644 and an indicator display device 646. As discussed herein, the sensing device can provide compliance information to the computing device 632, for example, by sensing when the dental appliance is within the oral cavity of the patient or is outside the oral cavity of the patient. The indicator display device 646 can be any suitable device for providing a patient, guardian, or treatment professional with an indication that the patient is in compliance or out of compliance with the treatment plan.

Such connectivity with input and output devices and network connections can allow for the input and/or output of data and/or instructions among other types of information. Some embodiments may be distributed among various computing devices within one or more networks, and such systems as illustrated in FIG. 6 can be beneficial in allowing for the capture, calculation, and/or analysis of information discussed herein.

The processor 634, can be in communication with the data storage device (e.g., memory 636), which has the data 640 stored therein. The processor 634, in association with the memory 636, can store and/or utilize data 640 and/or execute instructions 638 for compliance indication.

In various embodiments, the processing device 634 coupled to the memory 636 can cause the computing device 632 to perform the method comprising receiving, via a processing device, one or more compliance signals generated from an extra-oral sensor of an extra-oral dental appliance compliance indicator configured to be operational outside an oral cavity of a patient and configured to sense whether a dental appliance is within the oral cavity of the patient, calculating a time that the dental appliance has been in the oral cavity of the patient based on the received one or more compliance signals, comparing the calculated time to a treatment plan time threshold to determine if the patient is complying with a treatment plan, and initiating an indicator that indicates to the patient whether or not they are complying with the treatment plan based on the comparison of the calculated time to the treatment plan time threshold.

Such analysis can be accomplished one or more times for a treatment plan. For example, if a treatment plan has 30 stages, it would be possible to have different dental appliance compliance periods for each stage or possibly more, if desired.

Figure 7:
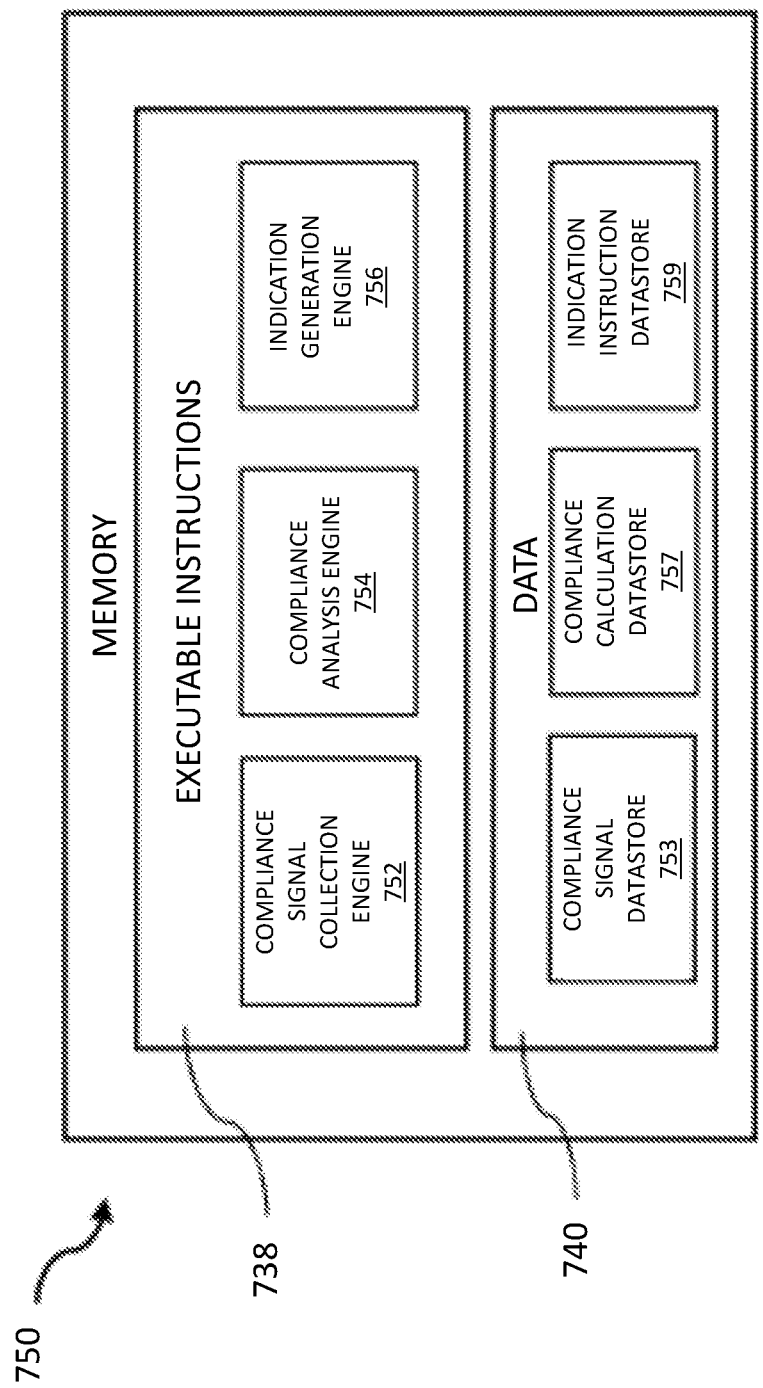
FIG. 7 illustrates a memory for use in a number of embodiments of the present disclosure.

FIG. 7 illustrates a memory for use in a number of embodiments of the present disclosure. Memory 750 may be, for example, memory 636 previously described in connection with FIG. 6.

The memory 750 may have various types of information including executable instructions 738 and data 740, as discussed herein. Additionally, the memory 750 may include one or more engines and datastores. A computing system can be implemented as an engine, as part of an engine, or through multiple engines.

The compliance signal collection engine 752 may include one or more automated agents configured to gather compliance signals from an extra-oral sensor and/or the compliance signal datastore 753. The compliance signal collection engine can use this information to calculate a time that a patient has been wearing the dental appliance. Compliance signals can, for example, be a time stamp (e.g., the time that the dental appliance was taken out of the oral cavity of the patient), an elapsed time quantity (e.g., the time period that the dental appliance was out of the oral cavity of the patient). When a time stamp is utilized, the processing device can execute instructions to determine the time period between a time stamp when the dental appliance was taken out and a time stamp when the dental appliance was placed back into the oral cavity. This information can then be used to determine the one or more time periods that the patient had the dental appliance positioned within their oral cavity.

The compliance analysis engine 754 may include one or more automated agents configured to determine whether the patient is in compliance with their treatment plan based on the time calculations made by the compliance signal collection engine 752 and one or more treatment plan thresholds stored, for example, in the compliance calculation datastore 757.

The indication generation engine 756 may include one or more automated agents configured to determine whether to initiate an indication be generated to inform the patient, guardian, or treatment professional that the patient is in compliance or out of compliance based on the determination made by the compliance analysis engine. The indication generation engine 756 can use data from the indication instruction datastore 759 to determine, for example, who to send an indication, what contact information to use to communicate the indication, how often to send an indication (every day/week/month, every time a non-compliance event occurs or wait until several events occur until sending an indication, etc.).

Through use of such executable instructions and data, embodiments of the present disclosure can determine whether a patient in compliance with a treatment plan and provide an indication to one or more parties to alert them of the status of the patient. Such embodiments can be beneficial in improving compliance and in tracking compliance more accurately so that, for example, changes in a patient's routine can be made before issues arise from the patient not following the treatment plan.

Figure 8:
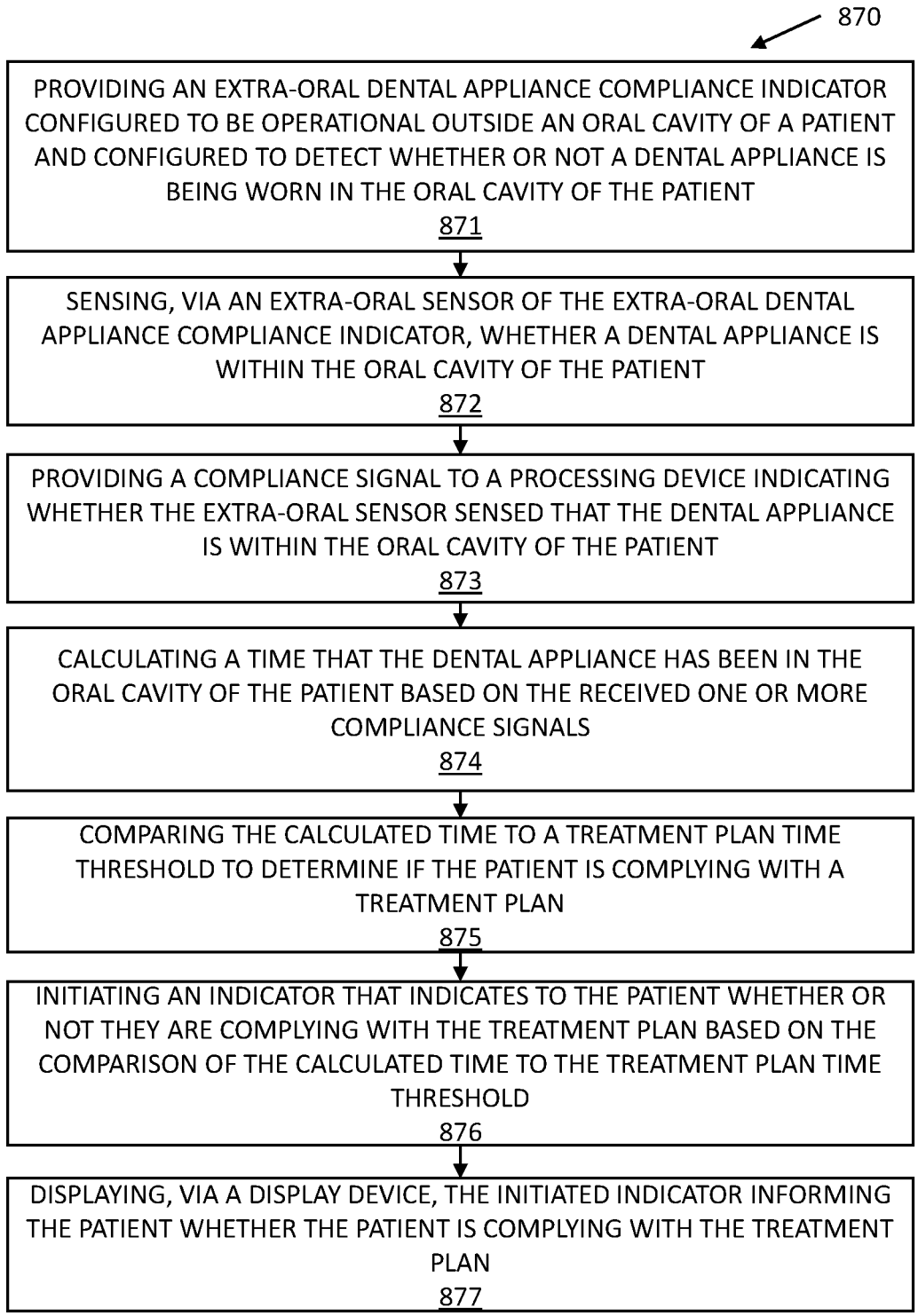
FIG. 8 illustrates a method for compliance indication, according to some implementations of the present disclosure.

FIG. 8 illustrates a flowchart of a method 870 for compliance indication, according to some implementations of the present disclosure. The method 870 may include more or less operations than those explicitly shown in FIG. 8. Some or all of the operations of the method 870 may be executed by the computing system 630 shown in FIG. 6 and/or the structures shown in FIG. 1A.

In the embodiment of FIG. 8, the compliance indication method 870 illustrated includes providing an extra-oral dental appliance compliance indicator configured to be operational outside an oral cavity of a patient and configured to detect whether or not a dental appliance is being worn in the oral cavity of the patient, at 871. The method further includes, at 872, sensing, via an extra-oral sensor of the extra-oral dental appliance compliance indicator, whether a dental appliance is within the oral cavity of the patient. At 873, a compliance signal is provided to a processing device indicating whether the extra-oral sensor sensed that the dental appliance is within the oral cavity of the patient.

The time that the dental appliance has been in the oral cavity of the patient based on the received one or more compliance signals is calculated at 874. The calculated time is compared, at 875, to a treatment plan time threshold to determine if the patient is complying with a treatment plan.

An indicator that indicates to the patient whether or not they are complying with the treatment plan based on the comparison of the calculated time to the treatment plan time threshold is initiated, at 876. And, at 877, the initiated indicator informing the patient whether the patient is complying with the treatment plan, can be displayed, via a display device. Through use of such an embodiment, compliance can be determined, and the information can be presented to a patient, guardian, or treatment profession to allow them to better assess the compliance of the patient among other benefits.

In some embodiments, the method can also include measuring, via a power sensor, when an energy powered device on the appliance has lost energy such that an energy level of the energy powered device falls below an energy threshold indicative of the dental appliance being outside the oral cavity of the patient for more than a threshold period of time. As discussed with respect to FIG. 1B, the power sensor can, for example, be configured to close a circuit only when the dental appliance is outside the oral cavity of the patient. In such an embodiment, the circuit will only be in operation when the dental appliance is not being worn by the patient.

Figure 9:
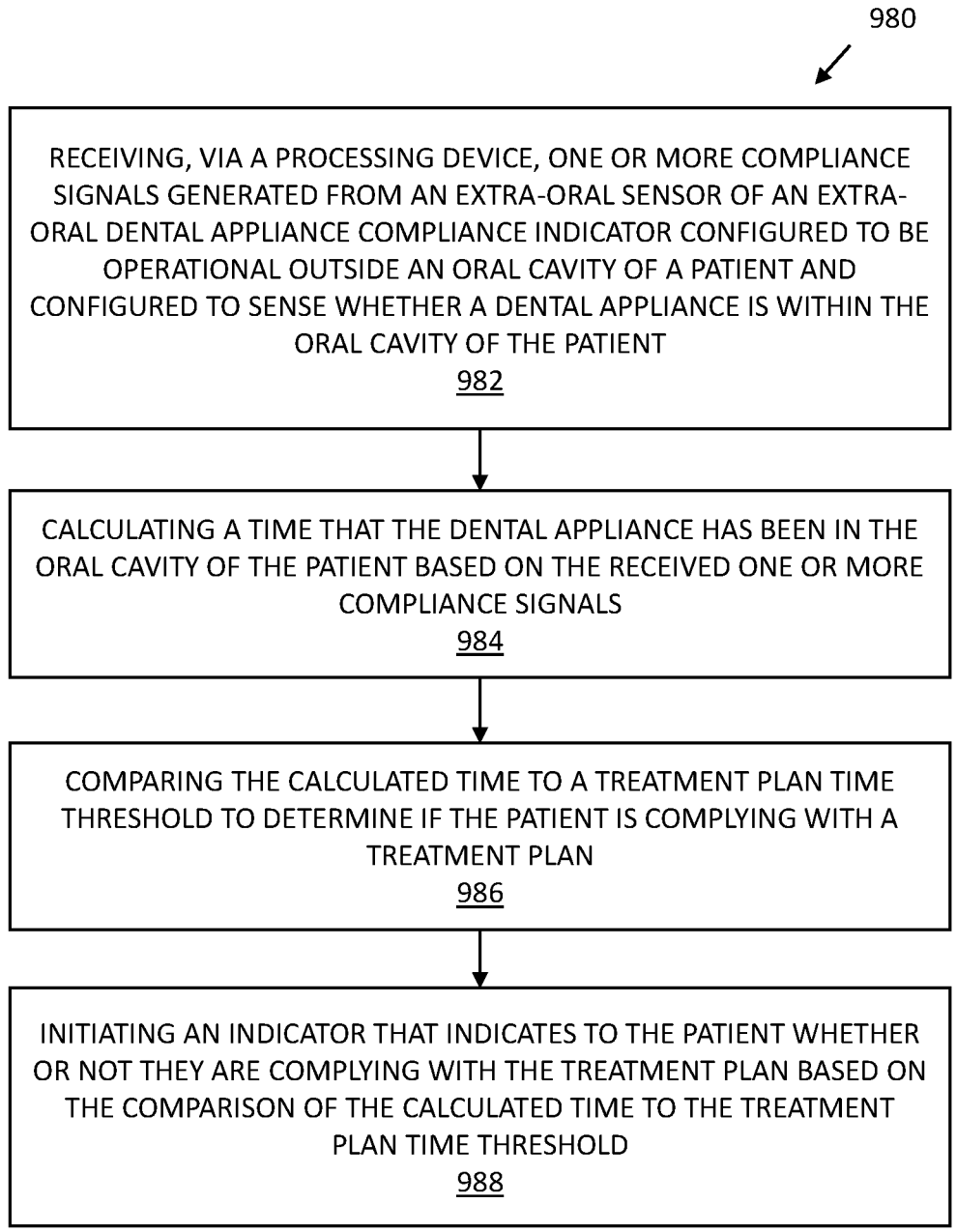
FIG. 9 illustrates another method for compliance indication, according to some implementations of the present disclosure.

A method embodiment as shown in FIG. 9 can also include a calculation process for calculating how much time the dental appliance has been worn based on the compliance signal received from the extra-oral sensor. This can be accomplished by the processes described herein and can be handled via executing instructions via the processing device, such as the device shown at 634 of FIG. 6.

Methods can also include determining an amount of time the dental appliance has been out of the oral cavity over a period of time to determine how much time the dental appliance is being worn. For example, a period of time could be a stage of a treatment plan, a day, a week, a month, during the entire treatment plan, or other suitable period of time. The amount of time the dental appliance has been out of the oral cavity can be continuous time (e.g., an uninterrupted span of 14 hours) or cumulative time over a period (e.g. 7 hours on day 1, 10 hours on day 2, 14 hours on day 3, 4 hours on day 4, and 15 hours on day 5 for a total cumulative time over the five day period of 50 hours).

In some embodiments, the processing device is configured to have a real time clock circuit that is used with the compliance signal to determine a time period that the dental device has been outside the oral cavity of the patient. The extra-oral sensor can also include or alternatively include a clock circuit configured to count the amount of time that the dental appliance is outside the oral cavity of the patient. As discussed herein, such timing circuits can be beneficial in providing accuracy to the timing measurements used in the determination of compliance.

FIG. 9 illustrates another method for compliance indication, according to some implementations of the present disclosure. As with the method of FIG. 8, the method 980 may include more or less operations than those explicitly shown in FIG. 9. Some or all of the operations of the method 980 may be executed by the computing system 630 and/or other structures shown in FIG. 9.

In the embodiment of FIG. 9, the compliance indication method 980 includes receiving, via a processing device, one or more compliance signals generated from an extra-oral sensor of an extra-oral dental appliance compliance indicator configured to be operational outside an oral cavity of a patient and configured to sense whether a dental appliance is within the oral cavity of the patient, at 982.

A time that the dental appliance has been in the oral cavity of the patient based on the received one or more compliance signals is calculated, at 984. The calculated time is compared, at 986, to a treatment plan time threshold to determine if the patient is complying with a treatment plan. An indicator that indicates to the patient whether or not they are complying with the treatment plan based on the comparison of the calculated time to the treatment plan time threshold is initiated, at 988.

Similar to the embodiment of FIG. 8, in embodiments such as that shown in FIG. 9, the method can also include displaying, via a display device, the initiated indicator informing the patient whether the patient is complying with the treatment plan. The displaying of such information can, for example, by accomplished through use of a light emitting diode display device, presentation of a voltage value on a display device, or an indication presented on a software application on a display of a mobile device, among other suitable display mechanisms. Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

Figure 10:
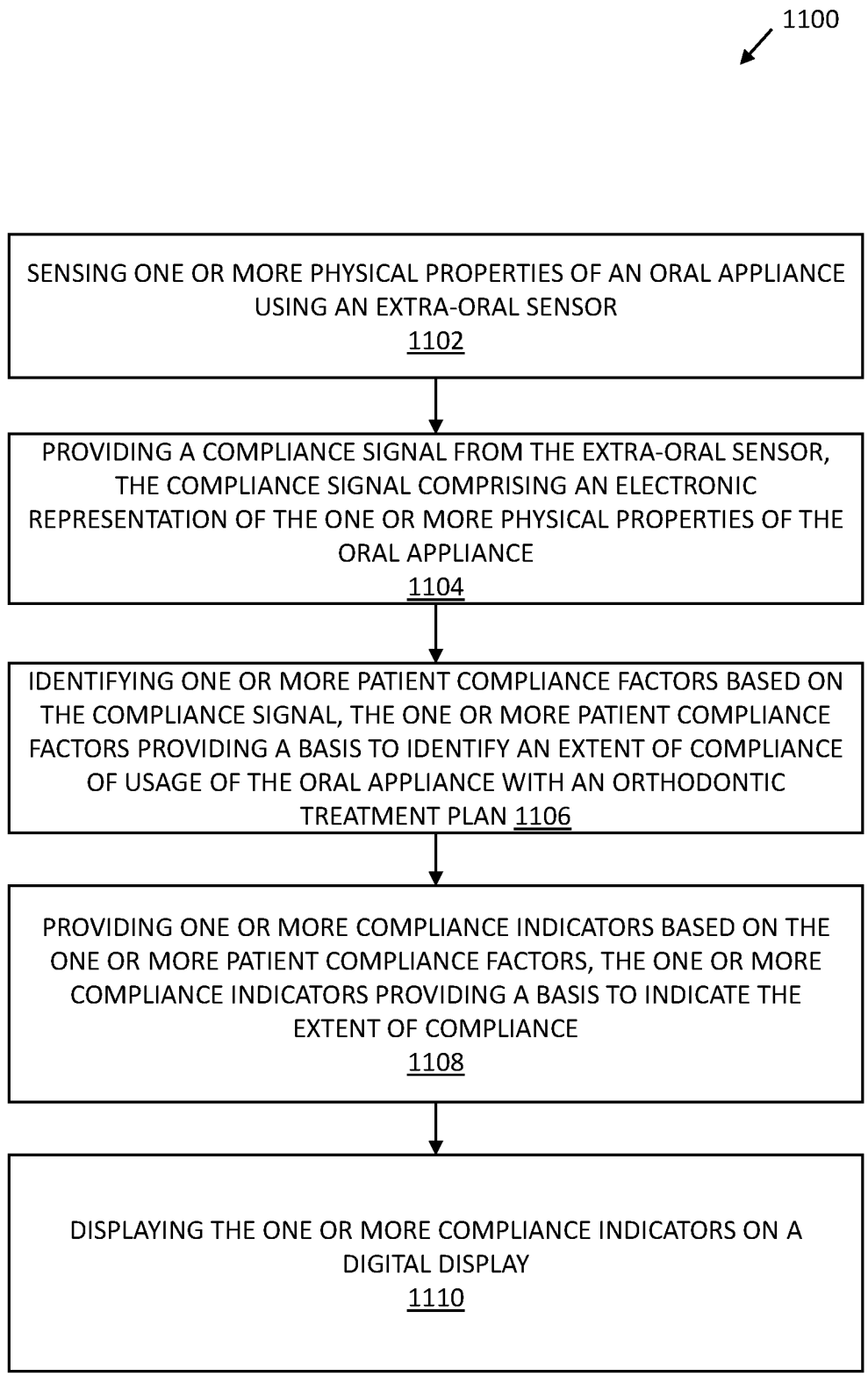
FIG. 10 shows a flowchart of a method of providing compliance indicators, according to some implementations of the present disclosure.

FIG. 10 shows a flowchart of a method 1100 of providing compliance indicators, according to some implementations. As with other methods herein, the method 1100 may include more or less operations than those explicitly shown in FIG. 10. Some or all of the operations of the method 1100 may be executed by any of the structures described herein.

At an operation 1102, one or more properties of an oral appliance may be sensed using an extra-oral sensor. The extra-oral sensor may comprise a discharge circuit configured to discharge power from a power source through a power draining element when the oral appliance is at a specified orientation relative to an oral cavity. The extra-oral sensor may comprise a magnetic sensor configured to detect when the oral appliance is at a specified orientation relative to an oral cavity. In some implementations, the extra-oral sensor comprises a Hall effect sensor incorporated in an extra-oral cavity of a patient associated with the oral appliance. The extra-oral sensor may include a metallic sensor configured to detect a metallic portion of the oral appliance. Such a metallic sensor may be incorporated into a case of the oral appliance. Further, the extra-oral sensor may comprise a biosensor configured to detect presence or absence of one or more biological chemicals on the oral appliance. In some implementations, the extra-oral sensor comprises a light source sensor configured to determine whether the oral appliance blocks a light source. The light source sensor may be incorporated into a case of the oral appliance. In various implementations, the extra-oral sensor comprises one or more image sensors configured to capture an image of the oral appliance.

At an operation 1104, a compliance signal may be provided from the extra-oral sensor. The compliance signal may comprise an electronic representation of the one or more physical properties. In some implementations, the electronic representation of the one or more physical properties of the oral appliance represents the one or more physical properties of the oral appliance. The electronic representation of the one or more physical properties of the oral appliance may represent whether or not the oral appliance is in a case associated with the oral appliance. In some implementations, the electronic representation of the one or more physical properties of the oral appliance represents a location of the oral appliance.

At an operation 1106, one or more patient compliance factors may be identified. The one or more patient compliance factors may provide a basis to identify an extent of compliance of usage of the oral appliance with an orthodontic treatment plan. At an operation 1108, one or more compliance indicators may be provided. The one or more compliance indicators may provide a basis to indicate the extent of compliance. At an operation 1110, the one or more compliance indicators may be displayed on a digital display.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method comprising:
   sensing one or more physical properties of an oral appliance using an extra-oral sensor outside of an oral cavity, wherein the extra-oral sensor is configured to detect a compliance component of the oral appliance;
   providing a compliance signal from the extra-oral sensor, the compliance signal comprising an electronic representation of the one or more physical properties of the oral appliance;
   identifying one or more patient compliance factors based on the compliance signal, wherein the one or more patient compliance factors identify whether the oral appliance has been at a specified orientation relative to the oral cavity for a specified amount of time; and providing one or more compliance indicators based on the one or more patient compliance factors, the one or more compliance indicators providing a basis to indicate an extent of compliance.

2. The method of claim 1, wherein the extra-oral sensor comprises a discharge circuit configured to discharge power from a power source through a power draining element when the oral appliance is at a specified orientation relative to the oral cavity.

3. The method of claim 1, wherein the extra-oral sensor comprises a magnetic sensor configured to detect when the oral appliance is at a specified orientation relative to the oral cavity.

4. The method of claim 3, wherein the magnetic sensor comprises a Hall effect sensor incorporated in the extra-oral sensor outside of the oral cavity.

5. The method of claim 1, wherein the extra-oral sensor is incorporated into a case of the oral appliance.

6. The method of claim 1, wherein the extra-oral sensor comprises a biosensor configured to detect presence or absence of one or more biological chemicals on the oral appliance.

7. The method of claim 6, wherein the one or more patient compliance factors provide a basis to identify an extent of compliance of usage of the oral appliance based on the detection of the presence or absence of the one or more biological chemicals on the oral appliance.

8. The method of claim 1, wherein the electronic representation of the one or more physical properties of the oral appliance represents the one or more physical properties of the oral appliance.

9. The method of claim 1, wherein the electronic representation of the one or more physical properties of the oral appliance represents whether or not the oral appliance is in a case associated with the oral appliance.

10. The method of claim 1, wherein the electronic representation of the one or more physical properties of the oral appliance represents a location of the oral appliance.

11. The method of claim 1, further comprising displaying the one or more compliance indicators on a digital display.

12. A system comprising:
an extra-oral sensor configured to be outside of an oral cavity, the extra-oral sensor including a biosensor configured to detect presence or absence of one or more biological chemicals on an oral appliance, the extra-oral sensor configured to provide a compliance signal;
an extra-oral compliance indicator system coupled to the extra-oral sensor, the extra-oral compliance indicator system including:
one or more processors;
memory coupled to the one or more processors, the memory comprising computer-program instructions that, when executed by the one or more processors, cause the system to execute a method comprising:
identifying one or more patient compliance factors based on the compliance signal, the one or more patient compliance factors providing a basis to identify an extent of compliance of usage of the oral appliance with an orthodontic treatment plan; and
providing one or more compliance indicators based on the one or more patient compliance factors, the one or more compliance indicators providing a basis to indicate the extent of compliance.

13. The system of claim 12, wherein the extra-oral sensor comprises a discharge circuit configured to discharge power from a power source through a power draining element when the oral appliance is at a specified orientation relative to the oral cavity.

14. The system of claim 12, wherein the extra-oral sensor comprises a magnetic sensor configured to detect when the oral appliance is at a specified orientation relative to the oral cavity.

15. The system of claim 14, wherein the magnetic sensor comprises a Hall effect sensor incorporated in the extra-oral sensor outside of the oral cavity.

16. The system of claim 12, wherein the extra-oral sensor is incorporated into a case of the oral appliance.

17. The system of claim 12, further comprising a digital display configured to display the one or more compliance indicators.

18. The system of claim 12, wherein the extra-oral sensor includes a metallic sensor and the compliance component includes a metallic portion of the oral appliance.

19. The system of claim 12, wherein the extra-oral sensor includes a magnetic sensor and the compliance component includes a metallic or magnetic portion of the oral appliance.

20. The system of claim 12, wherein the extra-oral sensor includes a wireless sensor configured to detect transmission from the compliance component of the oral appliance.

21. A system comprising:
an extra-oral sensor configured to be outside of an oral cavity and to detect a compliance component of an oral appliance, the extra-oral sensor configured to sense one or more physical properties of the oral appliance and to provide a compliance signal, the compliance signal comprising an electronic representation of the one or more physical properties of the oral appliance;
a compliance analysis engine configured to identify one or more patient compliance factors based on the compliance signal, wherein the one or more patient compliance factors identify whether the oral appliance has been at a specified orientation relative to the oral cavity for a specified amount of time; and
an indication generation engine configured to provide one or more compliance indicators based on the one or more patient compliance factors, providing a basis to indicate an extent of compliance.

22. The system of claim 21, wherein the extra-oral sensor is incorporated into a case of the oral appliance.

23. A system comprising:
an oral appliance case including a biosensor configured to detect presence or absence of one or more biological chemicals on an oral appliance and to provide a compliance signal; and
an extra-oral compliance indicator system electronically coupled to the oral appliance case, the extra-oral compliance indicator system comprising:
one or more processors; and
memory coupled to the one or more processors, the memory comprising computer-program instructions that, when executed by the one or more processors, cause the extra-oral compliance indicator system to execute a method comprising:
receiving the compliance signal;
identifying one or more patient compliance factors based on the compliance signal, the one or more patient compliance factors providing a basis to identify an extent of compliance of usage of the oral appliance with an orthodontic treatment plan; and providing one or more compliance indicators based on the one or more patient compliance factors, the one or more compliance indicators providing a basis to indicate the extent of compliance.

24. The system of claim 23, wherein the extra-oral compliance indicator system comprises a mobile phone, a tablet, a laptop, a desktop computer, or some combination thereof.

25. The system of claim 23, wherein the oral appliance comprises a clear aligner or a retainer.

26. The system of claim 23, wherein the system further comprises one or more locational sensors configured to sense a location of an oral appliance to be stored in the oral appliance case and to provide a signal indicating the location, wherein the method further comprises:
  receiving the signal indicating the location;
  making a determination as to whether or not the oral appliance is at a specified location using the signal indicating the location; and
  providing one or more indications as to whether or not the oral appliance is at the specified location based on the determination.

27. The system of claim 26, wherein the method further comprises identifying the specified location.

28. The system of claim 26, wherein the one or more locational sensors comprise one or more Bluetooth sensors.

29. The system of claim 26, wherein the specified location is within the oral appliance case, within a patient's oral cavity, or some combination thereof.

* * * * *